(12) United States Patent
Hildeman et al.

(10) Patent No.: US 11,541,073 B2
(45) Date of Patent: Jan. 3, 2023

(54) METHODS OF ATTENUATING AN IMMUNE RESPONSE BY INHIBITION OF BFL1

(71) Applicant: Children's Hospital Medical Center, Cincinnati, OH (US)

(72) Inventors: David A. Hildeman, Cincinnati, OH (US); Andrew Herr, Cincinnati, OH (US); Suhas G. Kallapur, Cincinnati, OH (US); Jarek Meller, Cincinnati, OH (US); Alexander Thorman, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/733,346

(22) PCT Filed: Jan. 14, 2019

(86) PCT No.: PCT/US2019/013470
§ 371 (c)(1),
(2) Date: Jul. 6, 2020

(87) PCT Pub. No.: WO2019/140372
PCT Pub. Date: Jul. 18, 2019

(65) Prior Publication Data
US 2021/0113604 A1  Apr. 22, 2021

Related U.S. Application Data

(60) Provisional application No. 62/664,367, filed on Apr. 30, 2018, provisional application No. 62/616,538, filed on Jan. 12, 2018.

(51) Int. Cl.
*A61K 31/35* (2006.01)
*A61K 31/713* (2006.01)
(Continued)

(52) U.S. Cl.
CPC .......... *A61K 31/713* (2013.01); *A61K 31/655* (2013.01); *A61K 31/7105* (2013.01);
(Continued)

(58) Field of Classification Search
CPC ........................... A61K 31/35; A61K 31/7105
See application file for complete search history.

(56) References Cited

U.S. PATENT DOCUMENTS 6,465,187 B1 * 10/2002 Nilsson .................. A61K 38/13
435/7.1
8,394,382 B2   3/2013 Crocker et al.
(Continued)

FOREIGN PATENT DOCUMENTS

WO    2006108241 A1   10/2006
WO    2016079067 A1   5/2016
(Continued)

OTHER PUBLICATIONS

International Preliminary Report on Patentability received for PCT Application No. PCT/US2019/013468, dated Jul. 23, 2020, 9 pages.
(Continued)

*Primary Examiner* — Carlos A Azpuru
(74) *Attorney, Agent, or Firm* — KDB Firm PLLC

(57) ABSTRACT

The disclosure provides methods of modulating an immune response by inhibiting BFL1, and related methods for treating and preventing diseases and disorders characterized by inflammation, especially neutrophil induced inflammation.

22 Claims, 31 Drawing Sheets

(51) Int. Cl.

| | |
|---|---|
| *A61K 31/7105* | (2006.01) |
| *C07K 16/18* | (2006.01) |
| *C12N 15/113* | (2010.01) |
| *A61K 31/655* | (2006.01) |
| *A61K 9/127* | (2006.01) |
| *B82Y 5/00* | (2011.01) |

(52) U.S. Cl.
CPC ............ *C07K 16/18* (2013.01); *C12N 15/113* (2013.01); *A61K 9/127* (2013.01); *B82Y 5/00* (2013.01); *C12N 2310/14* (2013.01)

(56) References Cited

U.S. PATENT DOCUMENTS

| | | | |
|---|---|---|---|
| 8,524,762 B2 | 9/2013 | Nawrocki et al. | |
| 9,078,823 B2 | 7/2015 | Gunderson et al. | |
| 2003/0199489 A1 | 10/2003 | Wang | |
| 2007/0021448 A1 | 1/2007 | Han et al. | |
| 2009/0069324 A1* | 3/2009 | Reed | A61P 35/00 |
| | | | 514/254.01 |
| 2009/0118135 A1* | 5/2009 | Reed | G01N 33/574 |
| | | | 435/7.92 |
| 2015/0051249 A1* | 2/2015 | Walensky | C07D 277/42 |
| | | | 514/369 |
| 2015/0099796 A1 | 4/2015 | Gunderson | |
| 2016/0166582 A1 | 6/2016 | Lavelin | |
| 2016/0303101 A1* | 10/2016 | Warner | A61K 31/7068 |
| 2018/0265524 A1 | 9/2018 | Walensky et al. | |
| 2019/0216916 A1 | 7/2019 | Hildeman et al. | |

FOREIGN PATENT DOCUMENTS

| | | |
|---|---|---|
| WO | 2017007858 A1 | 1/2017 |
| WO | 2019140370 A1 | 7/2019 |
| WO | 2019140372 A2 | 7/2019 |
| WO | 2021007593 A1 | 1/2021 |

OTHER PUBLICATIONS

International Preliminary Report on Patentability received for PCT Application No. PCT/US2019/013470, dated Jul. 23, 2020, 12 pages.

International Search Report and Written Opinion received for PCT Application No. PCT/US2020/070249, dated Nov. 24, 2020, 12 pages.

International Search Report and Written Opinion received for PCT Application No. PCT/US2019/013468, dated May 23, 2019, 13 pages.

Almanan et al. (May 1, 2017) "Type 1 Regulatory T Cells (Tr1) Homeostasis and Function in Aging", The Journal of Immunology, 198 (Supp 1).

Belkaid et al. (Nov. 19, 2001) "The Role of Interleukin 10 (IL-10) in the Persistence of Leishmania Major in the Skin After Healing and the Therapeutic Potential of Anti-IL-10 Receptor Antibody for Sterile Cure", Journal of Experimental Medicine, 194(10):1497-1506.

Brooks et al. (Mar. 17, 2008) "IL-10 Blockade Facilitates DNA Vaccine Induced T-cell Responses and Enhances Clearance of Persistent Virus Infection", Journal of Experimental Medicine, 205(3):533-541.

Brooks et al. (Oct. 17, 2006) "Interleukin-10 Determines Viral Clearance or Persistence in Vivo", Nature Medicine, 12(11):1301-1309.

Chelvarajan et al. (Apr. 1, 2005) "The Unresponsiveness of Aged Mice to Polysaccharide Antigens is a Result of a Defect in Macrophage Function", Journal of Leukocyte Biology, 77(4):503-512.

Corsini et al. (Aug. 2006) "High Interleukin-10 Production is Associated with Low Antibody Response to Influenza Vaccination in the Elderly", Journal of Leukocyte Biology, 80:376-382.

Dobber et al. (Feb. 1995) "The in Vivo Effects of Neutralizing Antibodies Against IFN-γ, IL-4, or IL-10 on the Humoral Immune Response in Young and Aged Mice", Cellular Immunology, 160(2):185-192.

Hayney et al. (Jan. 2014) "Age and Psychological Influences on Immune Responses to Trivalent Inactivated Influenza Vaccine in the Meditation or Exercise for Preventing Acute Respiratory Infection (MEPARI) Trial", Human Vaccines & Immunotherapeutics, 10(1):83-91.

Janeway Jr. Charles A.(1997) "Immunobiology: The Immune System in Health and Disease", Current Biology Publications, Garland Publications, Inc., 3rd Edition, 3.1-3.11(14 pages).

McKinstry et al. (2009) "IL-10 Deficiency Unleashes an Influenza-Specific Th17 Response and Enhances Survival against High-Dose Challenger1", The Journal of Immunology, 182(12):7353-7363.

Neumann et al. (2014) "Role of BLIMP-1 in Programming Th Effector Cells into IL-10 Producers", Journal of Experimental Medicine, 211(9):1807-1819.

Ni et al. (Aug. 15, 2017) "Blocking IL-10 Signalling at the Time of Immunization Does Not Increase Unwanted Side Effects in Mice", BMC Immunology, 18(40):1-11.

O'Garra et al. (Jun. 2008) "Strategies for Use of IL-10 or its Antagonists in Human Disease", Immunological Reviews, 223(1):114-131.

Pitt et al. (Sep. 12, 2012) "Blockade of IL-10 Signaling during Bacillus Calmette-Guérin Vaccination Enhances and Sustains Th1, Th17, and Innate Lymphoid IFN-γ and IL-17 Responses and Increases Protection to *Mycobacterium tuberculosis* Infection", The Journal of Immunology, 189(8):4079-4087.

Pradhan et al. (Apr. 8, 2014) "The Effect of Combined IL10 siRNA and CpG ODN as Pathogen-Mimicking Microparticles on Th1/Th2 Cytokine Balance in Dendritic Cells and Protective Immunity against B Cell Lymphoma", Biomaterials, 35(21):5491-5504(25 pages).

Pubchem (Mar. 26, 2005) "1-[[3-(Diethylamino)-2-Hydroxypropyl]Amino]-4-Methylthioxanthen-9-One", Pubchem 408723, 1-7 Pages.

Rudikoff et al. (Mar. 1982) "Single Amino Acid Substitution Altering Antigen-Binding Specificity", Proceedings of the National Academy of Sciences, 79(6):1979-1983.

Weinberger Birgit (2018) "Vaccines for the Elderly: Current Use and Future Challenges", Immunity & Ageing, 15(3):1-8.

Xie et al. (Jul. 2017) "Bcl6 Promotes Follicular Helper T-cell Differentiation and PD-1 Expression in a Blimp1-independent Manner in Mice", European Journal of Immunology, 47(7):1136-1141.

Garner et al. (2017) "Progress in Targeting the BCL-2 Family of Proteins", Current Biology LTD, 39:133:142.

Romero, R., J. Espinoza, W.T. Rogers, A. Moser, J.K. Nien, J.P. Kusanovic, F. Gotsch, O. Erez, R. Gomez, S. Edwin, and S.S. Hassan, Proteomic analysis of amniotic fluid to identify women with preterm labor and intra-amniotic inflammation/infection: the use of a novel computational method to analyze mass spectrometric profiling. J Matern Fetal Neonatal Med, 2008. 21: 367-388.

Dulay, A.T., I.A. Buhimschi, G. Zhao, M.O. Bahtiyar, S.F. Thung, M. Cackovic, and C.S. Buhimschi, Compartmentalization of acute phase reactants Interleukin-6, C-Reactive Protein and Procalcitonin as biomarkers of intra-amniotic infection and chorioamnionitis. Cytokine, 2015. 76: 236-243.

Girard, S., L. Tremblay, M. Lepage, and G. Sebire, IL-1 receptor antagonist protects against placental and neurodevelopmental defects induced by maternal inflammation. J Immunol, 2010. 184: 3997-4005.

Nadeau-Vallee, M., C. Quiniou, J. Palacios, X. Hou, A. Erfani, A. Madaan, M. Sanchez, K. Leimert, A. Boudreault, F. Duhamel, J.C. Rivera, T. Zhu, B. Noueihed, S.A. Robertson, X. Ni, D.M. Olson, W. Lubell, S. Girard, and S. Chemtob, Novel Noncompetitive IL-1 Receptor-Biased Ligand Prevents Infection- and Inflammation-Induced Preterm Birth. J Immunol, 2015. 195: 3402-3415.

Fidel, P.L., Jr., R. Romero, J. Cutright, N. Wolf, R. Gomez, H. Araneda, M. Ramirez, and B.H. Yoon, Treatment with the interleukin-I receptor antagonist and soluble tumor necrosis factor receptor Fc fusion protein does not prevent endotoxin-induced preterm parturition in mice. J Soc Gynecol Investig, 1997. 4: 22-26.

(56) References Cited

OTHER PUBLICATIONS

Baggia, S., M.G. Gravett, S.S. Witkin, G.J. Haluska, and M.J. Novy, Interleukin-1 beta intra-amniotic infusion induces tumor necrosis factor-alpha, prostaglandin production, and preterm contractions in pregnant rhesus monkeys. J Soc Gynecol Investig, 1996. 3: 121-126.

Adams Waldorf, K.M., D. Persing, M.J. Novy, D.W. Sadowsky, and M.G. Gravett, Pretreatment with toll-like receptor 4 antagonist inhibits lipopolysaccharide-induced preterm uterine contractility, cytokines, and prostaglandins in rhesus monkeys. Reprod Sci, 2008. 15: 121-127.

Kallapur, S.G., P. Presicce, P. Senthamaraikannan, M. Alvarez, A.F. Tarantal, L.M. Miller, A.H. Jobe, and C.A. Chougnet, Intra-Amniotic IL-1beta Induces Fetal Inflammation in Rhesus Monkeys and Alters the Regulatory T Cell/IL-17 Balance. J Immunol, 2013. 191: 1102-1109.

Leon, L.R., C.A. Conn, M. Glaccum, and M.J. Kluger, IL-1 type I receptor mediates acute phase response to turpentine, but not lipopolysaccharide, in mice. Am J Physiol, 1996. 271: R1668-1675.

Liao, J., V.S. Kapadia, L.S. Brown, N. Cheong, C. Longoria, D. Mija, M. Ramgopal, J. Mirpuri, D C. McCumin, and R.C. Savani, The NLRP3 inflammasome is critically involved in the development of bronchopulmonary dysplasia. Nat Commun, 2015. 6: 8977.

Kallapur, S.G., I. Nitsos, T.J. Moss, G.R. Polglase, J.J. Pillow, F.C. Cheah, B.W. Kramer, J.P. Newnham, M. Ikegami, and A.H. Jobe, IL-1 mediates pulmonary and systemic inflammatory responses to chorioamnionitis induced by lipopolysaccharide. Am J Respir Crit Care Med, 2009. 179: 955-961.

Chandra, Rachna et al. "IRAK1-dependent signaling mediates mortality in polymicrobial sepsis." Inflammation vol. 36,6 (2013): 1503-12. doi:10.1007/s10753-013-9692-1.

Jacob, C.O., et al., Identification of IRAK1 as a risk gene with critical role in the pathogenesis of systemic lupus erythematosus. Proc Natl Acad Sci U S A, 2009. 106: 6256-6261.

Jain, A., S. Kaczanowska, and E. Davila, IL-1 Receptor-Associated Kinase Signaling and Its Role in Inflammation, Cancer Progression, and Therapy Resistance. Front Immunol, 2014. 5: 553.

Rhyasen, G.W., L. Bolanos, J. Fang, A. Jerez, M. Wunderlich, C. Rigolino, L. Mathews, M. Ferrer, N. Southall, R. Guha, J. Keller, C. Thomas, L.J. Beverly, A. Cortelezzi, E.N. Oliva, M. Cuzzola, J.P. Maciejewski, J.C. Mulloy, and D.T. Starczynowski, Targeting IRAK1 as a therapeutic approach for myelodysplastic syndrome. Cancer Cell, 2013. 24: 90-104.

Kallquist, L., M. Hansson, A.M. Persson, H. Janssen, J. Calafat, H. Tapper, and I. Olsson, The tetraspanin CD63 is involved in granule targeting of neutrophil elastase. Blood, 2008. 112: 3444-3454.

Fossati, G., R.J. Moots, R.C. Bucknall, and S.W. Edwards, Differential role of neutrophil Fcgamma receptor IIIB (CD16) in phagocytosis, bacterial killing, and responses to immune complexes. Arthritis Rheum, 2002. 46: 1351-1361.

Luo, H.R. and F. Loison, Constitutive neutrophil apoptosis: mechanisms and regulation. Am J Hematol, 2008. 83: 288-295.

Vier, J., M. Groth, M. Sochalska, and S. Kirschnek, The anti-apoptotic Bcl-2 family protein A1/Bfl-1 regulates neutrophil survival and homeostasis and is controlled via PI3K and JAK/STAT signaling. Cell Death Dis, 2016. 7: e2103.

Rossi, A.G., D.A. Sawatzky, A. Walker, C. Ward, T.A. Sheldrake, N.A. Riley, A. Caldicott, M. Martinez-Losa, T.R. Walker, R. Duffin, M. Gray, E. Crescenzi, M.C. Martin, H.J. Brady, J.S. Savill, I. Dransfield, and C. Haslett, Cyclin-dependent kinase inhibitors enhance the resolution of inflammation by promoting inflammatory cell apoptosis. Nat Med, 2006. 12: 1056-1064.

Koedel, U., T. Frankenberg, S. Kirschnek, B. Obermaier, H. Hacker, R. Paul, and G. Hacker, Apoptosis is essential for neutrophil functional shutdown and determines tissue damage in experimental pneumococcal meningitis. PLoS Pathog, 2009. 5: e1000461.

Hampson, P., J. Hazeldine, and J.M. Lord, Neutrophil apoptosis and its induction as a potential treatment for chronic inflammatory disease. Curr Opin Hematol, 2013. 20: 10-15.

Smith, R., Parturition. N Engl J Med, 2007. 356: 271-283.

Bugl, S., S. Wirths, M.P. Radsak, H. Schild, P. Stein, M.C. Andre, M.R. Muller, E. Malenke, T. Wiesner, M. Marklin, J. S. Frick, R. Handgretinger, H.G. Rammensee, L. Kanz, and H.G. Kopp, Steady-state neutrophil homeostasis is dependent on TLR4/TRIF signaling. Blood, 2013. 121: 723-733.

Clynes, R.A., T.L. Towers, L.G. Presta, and J.V. Ravetch, Inhibitory Fc receptors modulate in vivo cytotoxicity against tumor targets. Nat Med, 2000. 6: 443-446.

Subramaniam, A., A. Abramovici, W.W. Andrews, and A.T. Tita, Antimicrobials for preterm birth prevention: an overview. Infect Dis Obstet Gynecol, 2012. 2012: 157159.

Redline, R.W., O. Faye-Petersen, D. Heller, F. Qureshi, V. Savell, and C. Vogler, Amniotic infection syndrome: nosology and reproducibility of placental reaction patterns. Pediatr Dev Pathol, 2003. 6: 435-448.

Leverson, A New Staple: Peptide-Targeted Covalent Inhibitors, Cell Chemical Biology (2016).

Thorman, Alexander., "Rational Design of Novel BCL2A1 Inhibitors for Treatment of Autoimmune Diseases: An Integration of Virtual Screening, Transcriptomics and Protein Biophysics" A Dissertation submitted to the Graduate School of the University of Cincinnati—2018.

Gautam et al. J. Drug Delivery Sci. Tech. 2017 260-268.

Peer et al. Science 2008 319(5863):627-30.

Bobbin and Rossi Annu Rev. Pharmacol Toxicol 2016 56:103-122.

Extended European Search Report for Application No. 19738033.0, dated Aug. 24, 2021, 9 pages.

Presicce et al., "IL-1 signaling mediates intrauterine inflammation and chorio-decidua netrophil recruitment and activation", JCI Insight, 2018, vol. 3(6), article e98306, pp. 1-16. https://doi.org/10.1172/jci.insight.98306.

Dunn, P.M., Sir George Newman, MD (1870-1948) and the prevention of perinatal disease. Arch Dis Child Fetal Neonatal Ed, 2005. 90: F278-280.

Ledger, W.J., Infection and premature labor. Am J Perinatol, 1989. 6: 234-236.

Martin, J.A., B.E. Hamilton, M.J. Osterman, A.K. Driscoll, and T.J. Mathews, Births: Final Data for 2015. Natl Vital Stat Rep, 2017. 66: 1.

Gravett, M.G., C.E. Rubens, P. Global Alliance to Prevent, and T. Stillbirth Technical, A framework for strategic investments in research to reduce the global burden of preterm birth. Am J Obstet Gynecol, 2012. 207: 368-373.

Liu, L., H.L. Johnson, S. Cousens, J. Perin, S. Scott, J.E. Lawn, I. Rudan, H. Campbell, R. Cibulskis, M. Li, C. Mathers, R.E. Black, W.H.O. Child Health Epidemiology Reference Group of, and Unicef, Global, regional, and national causes of child mortality: an updated systematic analysis for 2010 with time trends since 2000. Lancet, 2012. 379: 2151-2161.

Goldenberg, R.L., J.F. Culhane, J.D. Iams, and R. Romero, Epidemiology and causes of preterm birth. Lancet, 2008. 371: 75-84.

Goldenberg, R.L., J.C. Hauth, and W.W. Andrews, Intrauterine infection and preterm delivery. N Engl J Med, 2000. 342: 1500-1507.

Yoon, B.H., R. Romero, J.H. Lim, S.S. Shim, J.S. Hong, J.Y. Shim, and J.K. Jun, The clinical significance of detecting Ureaplasma urealyticum by the polymerase chain reaction in the amniotic fluid of patients with preterm labor. Am J Obstet Gynecol, 2003. 189: 919-924.

DiGiulio, D.B., R. Romero, H.P. Amogan, J.P. Kusanovic, E.M. Bik, F. Gotsch, C.J. Kim, O. Erez, S. Edwin, and D.A. Relman, Microbial prevalence, diversity and abundance in amniotic fluid during preterm labor: a molecular and culture-based investigation. PLoS One, 2008. 3: e3056.

Wu, Y.W. and J.M. Colford, Jr., Chorioamnionitis as a risk factor for cerebral palsy: A meta-analysis. JAMA, 2000. 284: 1417-1424.

Shatrov, J.G., S.C. Birch, L.T. Lam, J.A. Quinlivan, S. McIntyre, and G.L. Mendz, Chorioamnionitis and cerebral palsy: a meta-analysis. Obstet Gynecol, 2010. 116: 387-392.

Pappas, A., D.E. Kendrick, S. Shankaran, B.J. Stoll, E.F. Bell, A.R. Laptook, M.C. Walsh, A. Das, E.C. Hale, N.S. Newman, R.D. Higgins, H. Eunice Kennedy Shriver National Institute of Child, and N. Human Development Neonatal Research, Chorioamnionitis and

(56) References Cited

OTHER PUBLICATIONS early childhood outcomes among extremely low-gestational-age neonates. JAMA Pediatr, 2014. 168: 137-147.
Been, J.V., S. Lievense, L.J. Zimmermann, B.W. Kramer, and T.G. Wolfs, Chorioamnionitis as a risk factor for necrotizing enterocolitis: a systematic review and meta-analysis. J Pediatr, 2013. 162: 236-242 e232.
Speer, C.P., Inflammation and bronchopulmonary dysplasia: a continuing story. Semin Fetal Neonatal Med, 2006. 11: 354-362.
Redline, R.W., Inflammatory response in acute chorioamnionitis. Semin Fetal Neonatal Med, 2012. 17: 20-25.
Romero, R., S.K. Dey, and S.J. Fisher, Preterm labor: one syndrome, many causes. Science, 2014. 345: 760-765.
Steel, J.H., K. O'Donoghue, N.L. Kennea, M.H. Sullivan, and A.D. Edwards, Maternal origin of inflammatory leukocytes in preterm fetal membranes, shown by fluorescence in situ hybridisation. Placenta, 2005. 26: 672-677.
Sampson, J.E., R.P. Theve, R.N. Blatman, T.D. Shipp, D.W. Bianchi, B.E. Ward, and R.M. Jack, Fetal origin of amniotic fluid polymorphonuclear leukocytes. Am J Obstet Gynecol, 1997. 176: 77-81.
Mantovani, A., M.A. Cassatella, C. Costantini, and S. Jailion, Neutrophils in the activation and regulation of innate and adaptive immunity. Nat Rev Immunol, 2011. 11: 519-531.
Rinaldi, S.F., R.D. Catalano, J. Wade, A.G. Rossi, and J.E. Norman, Decidual Neutrophil Infiltration Is Not Required for Preterm Birth in a Mouse Model of Infection-Induced Preterm Labor. J Immunol, 2014. 192.
Filipovich, Y., V. Agrawal, S.E. Crawford, P. Fitchev, X. Qu, J. Klein, and E. Hirsch, Depletion of polymorphonuclear leukocytes has no effect on preterm delivery in a mouse model of *Escherichia coli*-induced labor. Am J Obstet Gynecol, 2015. 213: 697 e691-697 e610.
Hamilton, S.A., C.L. Tower, and R.L. Jones, Identification of chemokines associated with the recruitment of decidual leukocytes in human labour: potential novel targets for preterm labour. PLoS One, 2013. 8: e56946.
Presicce, P., P. Senthamaraikannan, M. Alvarez, C.M. Rueda, M. Cappelletti, L.A. Miller, A.H. Jobe, C.A. Chougnet, and S.G. Kallapur, Neutrophil recruitment and activation in decidua with intra-amniotic IL-1beta in the preterm rhesus macaque. Biol Reprod, 2015. 92: 56.
Gomez-Lopez, N., D. StLouis, M.A. Lehr, E.N. Sanchez-Rodriguez, and M. Arenas-Hernandez, Immune cells in term and preterm labor. Cell Mol Immunol, 2014.
Sadowsky, D.W., K.M. Adams, M.G. Gravett, S.S. Witkin, and M.J. Novy, Preterm labor is induced by intraamniotic infusions of interleukin-1beta and tumor necrosis factor-alpha but not by interleukin-6 or interleukin-8 in a nonhuman primate model. Am J Obstet Gynecol, 2006. 195: 1578-1589.
Sadowsky, D.W., G.J. Haluska, M.G. Gravett, S.S. Witkin, and M.J. Novy, Indomethacin blocks interleukin 1beta-induced myometrial contractions in pregnant rhesus monkeys. Am J Obstet Gynecol, 2000. 183: 173-180.
Sadowsky, D.W., M.J. Novy, S.S. Witkin, and M.G. Gravett, Dexamethasone or interleukin-10 blocks interleukin-1beta-induced uterine contractions in pregnant rhesus monkeys. Am J Obstet Gynecol, 2003. 188: 252-263.
Romero, R., M. Mazor, and B. Tartakovsky, Systemic administration of interleukin-1 induces preterm parturition in mice. Am J Obstet Gynecol, 1991. 165: 969-971.
Hirsch, E., Y. Filipovich, and M. Mahendroo, Signaling via the type I IL-1 and TNF receptors is necessary for bacterially induced preterm labor in a murine model. Am J Obstet Gynecol, 2006. 194: 1334-1340.
Kim, J., K. Zhao, P. Jiang, Z.X. Lu, J. Wang, J.C. Murray, and Y. Xing, Transcriptome landscape of the human placenta. BMC Genomics, 2012. 13: 115.
Dolan, S.M., M.V. Hollegaard, M. Merialdi, A.P. Betran, T. Allen, C. Abelow, J. Nace, B.K. Lin, M.J. Khoury, J.P. Ioannidis, S. Bagade, X. Zheng, R.A. Dubin, L. Bertram, D.R. Velez Edwards, and R. Menon, Synopsis of preterm birth genetic association studies: the preterm birth genetics knowledge base (PTBGene). Public Health Genomics, 2010. 13: 514-523.
The Preterm Birth Genetics Knowledge Base, http://bioinformatics.aecom.yu.edu/ptbgene/index.html.
Guzeloglu-Kayisli, O., U.A. Kayisli, N. Semerci, M. Basar, L.F. Buchwalder, C.S. Buhimschi, I.A. Buhimschi, F. Arcuri, K. Larsen, J.S. Huang, F. Schatz, and C.J. Lockwood, Mechanisms of chorioamnionitis-associated preterm birth: interleukin-1beta inhibits progesterone receptor expression in decidual cells. J Pathol, 2015.
Gravett, M.G., G.J. Haluska, M.J. Cook, and M.J. Novy, Fetal and maternal endocrine responses to experimental intrauterine infection in rhesus monkeys. Am J Obstet Gynecol, 1996. 174: 1725-1731; discussion 1731-1723.
Golos, T.G., G.I. Bondarenko, S.V. Dambaeva, E.E. Breburda, and M. Durning, On the role of placental Major Histocompatibility Complex and decidual leukocytes in implantation and pregnancy success using non-human primate models. Int J Dev Biol, 2010. 54: 431-443.
Rueda, C.M., P. Presicce, C.M. Jackson, L.A. Miller, S.G. Kallapur, A.H. Jobe, and C.A. Chougnet, Lipopolysaccharide-Induced Chorioamnionitis Promotes IL-1-Dependent Inflammatory FOXP3+ CD4+ T Cells in the Fetal Rhesus Macaque. J Immunol, 2016. 196: 3706-3715.
Dinarello, C.A., Blocking IL-1 in systemic inflammation. J Exp Med, 2005. 201: 1355-1359.
Rider, P., Y. Carmi, O. Guttman, A. Braiman, I. Cohen, E. Voronov, M.R. White, C.A. Dinarello, and R.N. Apte, IL-1alpha and IL-1beta recruit different myeloid cells and promote different stages of sterile inflammation. J Immunol, 2011. 187: 4835-4843.
Aksentijevich, I., S.L. et al., An autoinflammatory disease with deficiency of the interleukin-1-receptor antagonist. N Engl J Med, 2009. 360: 2426-2437.
Goldbach-Mansky, R., et al., Neonatal-onset multisystem inflammatory disease responsive to interleukin-1beta inhibition. N Engl J Med, 2006. 355: 581-592.
Fox, E., N. Jayaprakash, T.H. Pham, A. Rowley, C.L. McCully, F. Pucino, and R. Goldbach-Mansky, The serum and cerebrospinal fluid pharmacokinetics of anakinra after intravenous administration to non-human primates. J Neuroimmunol, 2010. 223: 138-140.
Gottipati, S., N.L. Rao, and W.P. Fung-Leung, IRAK1: a critical signaling mediator of innate immunity. Cell Signal, 2008. 20: 269-276.
Berberich, I. and D.A. Hildeman, The Bcl2a1 gene cluster finally knocked out: first clues to understanding the enigmatic role of the Bcl-2 protein A1. Cell Death Differ, 2017. 24: 572-574.
Bittker, J.A., M. Weiwer, G. Wei, A. Germain, E. Brown, S. Dandapani, B. Munoz, M. Palmer, T. Golub, and S.L. Schreiber, Discovery of Inhibitors of Anti-Apoptotic Protein A1, in Probe Reports from the NIH Molecular Libraries Program. 2010: Bethesda (MD).
Vogler, M., M. Butterworth, A. Majid, R.J. Walewska, X.M. Sun, M.J. Dyer, and G.M. Cohen, Concurrent up-regulation of BCL-XL and BCL2A1 induces approximately 1000-fold resistance to ABT-737 in chronic lymphocytic leukemia. Blood, 2009. 113: 4403-4413.
Combs, C.A., M. Gravett, T.J. Garite, D.E. Hickok, J. Lapidus, R. Porreco, J. Rael, T. Grove, T.K. Morgan, W. Clewell, H. Miller, D. Luthy, L. Pereira, M. Nageotte, P.A. Robilio, S. Fortunato, H. Simhan, J.K. Baxter, E. Amon, A. Franco, K. Trofatter, K. Heyborne, and N. ProteoGenix/Obstetrix Collaborative Research, Amniotic fluid infection, inflammation, and colonization in preterm labor with intact membranes. Am J Obstet Gynecol, 2014. 210: 125 e121-125 e115.
Romero, R., J. Miranda, T. Chaiworapongsa, S.J. Korzeniewski, P. Chaemsaithong, F. Gotsch, Z. Dong, A.I. Ahmed, B.H. Yoon, S.S. Hassan, C.J. Kim, and L. Yeo, Prevalence and Clinical Significance of Sterile Intra-amniotic Inflammation in Patients with Preterm Labor and Intact Membranes. Am J Reprod Immunol, 2014. 72: 458-474.

(56) References Cited

OTHER PUBLICATIONS

Romero, R., J.C. Grivel, A.L. Tarca, P. Chaemsaithong, Z. Xu, W. Fitzgerald, S.S. Hassan, T. Chaiworapongsa, and L. Margolis, Evidence of perturbations of the cytokine network in preterm labor. Am J Obstet Gynecol, 2015. 213: 836 e831-836 e818.

Knox, I.C., Jr. and J.K. Hoerner, The role of infection in premature rupture of the membranes. Am J Obstet Gynecol, 1950. 59: 190-194, illust.

International Search Report and Written Opinion of the International Searching Authority dated Aug. 16, 2019 for International Application No. PCT/US2019/013470, filed Jan. 14, 2019 (20 pages).

\* cited by examiner

FIG. 15A
FIG. 15B
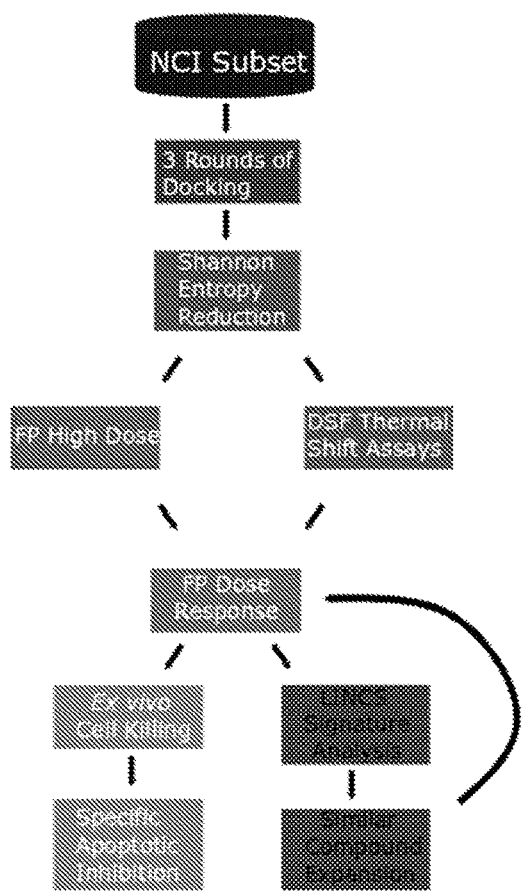
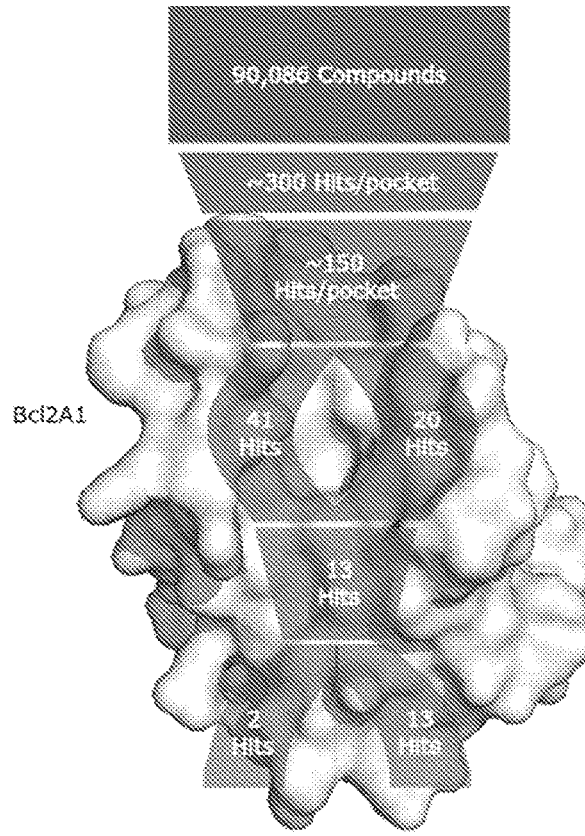
Functional Compound "As is"  *in vitro* effective, expand with Genomic Data

FIG. 20

| | [45195] (µM) | | | | | | |
|---|---|---|---|---|---|---|---|
| | 200 | 100 | 50 | 25 | 12.5 | 6.25 | 0 |
| [97318] (µM) 200 | 66 | 60 | 58 | 58 | 56 | 57 | 57 |
| 100 | 64 | 59 | 55 | 55 | 54 | 60 | 63 |
| 50 | 64 | 58 | 53 | 62 | 63 | 69 | 73 |
| 25 | 72 | 55 | 51 | 64 | 88 | 108 | 113 |
| 12.5 | 67 | 56 | 54 | 74 | 119 | 126 | 129 |
| 6.25 | 63 | 51 | 56 | 114 | 132 | 135 | 139 |
| 0 | 70 | 53 | 81 | 127 | 145 | 146 | 154 |
| Noxa Alone | 67 | | | | | | |
| A1 + Noxa | 155 | | | | | | |

[45195] (μM)

[97318] (uM)

METHODS OF ATTENUATING AN IMMUNE RESPONSE BY INHIBITION OF BFL1

CROSS REFERENCE TO RELATED APPLICATIONS

This application is a national stage entry, filed under 35 U.S.C. § 371, of International Application No. PCT/US2019/013470, filed on Jan. 14, 2019, which claims the benefit of U.S. Provisional application No. 62/616,538, filed Jan. 12, 2018 and 62/664,367 filed Apr. 30, 2018, the entire disclosures of which are hereby incorporated by reference in their entirety.

STATEMENT REGARDING FEDERALLY-SPONSORED RESEARCH

This invention was made with government support under R21HD090856 awarded by the National Institutes of Health. The U.S. Government has certain rights in the invention.

FIELD OF THE INVENTION

The disclosure provides methods of modulating an immune response by inhibiting BFL1, and related methods for treating and preventing diseases and disorders characterized by excessive inflammation.

BACKGROUND

Intrauterine infection and inflammation (IUI) is associated with about 40% of premature deliveries and also increases the risk for fetal and newborn brain injury, necrotizing enterocolitis, and chronic lung disease. The histologic correlate of IUI is chorioamnionitis, defined as neutrophil infiltration of maternal-fetal membranes and the placenta (Redline et al., 2012). The products of inflammation during IUI are strongly implicated as causative agents of prematurity (Romero et al., 2014). Neutrophil infiltration at the maternal-fetal interface occurs in the chorio-decidua, amniotic fluid, and fetal tissues, but neutrophils in the chorio-decidua are largely of maternal origin while those in the amniotic fluid are largely of fetal origin. The mechanisms whereby neutrophils accumulate in the different maternal-fetal niches are poorly understood. While activated tissue neutrophils are known to survive longer compared to blood neutrophils, the mechanisms underlying survival of neutrophils at the maternal-fetal interface, particularly during IUI, are not known, and the question of the importance of neutrophils as regulators of maternal-fetal inflammation and preterm labor is not settled (Rinaldi et al., 2014; Filipovich et al., 2015; Hamilton et al., 2013; Presicce et al., 2015; Gomez-Lopez et al, 2014).

Interleukin 1 ("IL-1") signaling has been implicated in the pathogenesis of IUI mediated pre-term labor in the lipopolysaccharide ("LPS")-induced chorioamnionitis Rhesus monkey model system as well as in mouse models and in humans (Rueda et al. 2016; Kim et al., 2012; Dolan et al., 2010) and IL-1 inhibitors have experimentally prevented infection and inflammation induced preterm birth in mice (Nadeau-Vallee et al. 2015).

Members of the BCL2 family of proteins are related through homology of their BCL2 homology (BH) domains. The proteins of this family may be divided into three main classes based on their activity in relation to cellular apoptosis: 1) anti-apoptotic or pro-survival factors; 2) pro-apoptotic activators or cytotoxic agents; and 3) pro-apoptotic sensitizers or effectors. Upon stress signaling, cells undergo apoptosis via mitochondrial outer membrane permeabilization (MOMP), which is driven by pro-apoptotic BCL2 family members. The pro-apoptotic BCL2 proteins are comprised of BH3-only proteins, such as NOXA, PUMA, and BIM that serve as sensitizers, and the multi-domain proteins, BAX and BAK that function as cytotoxic agents, promoting apoptosis. The BH3-only peptides either directly (through physical interaction) or indirectly (through interaction with anti-apoptotic Bcl-2 family members) activate BAX and BAK to promote mitochondrial membrane permeabilization and are upregulated during times of cell stress.

Pro-survival BCL2 proteins function through either prevention of BAX/BAK activity or sequestration of BH3-only activator proteins, resulting in inactive BAX/BAK. The pro-survival BCL2 family proteins sequester the pro-apoptotic members, driving a pro-survival phenotype and blocking MOMP. A number of family members have been described with varying targets and cell types in which they are present, including BCL2, Bcl-$X_L$, Bcl-w, MCL1, BCL-B and BCL2A1.

BFL1 is the human ortholog of murine BCL2A1. The two proteins share 72% amino acid sequence identity. BFL1/BCL2A1 functions as a regulator of T-cell and neutrophil maturation and of the maintenance of $CD4^+$ T-cells. Knock-out mice for all isoforms demonstrate decreased total $CD4^+$ T cells, regulatory T-cells, and conventional dendritic cells in the spleen, but have an otherwise benign phenotype.

SUMMARY

The present invention is based, in part, on the unexpected discovery that BCL2A1/BFL1 is a critical promoter of neutrophil survival at the maternal-fetal interface during chorioamnionitis. This discovery implicates BCL2A1/BFL1 as a therapeutic target in the prophylaxis and treatment of diseases and disorders characterized by excessive inflammation, particularly neutrophil-mediated inflammation, and in the treatment of cancers overexpressing BCL2A1/BFL1. Accordingly, the present disclosure provides methods for attenuating an immune response, methods for treating an autoimmune disease or allergic disorder characterized by neutrophil-mediated inflammation, methods for the prevention of pre-term birth and the treatment of chorioamnionitis, and methods for the treatment of cancer, in a subject in need thereof, the methods comprising administering to the subject an inhibitor of BFL1.

In embodiments, the autoimmune disease or allergic disorder is selected from anaphylaxis, asthma, atopic dermatitis, cystic fibrosis, irritable bowel syndrome (IBD), lupus erythematosus, psoriasis, and rheumatoid arthritis.

In embodiments, the cancer is selected from adrenocortical carcinoma (ACC), acute myeloid leukemia (AML), bladder cancer, breast cancer, cervical cancer, cholangiocarcinoma, colorectal cancer, diffuse large B-cell (DLBC) lymphoma, glioblastoma multiforme (GBM), glioma, head and neck cancer, liver cancer, lung cancer, melanoma, mesothelioma, ovarian cancer, pheochromocytoma and paraganglioma (PCPG), pancreatic cancer, prostate cancer, sarcoma, testicular germ cell cancer, thymoma, thyroid cancer, uterine cancer, uveal melanoma, clear cell renal cell carcinoma (ccRCC), chromophobe renal cell carcinoma (chRCC), and papillary renal cell carcinoma (pRCC). In some embodiments, the cancer is selected from acute myeloid leukemia (AML), breast cancer, diffuse large B-cell lymphoma (DLBCL), head and neck cancer, lung cancer, melanoma, mesothelioma, ovarian cancer, pancreatic cancer, testicular germ cell cancer, thymoma, uterine cancer, clear cell renal cell carcinoma (ccRCC), chromophobe renal cell carcinoma (chRCC), and papillary renal cell carcinoma (pRCC).

In some embodiments, the inhibitor is a single or double stranded RNA interference-based agent (RNAi) targeted to inhibit the expression of the BFL1 gene. In embodiments, the inhibitor is selected from a microRNA, a short hairpin RNA, or a short interfering RNA. In embodiments, the inhibitor is a short interfering RNA ("siRNA"). In embodiments, the siRNA molecule is conjugated to a targeting moiety, or wherein the siRNA molecule is encapsulated within a liposome-based nanoparticle comprising the targeting moiety, and the targeting moiety is selected from a polypeptide or an antibody, or antigen-binding fragment thereof, that binds to a neutrophil-specific cell surface glycoprotein, preferably selected from CD177, CD66b, SIRPa, and SIGLEC9. In embodiments, the inhibitor is a small organic molecule, peptide, polypeptide, or antibody that binds to BFL1, preferably to the P2 or P4 pocket, or both, of the BH3 domain of BFL1. In some embodiments, the small organic molecule is optionally encapsulated within a liposome-based nanoparticle comprising the targeting moiety, and the targeting moiety is selected from a polypeptide or an antibody, or antigen-binding fragment thereof, that binds to a neutrophil-specific cell surface glycoprotein, preferably selected from CD177, CD66b, SIRPa, and SIGLEC9.

In embodiments, the inhibitor is an anti-BFL1 antibody, or a peptide or polypeptide BFL1-binding fragment thereof. In embodiments, the inhibitor is a human or humanized anti-BFL1 monoclonal antibody, or a peptide or polypeptide BFL1-binding fragment thereof.

In embodiments, the inhibitor is a derivative of a compound of Formula I, Ia, Ib, Ic, or Id in which the azo bond is reduced to an azine bond or replaced with a sulfonamide, thioether, or sulfone linker, or an isosteric alkene or alkane bond, optionally encapsulated within a liposome-based nanoparticle comprising the targeting moiety, and the targeting moiety is selected from a polypeptide or an antibody, or antigen-binding fragment thereof, that binds to a neutrophil-specific cell surface glycoprotein, preferably selected from CD177, CD66b, SIRPa, and SIGLEC9. In embodiments, the derivative further comprises the modification of a sulfonate group, if present, to a sulfone group In embodiments, the inhibitor is a derivative of a compound of Formula Ie or If in which each of the azo bonds is reduced to an azine bond or replaced with a sulfonamide, thioether, or sulfone linker, or an isosteric alkene or alkane bond, optionally encapsulated within a liposome-based nanoparticle comprising the targeting moiety, and the targeting moiety is selected from a polypeptide or an antibody, or antigen-binding fragment thereof, that binds to a neutrophil-specific cell surface glycoprotein, preferably selected from CD177, CD66b, SIRPa, and SIGLEC9. In embodiments, the derivative further comprises the modification of a sulfonate group, if present, to a sulfone group.

In embodiments, the inhibitor is the compound designated 1.001 in Table 1, or a derivative thereof. In embodiments, the derivative is a compound in which the azo bond is reduced to an azine bond or replaced with a sulfonamide, thioether, or sulfone linker, or an isosteric alkene or alkane bond. In embodiments, the derivative further comprises the modification of the sulfonate group to a sulfone group.

In accordance with any of the foregoing embodiments, the subject may be a human subject.

In some embodiments, the subject in need is one whose disease or disorder is characterized by inflammation, particularly neutrophil-mediated inflammation, or whose cancer is characterized by overexpression of BFL1.

In embodiments, the method comprises administering two BFL1 inhibitors to the subject, wherein each of the BFL1 inhibitors binds to a different region of BFL1. In embodiments, one of the inhibitors binds to the P4 pocket of BFL1 and the other binds to the P2 pocket of BFL1.

In accordance with any of the foregoing embodiments, the BFL1 inhibitor is encapsulated in a liposome-based nanoparticle comprising a targeting moiety selected from a polypeptide or an antibody, or antigen-binding fragment thereof, that binds to a neutrophil-specific cell surface glycoprotein, preferably selected from CD177, CD66b, SIRPa, and SIGLEC9.

BRIEF DESCRIPTION OF THE DRAWINGS

FIGS. 15A-B: Overall process scheme for structure-informed identification of potential inhibitors of BCL2A1. The overall strategy (A) and the results from each stage in the process (B) are provided.

FIG. 20: Checkerboard assays show additivity between P2 and P4 inhibitors. NSC-97318 and NSC-45195 were tested for additivity across a wide range of concentrations and demonstrated a low level additivity for inhibition of A1-Noxa binding. Polarization values (mP) are displayed upon titration of a P2 (97318) and a P4 (45195) inhibitor. Values in Blue are those above the $IC_{50}$ threshold and those in red are at the completely unbound state.

DETAILED DESCRIPTION

Figure 1A:
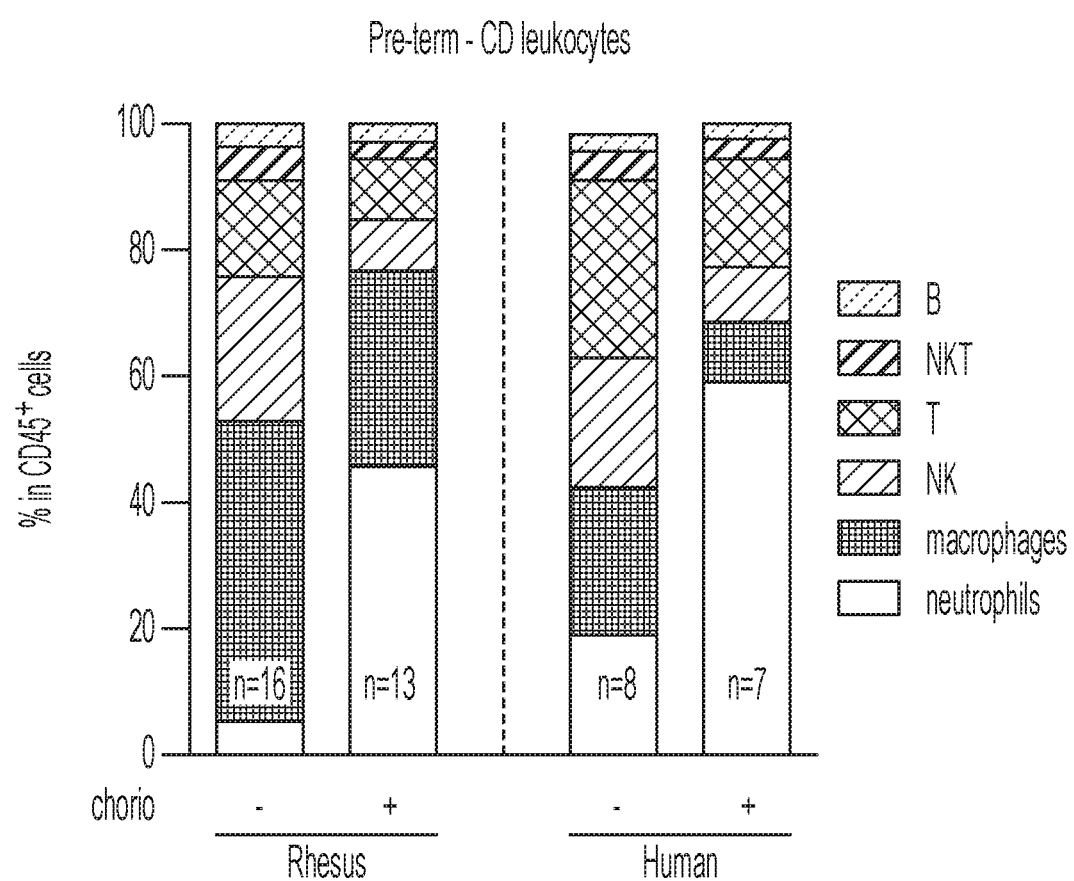
FIGS. 1A-C: The cellular and molecular characteristics of inflammation in the LPS-induced chorioamnionitis Rhesus monkey model and human chorioamnionitis. (A) Percentage of CD45+ cells and cell type in chorioamnionitis negative versus chorioamnionitis positive groups in both monkey and human (rhesus chorio neg., n=16; rhesus chorio pos., n=13; human chorio neg., n=8; human chorio pos., n=7). Data are mean±SEM, *P<0.05 between comparators by Mann-Whitney test. (B) Representative fetal membrane (chorioamnion-decidua, CAD; n=5) H&E histology. Neutrophil infiltration at the chorio-decidua interface (white arrowheads) (am, amnion; ch, cho-rion; dp, decidua parietalis). (C) Expression of mRNA by quantitative PCR (Taqman probes) in the fetal membranes during chorioamnionitis in Rhesus (filled bars) chorio pos., n=4-10 and human (open bars) chorio pos., n=4-11). Average mRNA values are fold increases over the average value for control or no chorio (dashed line) after internally normalizing to the housekeeping 18S RNA.

The present disclosure provides methods for modulating an immune response by inhibiting BCL2A1/BFL1. The murine (BCL2A1) and human (BFL1) proteins are highly conserved, particularly in their BH3 binding domain, or "BH3 groove", as discussed in more detail infra. Accordingly, the proteins are referred to interchangeably herein, with respect to inhibition thereof, although inhibitors targeted to the human protein BFL1 are preferred.

The methods described here include the prevention of pre-term birth and the treatment of chorioamnionitis by inhibition of BCL2A1/BFL1, or more specifically through the inhibition of the human ortholog BFL1. As described more fully infra, the present inventors have found that BCL2A1/BFL1 promotes the survival of pro-inflammatory neutrophils during chorioamnionitis. This pro-survival function in relation to inflammatory neutrophils indicates its feasibility as a target in the treatment of other diseases and disorders characterized by excessive neutrophil-mediated inflammation. Accordingly, the disclosure further provides methods and exemplary compounds for treating diseases and disorders characterized by excessive inflammation, particularly neutrophil-mediated inflammation, by inhibiting BFL1. In embodiments, the diseases and disorders characterized by excessive inflammation is an autoimmune disease or allergic disorder. In embodiments, the autoimmune disease or allergic disorder is selected from anaphylaxis, asthma, atopic dermatitis, cystic fibrosis, irritable bowel syndrome (IBD), including more specifically one or both of Crohn's disease and ulcerative colitis, lupus erythematosus, psoriasis, and rheumatoid arthritis.

It is well-established that cancer cells can circumvent mitochondrial apoptosis by overexpressing BCL-2 family pro-survival proteins, such as BCL-2 and MCL-1. BCL-2 family pro-survival proteins as a group prevent apoptosis by sequestering pro-apoptosis family members in a groove on the surface of the protein, referred to herein as the "BH3 groove". This groove binds to the BCL-2 homology 3 ("BH3") domain helix of the pro-apoptotic family members, thereby sequestering them and promoting cell survival. Small molecule and peptide mimetics of the BH3 helix that bind this groove have been demonstrated to be able to reactivate apoptosis and inhibitors of BCL-2 family pro-survival proteins have shown promise as anti-cancer agents. For example, a number of therapeutic agents have targeted BCL2-family proteins with varying degrees of success, most notably ABT-737, ABT-263, ML214 and ABT-199 (venetoclax). ABT-737, ABT-263 (navitoclax) and ML214 target the BCL2-family broadly, inhibiting BCL-2, BCL-xL, and BCL-W. ABT-199 is a more targeted therapeutic that specifically inhibits BCL-2, but not other family members. To date, no specific inhibitors of BFL1 have been identified.

Accordingly, the disclosure further provides compounds that interact with the BH3 groove of BCL2A1/BFL1, and related methods of treating cancer using same.

In embodiments, the disclosure provides methods of treating a cancer in a subject in need thereof, the methods comprising administering to the subject a BCL2A1/BFL1 inhibitor. In embodiments, the cancer is selected from adrenocortical carcinoma (ACC), acute myeloid leukemia (AML), bladder cancer, breast cancer, cervical cancer, cholangiocarcinoma, colorectal cancer, diffuse large B-cell lymphoma (DLBC or DLBCL, a type of Non-Hodgkins lymphoma), glioblastoma multiforme (GBM), glioma, head and neck cancer liver cancer, lung cancer, melanoma, mesothelioma, ovarian cancer, pheochromocytoma and paraganglioma (PCPG), pancreatic cancer, prostate cancer, sarcoma, testicular germ cell cancer, thymoma, thyroid cancer, uterine cancer, uveal melanoma, clear cell renal cell carcinoma (ccRCC), chromophobe renal cell carcinoma (chRCC), and papillary renal cell carcinoma (pRCC).

In embodiments, the disclosure also provides methods that encompass administering two BCL2A1/BFL1 inhibitors, preferably one inhibitor that binds to the P2 pocket of BFL1 and a second inhibitor that binds to the P4 pocket of BFL1.

In embodiments, the BCL2A1/BFL1 inhibitor is targeted for delivery to activated tissue neutrophils. Targeted delivery systems that may be used include nanoparticles comprised of various materials, for example liposomes, polymers, dendrimers, and magnetic nanoparticles. Nanoparticulate delivery systems suitable for targeting a BCL2A1/BFL1 inhibitor to activated tissue neutrophils include liposome based nanoparticles such as those described in Gautam et al J. Drug Delivery Sci. Tech. 2017 260-268 and Peer et al. Science 2008 319(5863):627-30. For example, the liposome-based nanoparticles may comprise nanoparticular sized (50-500 nm diameter) liposomes formed from neutral phopholipids comprising a glycosaminoglycan such as hyaluronan to which a targeting moiety is attached. In embodiments, the liposomes are loaded with a BCL2A1/BFL1 inhibitor selected from a small organic molecule and an RNAi agent, for example an anti-BFL1 siRNA. In embodiments, the targeting moiety is selected from a polypeptide or an antibody, or antigen-binding fragment thereof, that binds to a neutrophil-specific cell surface glycoprotein. In embodiments, the neutrophil-specific cell surface glycoprotein is selected from a cluster of differentiation ("CD") protein including CD177 and CD66b, signal regulatory protein alpha ("SIRPa"), and sialic acid-binding Ig-like lectin 9 (SIGLEC9). In some embodiments, the targeting moiety may be an antibody or antigen binding fragment thereof that targets proteinase 3 ("PRTN3").

In the context of the methods described here, the term "treating" may refer to the amelioration or stabilization of one or more symptoms associated with the disease, disorder or condition being treated. The term "treating" may also encompass the management of disease, disorder or condition, referring to the beneficial effects that a subject derives from a therapy but which does not result in a cure of the underlying disease, disorder, or condition. In the context of the present disclosure, the term "prevention" refers to preventing the recurrence, development, progression or onset of one or more symptoms of the disease, disorder, or condition.

In embodiments where a therapeutically effective amount of a compound or composition is administered to a subject, the therapeutically effective amount is the amount sufficient to achieve a desired therapeutic outcome, for example the amelioration or stabilization of one or more symptoms of the disease, disorder or condition being treated, or in the context of prevention, the amount sufficient to achieve prevention of the recurrence, development, progression or onset of one or more symptoms of the disease, disorder, or condition.

In embodiments, a therapeutically effective amount is the amount required to achieve at least an equivalent therapeutic effect compared to a standard therapy. An example of a standard therapy is an FDA-approved drug indicated for treating the same disease, disorder or condition.

In the context of any of the methods described here, the subject is preferably a human but may be a non-human vertebrate. In other embodiments, the non-human vertebrate may be, for example, a dog, cat, a rodent (e.g., a mouse, a rat, a rabbit), a horse, a cow, a sheep, a goat, a chicken, a duck, or any other non-human vertebrate.

In embodiments, the human subject is selected from an adult human, a pediatric human, or a geriatric human, as those terms are understood by the medical practitioner, for example as defined by the U.S. Food and Drug Administration.

BCL2A1/BFL1 Inhibitors

The disclosure provides methods for treating diseases and disorders amenable to treatment by inhibition of BCL2A1/BFL1. In embodiments, the inhibitor may be a small organic molecule, a peptide, a polypeptide, a polynucleotide, or an antibody, for example an anti-BFL1 antibody. In embodiments, the antibody is a monoclonal antibody, preferably a human or humanized monoclonal antibody.

In some embodiments, the inhibitor of BCL2A1/BFL1 is a small organic molecule, a peptide, a polypeptide, or an antibody, that binds to the "P4" pocket of BCL2A1/BFL1. All BCL2 family pro-survival proteins contain a conserved hydrophobic pocket, referred to as the "P2" pocket, of the BH3-binding groove (also referred to herein as the "BH3 binding domain") of the protein. In the case of BCL2A1/BFL1, the BH3-binding groove extends into a broad, shallow pocket, which is not present in other family members. This pocket therefore provides a unique surface for identifying and/or targeting small molecules with BCL2A1/BFL1 binding specificity, referred to herein as the "P4" pocket and described more fully in Example 2 and related drawings. The disclosure provides ten exemplary compounds that bind specifically to the P4 pocket of BCL2-A1/BFL1 and two compounds that bind to the P2 pocket. The disclosure further provides that compounds which bind to the P4 pocket may be used in combination with compounds that bind to the P2 pocket as inhibitors of BCL2A1/BFL1.

In embodiments, the inhibitor is a direct BFL1 inhibitor. In this context, the direct inhibitor may be one that binds directly to the BH3 binding domain of BCL2A1/BFL1, for example in the P2 pocket or the P4 pocket of the BH3 binding domain; or one that binds to another region of the BCL2A1/BFL1 but nevertheless inhibits the interaction of the BH3 binding domain with its target proteins, e.g., through steric hindrance or through an allosteric interaction. For example, the agent may be a small organic molecule that binds to the P2 or P4 pocket, as described in more detail below, or an anti-BFL1 antibody, peptide, or polypeptide that binds to the P4 pocket or the P2 pocket, or one that binds to both pockets. Alternatively, the agent may not directly bind the P2 or P4 pocket, but may bind another region of BCL2A1/BFL1 and thereby allosterically inhibit the interaction of the BH binding domain with its target proteins, for example by changing the confirmation or shape of the domain.

In embodiments, an inhibitor for use in the methods described here binds to BFL1 and does not interact substantially with other human BCL-2 family proteins. In some embodiments, the inhibitor does not bind to IL-1 and is not an IL-1 inhibitor.

Antibodies, Peptides, and Polypeptides

In embodiments, the BCL2A1/BFL inhibitor for use in the methods described here is an antibody, peptide, or polypeptide that binds to the murine BCL2A1 protein or the human BFL protein such that the ability of BCL2A1/BFL to bind and sequester its target proteins is blocked or diminished, as described above. Briefly, an inhibitory antibody, peptide, or polypeptide preferably bind to the P2 or P4 pocket of BCL2A1/BFL, or both, and thereby prevent the interaction of the BCL2A1/BFL BH3 binding domain with its target proteins. Alternatively the inhibitory antibody, peptide, or polypeptide may bind allosterically to another region of the BCL2A1/BFL and inhibit its interaction with its target proteins through a conformational change of the BH3 binding domain.

The antibodies for use in the methods described here are preferably monoclonal antibodies, most preferably fully human antibodies, humanized antibodies, camelised antibodies, chimeric antibodies, CDR-grafted antibodies, single-chain Fvs (scFv), disulfide-linked Fvs (sdFv), Fab fragments, F(ab') fragments, or antigen-binding fragments of any of the foregoing. The antigen-binding fragments are fragments of the immunoglobulin molecules that contain a BCL2A1/BFL binding site. Fab, Fab', F(ab')2 and Fv fragments lack the heavy chain constant fragment (Fc) of an intact antibody and may be preferable over an intact antibody due to their rapid clearance from the systemic circulation and fewer off-target effects. Such fragments are produced from intact antibodies using methods well known in the art, for example by proteolytic cleavage with enzymes such as papain (to produce Fab fragments) or pepsin (to produce F(ab')2 fragments). In embodiments, the antigen-binding fragment is a dimer of heavy chains (a camelised antibody), a single-chain Fvs (scFv), a disulfide-linked Fvs (sdFv), a Fab fragment, or a F(ab') fragment. Such fragments may also be fused to another immunoglobulin domain including, but not limited to, an Fc region or fragment thereof. The skilled person will appreciate that other fusion products may be generated, including but not limited to, scFv-Fc fusions, variable region (e.g., VL and VH)-Fc fusions, and scFv-scFv-Fc fusions. Immunoglobulin molecules can be of any type, including, IgG, IgE, IgM, IgD, IgA and IgY, and of any class, including $IgG_1$, $IgG_2$, $IgG_3$, $IgG_4$, $IgA_1$ and $IgA_2$), or of any subclass.

As noted above, the antibodies for use in the methods described here are preferably monoclonal antibodies. A monoclonal antibody is derived from a substantially homogeneous population of antibodies specific to a particular antigen, which population contains substantially similar epitope binding sites. Such antibodies may be of any immunoglobulin class including IgG, IgM, IgE, IgA, and any subclass thereof. Methods for monoclonal antibody production are well known in the art. Preferably, a monoclonal antibody for use in the methods and compositions of the invention is produced using hybridoma technology.

A human antibody is one in which all of the sequences arise from human genes. Human antibodies include antibodies having the amino acid sequence of a human immunoglobulin and include antibodies isolated from human immunoglobulin libraries or from mice that express antibodies from human genes.

A humanized antibody is one which comprises a framework region having substantially the same amino acid sequence as a human receptor immunoglobulin and a complementarity determining region ("CDR") having substantially the same amino acid sequence as a non-human donor immunoglobulin. A humanized antibody comprises substantially all of at least one, and typically two, variable domains (Fab, Fab', F(ab')$_2$, Fv) in which all or substantially all of the CDR regions correspond to those of the non-human donor immunoglobulin (i.e., the donor antibody) and all or substantially all of the framework regions of the human acceptor immunoglobulin. A humanized antibody can be produced using variety of techniques known in the art, including but not limited to, CDR-grafting, veneering or resurfacing, chain shuffling.

A chimeric antibody comprises non-human variable region sequences and human constant region sequences. A chimeric antibody may be monovalent, divalent or polyvalent. A monovalent chimeric antibody is a dimer formed by a chimeric heavy chain associated through disulfide bridges with a chimeric light chain. A divalent chimeric antibody is a tetramer formed by two heavy-light chain dimers associated through at least one disulfide bridge. A polyvalent chimeric antibody can also be produced, for example, by employing a heavy chain constant region that aggregates (e.g., from an IgM heavy chain).

A "camelised" antibody is one having a functional antigen binding site comprising only the heavy chain variable domains (VH), rather than the conventional antigen binding site which comprises both the heavy and the light chain variable domains (VL). Preferably, a camelised antibody comprises one or two VH domains and no VL domains. Preferably, a camelised antibody comprises two VH domains. Methods for making camelised antibodies are known in the art.

The antibodies for use in the methods and compositions of the invention may be produced by recombinant expression using techniques known in the art.

RNA Based Inhibitors

In some embodiments, the direct inhibitor of BCL2A1/BFL1 is one that inhibits the production of BCL2A1/BFL1 by a cell, for example by decreasing expression of the BCL2A1/BFL1 gene in the cell, preferably in activated tissue neutrophils. In embodiments, the inhibitor is a polynucleotide, preferably a single or double stranded ribonucleic acid (RNA) agent. An RNA agent inhibits expression of a target gene, for example, by catalyzing the post-transcriptional cleavage of the target mRNA, or by inhibiting transcription or translation of the target mRNA. In accordance with some embodiments, the RNA agent is targeted to inhibit expression of the murine BCLA1 gene or, preferably, the human BFL1 gene. In embodiments, the inhibitor is a double stranded or single stranded RNA interference-based agent (RNAi). The RNAi agent may be based on a microRNA (miRNA), a short hairpin RNA (shRNA), or a small interfering RNA (siRNA) that may be single or double stranded. The RNAi agent comprises a region that is at least partially, and in some embodiments fully, complementary to the target RNA. Although perfect complementarity is not required, the correspondence should be sufficient to enable the RNAi agent, or its cleavage product in the case of double stranded siRNA or RNAi agents comprising cleavable linkers, to direct sequence specific silencing of the target mRNA, e.g., by RNAi-directed cleavage of the target mRNA. Over 20 RNAi-based therapeutic agents are in clinical trials in the United States and this technique has shown considerable promise in selectively inhibiting target gene expression to achieve clinical results. See e.g., Bobbin and Rossi *Annu Rev. Pharmacol Toxicol* 2016 56:103-122. In embodiments, the RNAi agent may further comprise a delivery system, for example a liposomal or nanoparticle-based delivery system.

In embodiments, the RNAi agent further comprises one or more modified nucleotides, particularly of the single stranded regions of a double-stranded RNA or the terminal regions of a single stranded RNA. In the case of a double-stranded RNA, the dsRNAi agent typically includes at least one 3' overhang of about 2-5 nucleotides and may include one or two 5' or 3' overhangs, which can be the result of one strand being longer than the other, or of two strands of the same length being staggered. Modifications may include those that stabilize the 3' and/or 5' ends of the RNAi agent against the activity of exonucleases, for example modifications of the 2' hydroxy (OH) group of the ribose sugar to a 2' fluorine or 2' hydroxymethyl moiety. Other modifications may include the use of deoxyribonucleotides, e.g., deoxythymidine, instead of ribonucleotides at the 2' OH group of the ribose sugar, and modifications in the phosphate group, e.g., phosphothioate modifications.

In some embodiments, the RNAi agent further comprises a targeting moiety which is conjugated to the RNAi agent, optionally via a linker, or alternatively the targeting moiety may be conjugated to a delivery vehicle, such as a liposome-based nanoparticle. In embodiments, the targeting moiety targets delivery of the RNAi agent to neutrophils, preferably to activated tissue neutrophils. In embodiments, the targeting moiety comprises a polypeptide or an antibody, or antigen-binding fragment thereof, that binds to a neutrophil-specific cell surface glycoprotein. In embodiments, the neutrophil-specific cell surface glycoprotein is selected from a cluster of differentiation ("CD") protein including CD177 and CD66b, signal regulatory protein alpha ("SIRPa"), and sialic acid-binding Ig-like lectin 9 (SIGLEC9). In some embodiments, the targeting moiety may be an antibody or antigen binding fragment thereof that targets proteinase 3 ("PRTN3").

In some embodiments, the RNAi agent is an siRNA targeted to BCLA1/BFL1 mRNA in a human neutrophil cell, preferably an activated neutrophil, the siRNA being encapsulated in a liposome-based nanoparticle ranging in size from about 50-500 nanometers ("nm") mean diameter, preferably about 50-100 nm mean diameter, the liposomes formed from neutral phopholipids comprising a glycosaminoglycan, preferably hyaluronan, to which a targeting moiety is attached. In embodiments, the targeting moiety is selected from a polypeptide or an antibody, or antigen-binding fragment thereof, that binds to a neutrophil-specific cell surface glycoprotein. In embodiments, the neutrophil-specific cell surface glycoprotein is selected from CD177, CD66b, SIRPa, and SIGLEC9. In some embodiments, the targeting moiety may be a polypeptide or an antibody, or antigen binding fragment thereof, that targets PRTN3. In embodiments, the targeting moiety is covalently attached to the glycosaminoglycan component of the liposome.

In some embodiments, the inhibitor of BCLA1/BFL1 is a small organic molecule. In this context, the term "small organic molecule" refers to organic compounds having a molecular weight of less than about 5,000 grams per mole, less than about 1,000 grams per mole, less than about 500 grams per mole, or less than about 100 grams per mole, and salts, esters, and other pharmaceutically acceptable forms of such compounds. In embodiments, the molecular weight of a small organic molecule of the disclosure is between 100 and 500 grams per mole, or between 500 and 1,000 grams per mole, or between 1,000 and 5,000 grams per mole. In embodiments, the small organic molecule is encapsulated within a liposome-based nanoparticle delivery system targeted for delivery to human neutrophil cells, preferably activated neutrophils, the liposome-based nanoparticle ranging in size from about 50-500 nanometers ("nm") mean diameter, preferably about 50-100 nm mean diameter, and formed from neutral phopholipids comprising a glycosaminoglycan, preferably hyaluronan, to which a targeting moiety is attached. In embodiments, the targeting moiety is selected from an antibody, or antigen-binding fragment thereof, that binds to a neutrophil-specific cell surface glycoprotein. In embodiments, the neutrophil-specific cell surface glycoprotein is selected from CD177, CD66b, SIRPa, and SIGLEC9. In some embodiments, the targeting moiety may be an antibody or antigen binding fragment thereof that targets PRTN3. In embodiments, the targeting moiety is covalently attached to the glycosaminoglycan component of the liposome.

Small Molecules

In embodiments, the inhibitor of BCL2A1/BFL1 is a small organic molecule, for example a small molecule of Formula I, or a derivative thereof. Exemplary derivatives include compounds of Formula I, Ia, Ib, Ic, and Id in which the azo bond is reduced to an azine bond or replaced with a sulfonamide, thioether, or sulfone linker, or an isosteric alkene or alkane bond; or compounds of Formula Ie and If in which all of the azo bonds are reduced to an azine bond or replaced with a sulfonamide, thioether, or sulfone linker, or an isosteric alkene or alkane bond.

The disclosure provides compounds of Formula I which bind to either the P2 or the P4 pocket of BCL2A1/BFL1 and are inhibitors of BCL2A1/BFL1:

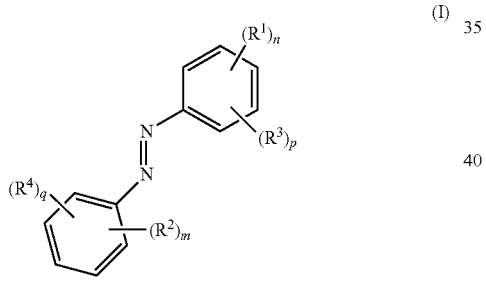

(I)

wherein,
each $R^1$ is independently selected from the group consisting of $C_{1-8}$ alkyl, $C_{1-8}$ alkoxy, halo, —OH, —S(O)$_2$—$R^{1a}$, —P(O)(OH)—$R^{1a}$, —NH$_2$, —NH—$C_{1-8}$ alkyl, N($C_{1-8}$ alkyl)$_2$, and —NO$_2$, or two $R^1$ groups on adjacent ring vertices combine to form a 6-membered aromatic ring;
each $R^{1a}$ is independently selected from the group consisting of H, OH, $C_{1-8}$ alkyl, and $C_{1-8}$ alkoxy;
the subscript n is an integer from 0 to 3;
each $R^2$ is independently selected from the group consisting of $C_{1-8}$ alkyl, $C_{1-8}$ alkoxy, halo, —OH, —S(O)$_2$—$R^{2a}$, —P(O)(OH)—$R^{2a}$, —NH$_2$, —NH—$C_{1-8}$ alkyl, —N($C_{1-8}$ alkyl)$_2$, and —NO$_2$, or two $R^2$ groups on adjacent ring vertices combine to form a 6-membered aromatic ring;
each $R^{2a}$ is independently selected from the group consisting of H, OH, $C_{1-8}$ alkyl, and $C_{1-8}$ alkoxy;
the subscript m is an integer from 0 to 3;
$R^3$ is selected from the group consisting of —N=N-phenyl, —N=N-naphthyl, —N=N-phenyl-N=N-naphthyl, and —N=N-phenyl-N=N-phenyl, wherein each phenyl and naphthyl moiety are substituted with from 0 to 3 $R^{3a}$ moieties;
each $R^{3a}$ is independently selected from the group consisting of $C_{1-8}$ alkyl, halo, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, and —S(O)$_2$—$C_{1-8}$ alkyl;
the subscript p is an integer from 0 to 1; and
$R^4$ is selected from the group consisting of —C(O)—NR$^{4a}$-phenyl, wherein each phenyl group is substituted with from 0 to 3 $R^{4b}$ moieties;
$R^{4a}$ is selected from the group consisting of H and $C_{1-8}$ alkyl;
each $R^{4b}$ is independently selected from the group consisting of $C_{1-8}$ alkyl, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, and —S(O)$_2$—$C_{1-8}$ alkyl;
the subscript q is an integer from 0 to 1; or
a pharmaceutically acceptable salt thereof.

In embodiments, Formula I is represented by Formula Ia

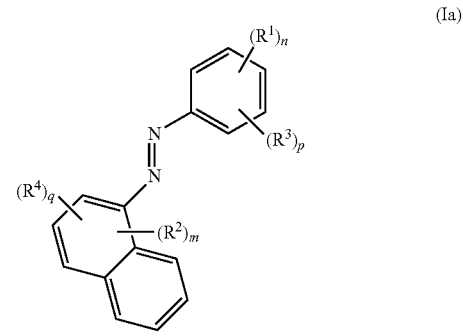

(Ia)

wherein,
each $R^1$ is independently selected from the group consisting of $C_{1-8}$ alkyl, $C_{1-8}$ alkoxy, halo, —OH, —S(O)$_2$—$R^{1a}$, —P(O)(OH)—$R^{1a}$, —NH$_2$, —NH—$C_{1-8}$ alkyl, —N($C_{1-8}$ alkyl)$_2$, and —NO$_2$, or two $R^1$ groups on adjacent ring vertices combine to form a 6-membered aromatic ring;
each $R^{1a}$ is independently selected from the group consisting of H, OH, $C_{1-8}$ alkyl, and $C_{1-8}$ alkoxy;
the subscript n is an integer from 0 to 3;
each $R^2$ is independently selected from the group consisting of $C_{1-8}$ alkyl, $C_{1-8}$ alkoxy, halo, —OH, —S(O)$_2$—$R^{2a}$, —P(O)(OH)—$R^{2a}$, —NH$_2$, —NH—$C_{1-8}$ alkyl, —N($C_{1-8}$ alkyl)$_2$, and —NO$_2$;
each $R^{2a}$ is independently selected from the group consisting of H, OH, $C_{1-8}$ alkyl, and $C_{1-8}$ alkoxy;
the subscript m is an integer from 0 to 3;
$R^3$ is selected from the group consisting of —N=N-phenyl, —N=N-naphthyl, —N=N-phenyl-N=N-naphthyl, and —N=N-phenyl-N=N-phenyl, wherein each phenyl and naphthyl moiety are substituted with from 0 to 3 $R^{3a}$ moieties;
each $R^{3a}$ is independently selected from the group consisting of $C_{1-8}$ alkyl, $C_{1-8}$ alkoxy, halo, —OH, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, —S(O)$_2$—$C_{1-8}$ alkyl, —P(O)(OH)—OH, —P(O)(OH)—H, —P(O)(OH)—O—$C_{1-8}$ alkyl, and —P(O)(OH)—$C_{1-8}$ alkyl;

the subscript p is an integer from 0 to 1; and

R⁴ is selected from the group consisting of —C(O)—NR$^{4a}$-phenyl, wherein each phenyl group is substituted with from 0 to 3 R$^{4b}$ moieties;

R$^{4a}$ is selected from the group consisting of H and $C_{1-8}$ alkyl;

each R$^{4b}$ is independently selected from the group consisting of $C_{1-8}$ alkyl, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, and —S(O)$_2$—$C_{1-8}$ alkyl;

the subscript q is an integer from 0 to 1; or a pharmaceutically acceptable salt thereof.

In embodiments, Formula I is represented by Formula Ib

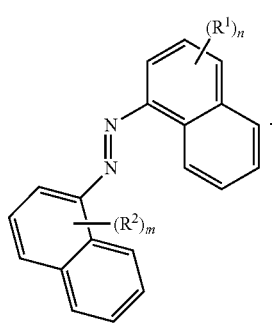

(Ib)

In embodiments, Formula I is represented by Formula Ic

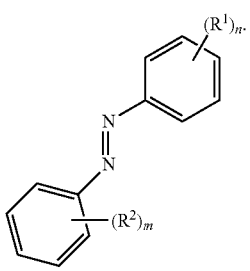

(Ic)

In embodiments, Formula I is represented by Formula Id

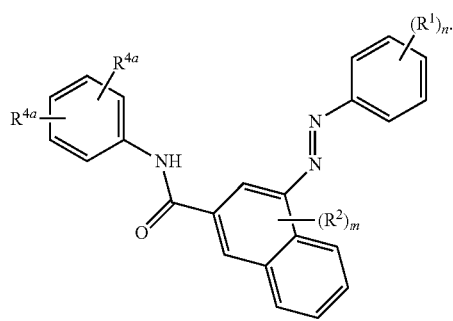

(Id)

In embodiments, Formula I is represented by Formula Ie

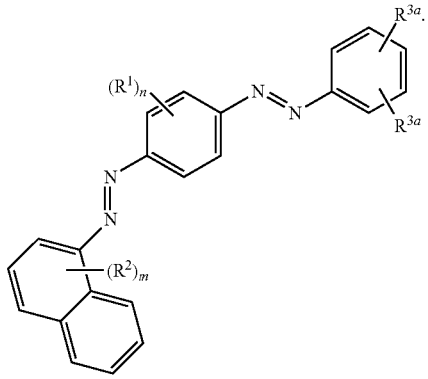

(Ie)

In embodiments, Formula I is represented by Formula If

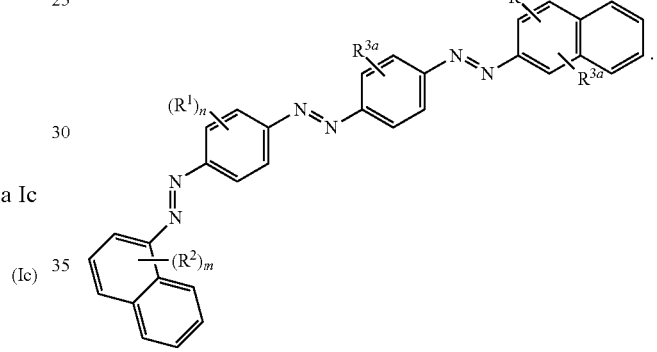

(If)

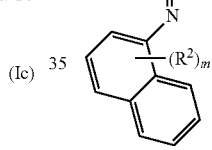

In embodiments, each R¹ in Formula I, Ia, Ib, Ic, Id, Ie, or If is independently selected from the group consisting of $C_{1-8}$ alkyl, $C_{1-8}$ alkoxy, halo, —OH, —S(O)$_2$—R$^{1a}$, —P(O)(OH)—R$^{1a}$, —NH$_2$, —NH—$C_{1-8}$ alkyl, —N($C_{1-8}$ alkyl)$_2$, and —NO$_2$.

In embodiments, each R¹ in Formula I, Ia, Ib, Ic, Id, Ie, or If is independently selected from the group consisting of $C_{1-8}$ alkyl, $C_{1-8}$ alkoxy, halo, —OH, —S(O)$_2$—R$^{1a}$, —P(O)(OH)—R$^{1a}$, and —NO$_2$.

In embodiments, each R¹ in Formula I, Ia, Ib, Ic, Id, Ie, or If is independently selected from the group consisting of $C_{1-8}$ alkyl, —OH, —S(O)$_2$—OH, and —NO$_2$.

In embodiments, the subscript n in Formula I, Ia, Ib, Ic, Id, Ie, or If is 1, 2, or 3.

In embodiments, the subscript n in Formula I, Ia, Ib, Ic, Id, Ie, or If is 1 or 2.

In embodiments, each R² in Formula I, Ia, Ib, Ic, Id, Ie, or If is independently selected from the group consisting of $C_{1-8}$ alkyl, $C_{1-8}$ alkoxy, halo, —OH, —S(O)$_2$—R$^{2a}$, —P(O)(OH)—R$^{2a}$, and —NO$_2$.

In embodiments, each R² in Formula I, Ia, Ib, Ic, Id, Ie, or If is independently selected from the group consisting of —OH, —S(O)$_2$—OH, and —NO$_2$.

In embodiments, the subscript m in Formula I, Ia, Ib, Ic, Id, Ie, or If is 1, 2, or 3.

In embodiments, the subscript m in Formula I, Ia, Ib, Ic, Id, Ie, or If is 1 or 2.

In embodiments, R³ in Formula I or Ia is selected from the group consisting of —N=N-phenyl, and —N=N-phenyl- N=N-naphthyl wherein each phenyl and naphthyl moiety are substituted with from 0 to 3 $R^{3a}$ moieties.

In embodiments, each $R^{3a}$ in Formula I, Ia, Ie, or If is independently selected from the group consisting of $C_{1-8}$ alkyl, halo, —$NH_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, —S(O)$_2$—$C_{1-8}$ alkyl.

In embodiments, each $R^{3a}$ in Formula I, Ia, Ie, or If is independently selected from the group consisting of $C_{1-8}$ alkyl, —$NH_2$, —S(O)$_2$—OH.

In embodiments, each $R^{4b}$ in Formula I, Ia, or Id is independently selected from the group consisting of $C_{1-8}$ alkyl, —$NH_2$.

In embodiments, the compounds of Formula I are selected from Table 1.

TABLE 1

Representative Compounds of Formula I. Binding specificity to the P2 or P4 pocket of BCL2-A1/BFL1 is indicated.

| Compound No. | Structure |
|---|---|
| 1.001<br>NSC-97318<br>P2 | 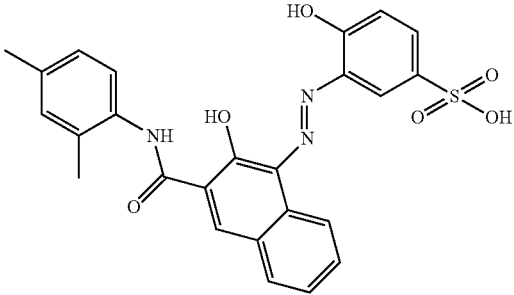 [SMILES: Cc1ccc(NC(=O)c2cc3ccccc3c(/N=N/c3cc(S(=O)(=O)O)ccc3O)c2O)c(C)c1] |
| 1.002<br>NSC-79711<br>P4 | 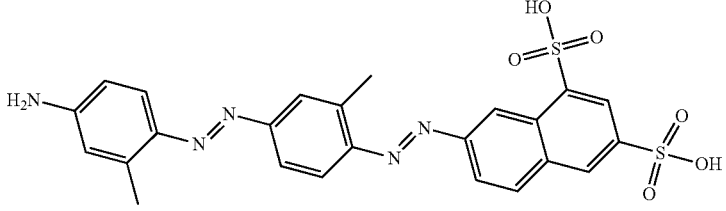 [SMILES: Cc1cc(N)ccc1/N=N/c1ccc(/N=N/c2ccc3cc(S(=O)(=O)O)cc(S(=O)(=O)O)c3c2)c(C)c1] |
| 1.003<br>NSC-45195<br>P4 | 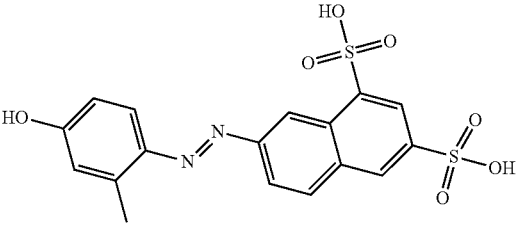 [SMILES: Cc1cc(O)ccc1/N=N/c1ccc2cc(S(=O)(=O)O)cc(S(=O)(=O)O)c2c1] |
| 1.004<br>NSC-65847<br>P4 | 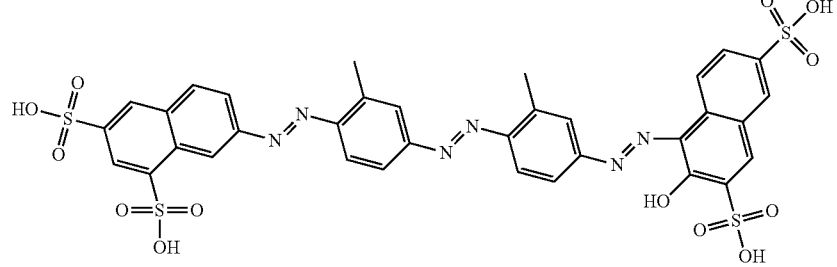 |

TABLE 1-continued
Representative Compounds of Formula I. Binding specificity to the P2 or P4 pocket of BCL2-A1/BFL1 is indicated.
| Compound No. | Structure |
| --- | --- |
| 1.005<br>NSC-65820<br>P4 | 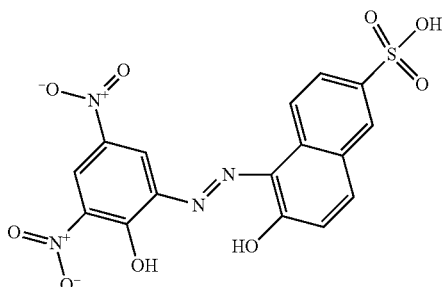 |
| 1.006<br>NSC-45538<br>P4 | 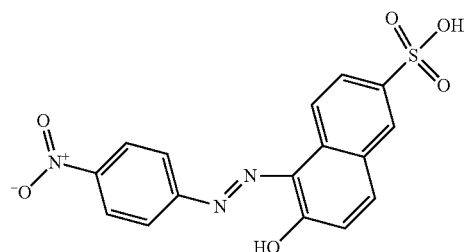 |
| 1.007<br>NSC-45576<br>P4 | 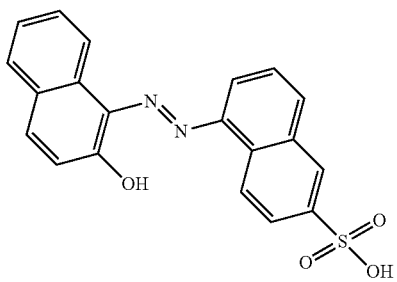 [SMILES: O=S(=O)(O)c1ccc2c(/N=N/c3c(O)ccc4ccccc34)cccc2c1] |
| 1.008<br>NSC-374898<br>P2 | 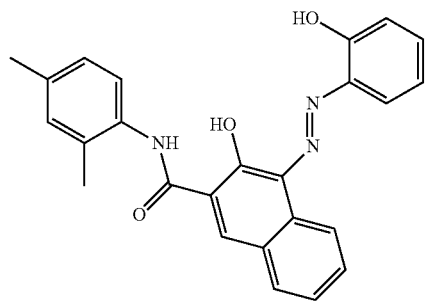 [SMILES: Cc1ccc(NC(=O)c2cc3ccccc3c(/N=N/c3ccccc3O)c2O)c(C)c1] |
| 1.009<br>NSC-10441<br>P4 | 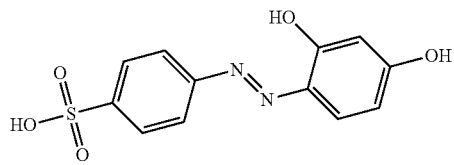 [SMILES: O=S(=O)(O)c1ccc(/N=N/c2ccc(O)cc2O)cc1] |
| 1.010<br>NSC-9360<br>P4 | 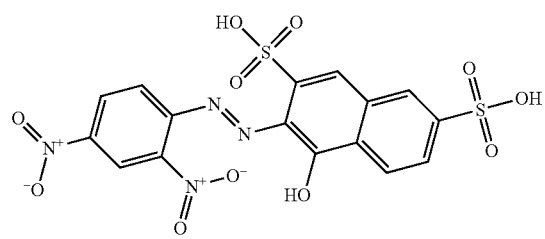 |

TABLE 1-continued

Representative Compounds of Formula I. Binding specificity to the P2 or P4 pocket of BCL2-A1/BFL1 is indicated.

| Compound No. | Structure |
| --- | --- |
| 1.011<br>NSC-51525<br>P4 | 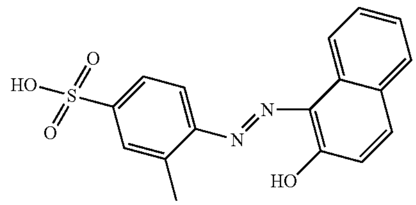 [SMILES: Cc1cc(S(=O)(=O)O)ccc1/N=N/c1c(O)ccc2ccccc12] |
| 1.012<br>NSC-7223<br>P4 | 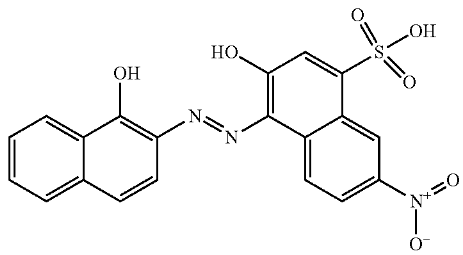 [SMILES: O=[N+]([O-])c1ccc2c(/N=N/c3ccc4ccccc4c3O)c(O)cc(S(=O)(=O)O)c2c1] |

In embodiments, the disclosure provides a BCL2-A1/BFL1 inhibitor that binds to the P4 pocket of BCL2-A1/BFL1, referred to herein as a "BCL2-A1/BFL1 P4 inhibitor". In embodiments, the BCL2-A1/BFL1 P4 inhibitor is a compound of Formula I. In embodiments, the BCL2-A1/BFL1 P4 inhibitor is selected from compound 1.002, 1.003, 1.004, 1.005, 1.006, 1.007, 1.009, 1.010, 1.011, and 1.012 of Table 1.

In embodiments, the disclosure provides a BCL2-A1/BFL1 inhibitor that binds to the P2 pocket of BCL2-A1/BFL1, referred to herein as a "BCL2-A1/BFL1 P2 inhibitor". In embodiments, the BCL2-A1/BFL1 P2 inhibitor is a compound of Formula I. In embodiments, the BCL2-A1/BFL1 P2 inhibitor is selected from compound 1.001 and 1.008 of Table 1.

In embodiments, the BCL2-A1/BFL1 inhibitor is a compound of Formula Ia-If in which the azo bond bridging the rings is reduced to an azine bond or replaced with a sulfonamide, thioether, or sulfone linker, or an isosteric alkene or alkane bond. In embodiments, the BCL2-A1/BFL1 inhibitor is a compound selected from 1.001, 1.002, 1.003, 1.004, 1.005, 1.006, 1.007, 1.008, 1.009, 1.010, 1.011, and 1.012 of Table 1 in which the azo bond, or at least one of the azo bonds if more than one is present, bridging two rings is reduced to an azine bond or replaced with a sulfonamide, thioether, or sulfone linker, or an isosteric alkene or alkane bond. In embodiments, the BCL2-A1/BFL1 inhibitor is a compound selected from 1.001, 1.002, 1.003, 1.004, 1.005, 1.006, 1.007, 1.008, 1.009, 1.010, 1.011, and 1.012 of Table 1 in which each azo bond bridging two rings is reduced to an azine bond or replaced with a sulfonamide, thioether, or sulfone linker, or an isosteric alkene or alkane bond.

In embodiments, the BCL2-A1/BFL1 inhibitor is a compound of Formula I in which the sulfonate group is converted to a sulfone group. In embodiments, the BCL2-A1/BFL1 inhibitor is a compound selected from 1.001, 1.002, 1.003, 1.004, 1.005, 1.006, 1.007, 1.009, 1.010, 1.011, and 1.012 of Table 1 in which the sulfonate group, or at least one of the sulfonate groups if more than one is present, is converted to a sulfone group. In embodiments, the BCL2-A1/BFL1 inhibitor is a compound selected from 1.001, 1.002, 1.003, 1.004, 1.005, 1.006, 1.007, 1.009, 1.010, 1.011, and 1.012 of Table 1 in which each sulfonate group is converted to a sulfone group.

Definitions

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Halogen" or "halo" refers to fluorine, chlorine, bromine and iodine.

As used herein, when the position of a substituent on a ring is not directly attached to a ring vertex, the substituent can be on any suitable ring vertex. For example, in the structure shown below

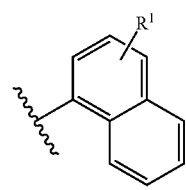

the R¹ substituent can be on any suitable vertex within either ring, as shown below:

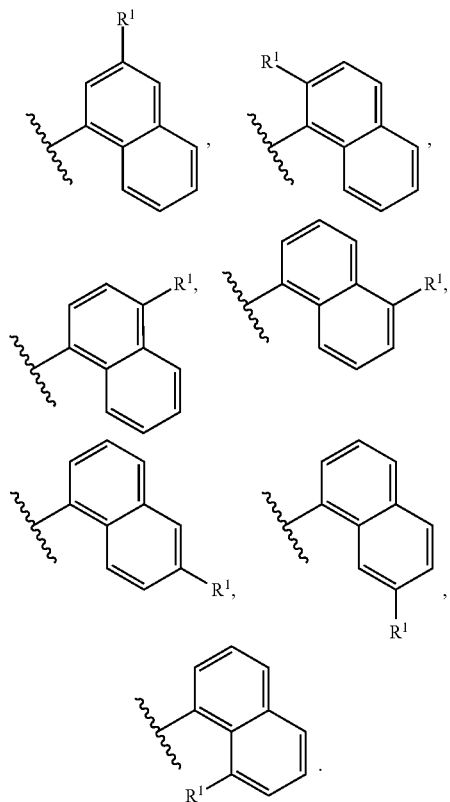

Compositions

In embodiments, the disclosure provides a pharmaceutical composition comprising an inhibitor of BCL2-A1/BFL1, and one or more excipients or carriers, preferably pharmaceutically acceptable excipients or carriers. In embodiments, the inhibitor is a BCL2-A1/BFL1 P4 inhibitor or a BCL2-A1/BFL1 P2 inhibitor.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Excipients for preparing a pharmaceutical composition are generally those that are known to be safe and non-toxic when administered to a human or animal body. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, and suitable mixtures of any of the foregoing. The particular excipients utilized in a composition will depend upon various factors, including chemical stability and solubility of the compound being formulated and the intended route of administration.

A pharmaceutical composition can be provided in bulk or unit dosage form. It is especially advantageous to formulate pharmaceutical compositions in unit dosage form for ease of administration and uniformity of dosage. The term "unit dosage form" refers to physically discrete units suited as unitary dosages for the subject to be treated; each unit containing a predetermined quantity of an active compound calculated to produce the desired therapeutic effect in association with the required pharmaceutical carrier. A unit dosage form can be an ampoule, a vial, a suppository, a dragee, a tablet, a capsule, an IV bag, or a single pump on an aerosol inhaler.

In therapeutic applications, dose may vary depending on the chemical and physical properties of the active compound as well as clinical characteristics of the subject, including e.g., age, weight, and co-morbidities. Generally, the dose should be a therapeutically effective amount. An effective amount of a pharmaceutical composition is that which provides an objectively identifiable improvement as noted by the clinician or other qualified observer. For example, alleviating a symptom of a disorder, disease or condition.

A pharmaceutical compositions may take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). In embodiments, the pharmaceutical composition is in the form of an orally acceptable dosage form including, but not limited to, capsules, tablets, buccal forms, troches, lozenges, and oral liquids in the form of emulsions, aqueous suspensions, dispersions or solutions. Capsules may contain excipients such as inert fillers and/or diluents including starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added.

In embodiments, the pharmaceutical composition is in the form of a tablet. The tablet can comprise a unit dose of a compound described here together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. butylated hydroxytoluene), buffering agents (e.g. phosphate or citrate buffers), and effervescent agents such as citrate/bicarbonate mixtures. The tablet may be a coated tablet. The coating can be a protective film coating (e.g. a wax or varnish) or a coating designed to control the release of the active compound, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecyl sulfate, magnesium aluminum silicate, and triethanolamine.

In embodiments, the pharmaceutical composition is in the form of a hard or soft gelatin capsule. In accordance with this formulation, the compound of the present invention may be in a solid, semi-solid, or liquid form.

In embodiments, the pharmaceutical composition is in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

In embodiments, the pharmaceutical composition is in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions can be prepared in water with the aid of co-solvent or a surfactant. Examples of suitable surfactants include polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides. Dispersions can also be prepared, for example, in glycerol, liquid polyethylene glycols and mixtures of the same in oils.

In embodiments, a compound or composition described here may be administered as monotherapy or adjunctive therapy. In embodiments, a compound or composition described here may be administered alone or in combination with one or more additional therapeutic agents (i.e., additional APIs) or therapies, for example as part of a therapeutic regimen that includes, e.g., aspects of diet and exercise). In embodiments, the methods described here include administration of a BCL2-A1/BFL1 inhibitor as the primary therapy. In other embodiments, the administration of a BCL2-A1/BFL1 inhibitor is an adjuvant therapy. In either case, the methods of the invention contemplate the administration of a BCL2-A1/BFL1 inhibitor in combination with one or more additional therapeutic agents and/or therapies for the treatment or prevention of a disease, disorder, or condition as described here. The terms "therapy" and "therapies" refer to any method, protocol and/or agent that can be used in the prevention, treatment, management or amelioration of a disease, disorder, or condition, one or more symptoms thereof.

The present disclosure also provides packaging and kits comprising pharmaceutical compositions for use in the methods described here. The kit can comprise one or more containers selected from the group consisting of a bottle, a vial, an ampoule, a blister pack, and a syringe. The kit can further include one or more of instructions for use, one or more syringes, one or more applicators, or a sterile solution suitable for reconstituting a compound or composition described here.

EXAMPLES

The following examples describe Applicant's work which led to the identification of BCL2A1/BFL1 as critical to the survival of maternal neutrophils infiltrating the chorio-decidua during chorioamnionitis, and the development of small molecule inhibitors of BCL2A1/BFL1. As shown in Example 1 below, neutrophils significantly contributed to the amplification of inflammation at the maternal-fetal interface during intrauterine infection. Inhibition of BCL2A1/BFL1 provides an alternative to IL-1 inhibition in the prophylaxis and treatment of intrauterine infection, as well as other diseases and disorders characterized by pathological neutrophil mediated inflammation. Targeting BCL2A1/BFL1 for inhibition is advantageous compared to IL-1 in part because its inhibition is expected to have fewer off-target effects. In addition, we show that BCL2A1/BFL1 is upregulated in a diverse array of cancers, making its targeted inhibition attractive for use as an anti-cancer agent, either alone or in combination with other agents, especially other BCL-2 family inhibitors.

Figure 1B:
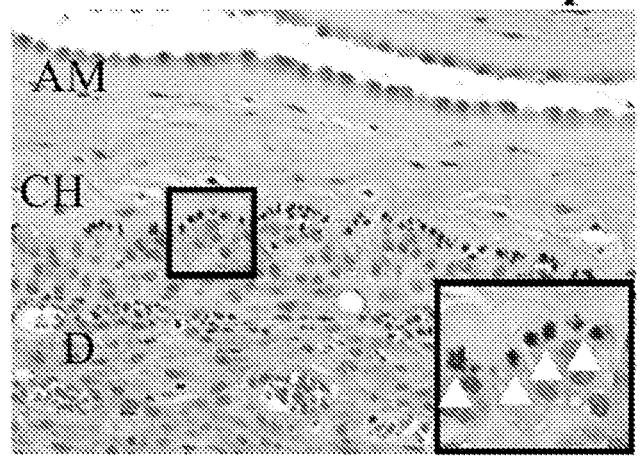
Figure 1B:
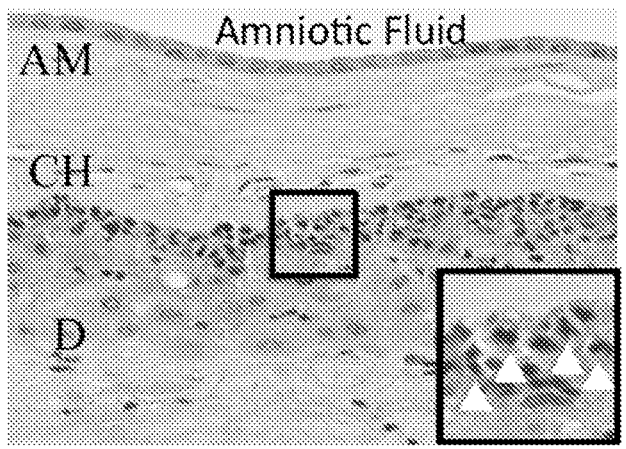
Figure 1C:
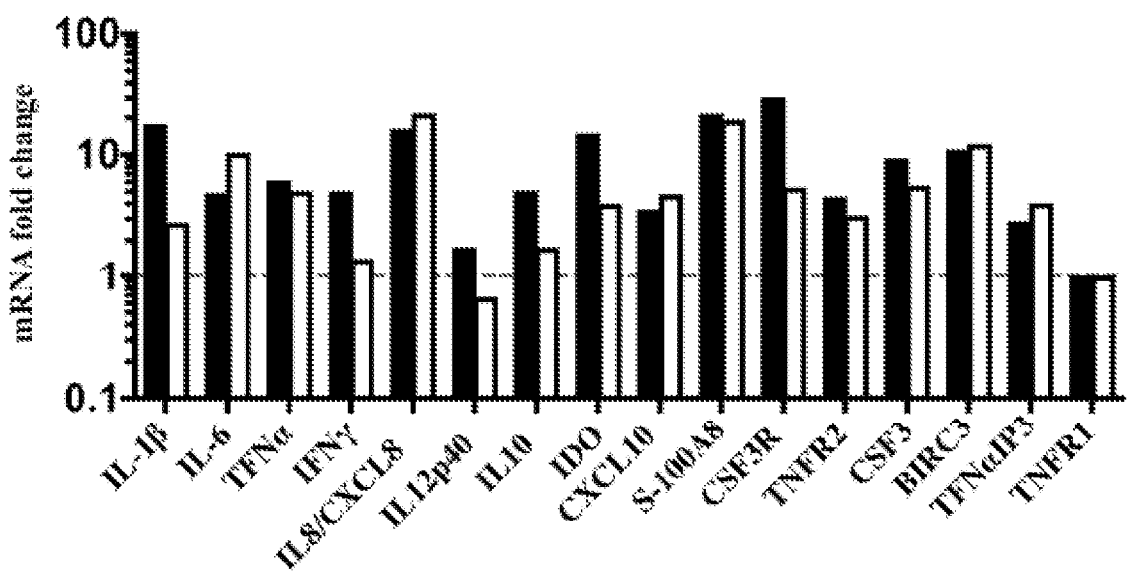

Example 1: IL-1 Signaling Mediates Chorio-Decidua Neutrophil Recruitment, Activation, and Intrauterine Inflammation We utilized the LPS-induced chorioamnionitis Rhesus monkey model system to study the pathogenesis of IUI, and particularly the role of IL-1 signaling in chorioamnionitis. A human recombinant IL-1 receptor antagonist (referred to herein as "hIL-1ra" or by its generic name, "anakinra") which inhibits both IL-1ß and IL-1α signaling was used to experimentally block IL-1 signaling. We show that IL-1 signaling mediates accumulation and activation of neutrophils at the maternal-fetal interface and demonstrate a previously unrecognized function for BCL2A1 in mediating enhanced survival of these chorio-decidua neutrophils. Human and Rhesus Chorioamnionitis have Similar Inflammation Readouts The cellular and molecular characteristics of inflammation in the LPS-induced chorioamnionitis Rhesus monkey model are very similar to that in human chorioamnionitis. Chorioamnionitis was induced in rhesus macaques by intra-amniotic (IA) injection of LPS at 80% gestation with delivery 16 hours later (n=29). Human samples were collected immediately after birth from a cohort of women (n=30) delivering pre-term, and chorioamnionitis was diagnosed by placenta histology. Tables 3 and 4 show the characteristics of the monkey and human subjects. Chorio-decidua cells were scraped and digested with protease/DNAase, and single cell suspensions were used for multi-parameter flow cytometry phenotyping (rhesus chorio neg., n=16; rhesus chorio pos., n=13; human chorio neg., n=8; human chorio pos., n=7). The percentage of CD45+ cells and cell type in normal compared to chorioamnionitis was compared in both monkey and human (FIG. 1A). The data show close similarities in proportions of CD45+ subsets in rhesus vs. human neutrophil predominance in the chorioamnionitis positive groups. In both the Rhesus and human chorio-decidua (CD), NK cells and macrophages were the most abundant leukocytes at baseline. Analysis of representative fetal membranes (chorioamnion-decidua, CAD; n=5) by H&E histology showed clear neutrophil infiltration at the chorio-decidua interface (white arrowheads) in both rhesus and human chorioamnionitis (am, amnion; ch, cho-rion; dp, decidua parietalis) (FIG. 1B). Thus, in contrast to baseline, neutrophils became the most abundant leukocytes during chorioamnionitis. Neutrophils were primarily located at the CD interface in both the Rhesus and human tissues. The mRNA profile and magnitude of induction of pro- and anti-inflammatory mediators were similar in the Rhesus and humans, as demonstrated by expression analysis of mRNAs by quantitative PCR (Taqman probes) in the fetal membranes during chorioamnionitis (FIG. 1C).

IA LPS Causes a Time-Dependent Inflammation at the Maternal-Fetal Interface

Figure 2:
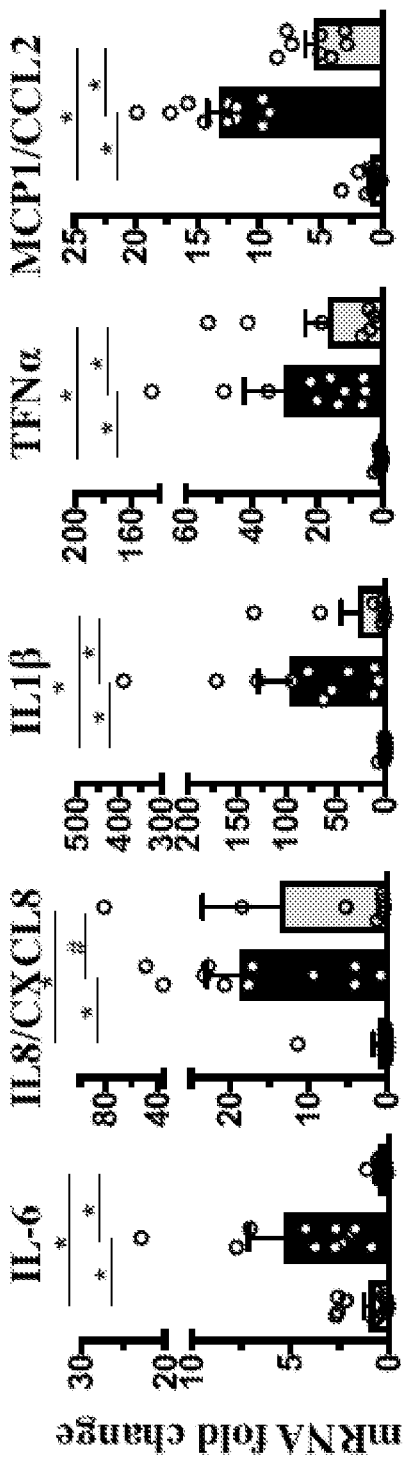
FIG. 2: Time-course of inflammation induced by IA-LPS injection in chorioamnion-decidua (CAD) in Rhesus macaques showing fold change in mRNA expression for IL-6, IL-8/CXCL8, IL1beta, TNFalpha, and MCP1/CCL2 in control (open bars), LPS-induced chorioamnionitis at 16 hours (dark filled bars) and LPS-induced chorioamnionitis at 48 hours (light filled bas).

To understand the kinetics of inflammation, we surgically delivered Rhesus macaques 16 h or 48 h after intra-amniotic injection of ("IA LPS"). IA LPS increased expression of IL6, IL8/CXCL8, IL1β, TNFα; MCP1/CCL2 mRNAs in the chorioamnion-decidua (FIG. 2) and induced a robust inflammatory response at 16 hours with a subsequent decrease at 48 hours. Histograms represent cytokine mRNAs in the chorioamnion-decidua expressed as fold increases over the average value for controls after internally normalizing to the housekeeping 18S RNA. (Data are mean, SEM. *$p<0.05$ between comparators; #$0.1<p>0.05$ between comparators). Since inflammatory markers were higher at 16 h compared to 48 h, the 16 h time-point for subsequent studies was used.

Figure 3B:
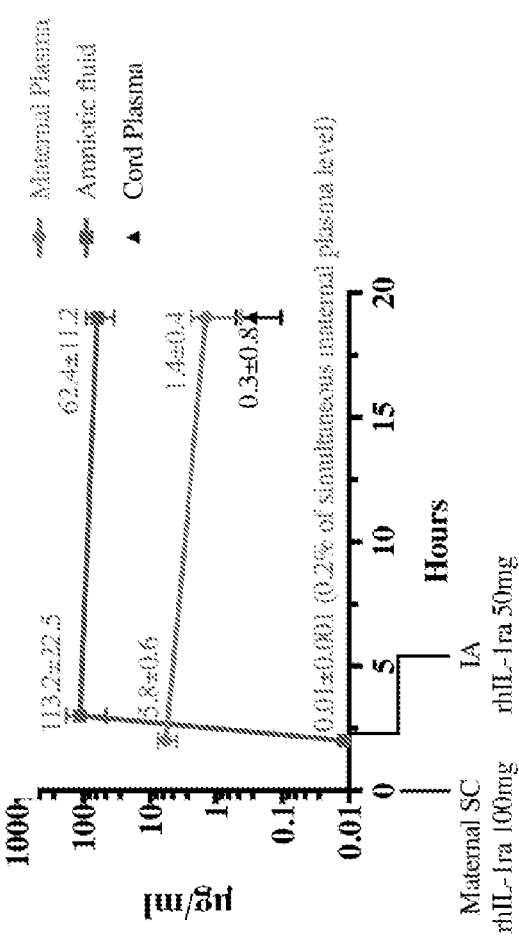
FIGS. 3A-B: Experimental scheme and Anakinra™ (rhIL-1ra) pharmacokinetics showing (A) schematic of dosing regimen in ~130-day Rhesus macaques (80% gestation) and (B) pharmacokinetics of Anakinra measured by human IL-1ra specific bead-based ELISA.
Figure 3A:
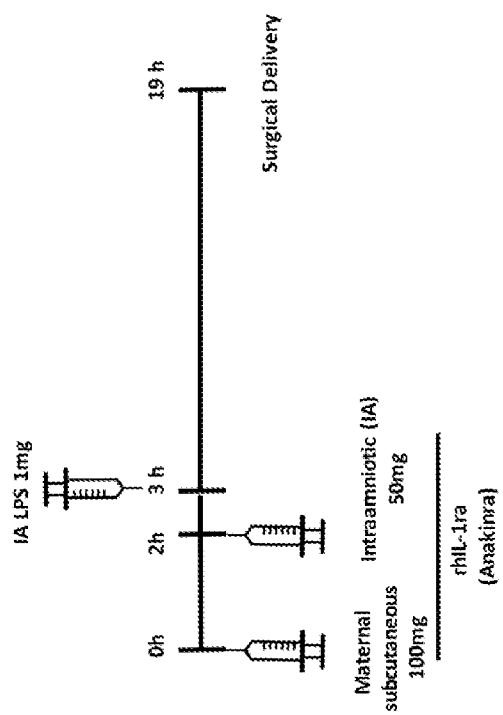
Figure 4A:
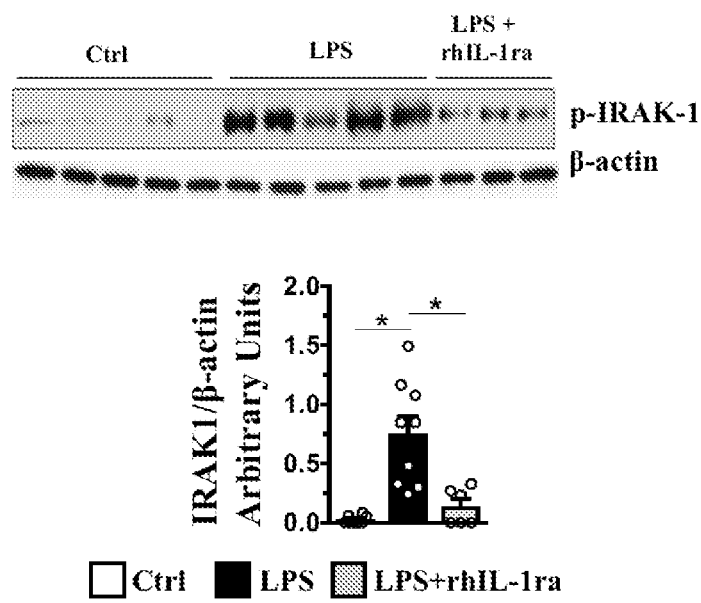
FIGS. 4A-D: Signaling in the amnion via activation of IRAK1 and induction of neutrophil chemoattractants are IL-1 dependent. Amnion was physically separated from chorion and decidua immediately after birth from Rhesus and Human delivering pre-term. Representative immunoblots of Rhesus amnion probed with anti-phospho-IRAK1 and beta-actin are shown above bar plots of IRAK1 expression. (A) Rhesus monkey, control (open bars), LPS-induced chorioamnionitis (dark filled bars), and LPS-induced chorioamnionitis plus the IL-1 inhibitor, rhIL-1ra (light filled bars); (B) human, chorioamnionitis negative (open bars) and chorioamnionitis positive (dark filled bars). mRNA expression of CSF3, IL8/CXCL8, IL-6 and IL-1B in (C) monkey control (open bars), LPS-induced chorioamnionitis (dark filled bars), and LPS-induced chorioamnionitis plus the IL-1 inhibitor, rhIL-1ra (light filled bars); and (D) human, chorioamnionitis negative (open bars) and chorioamnionitis positive (dark filled bars). Data are mean, SEM, *p<0.05 between comparators.
Figure 4B:
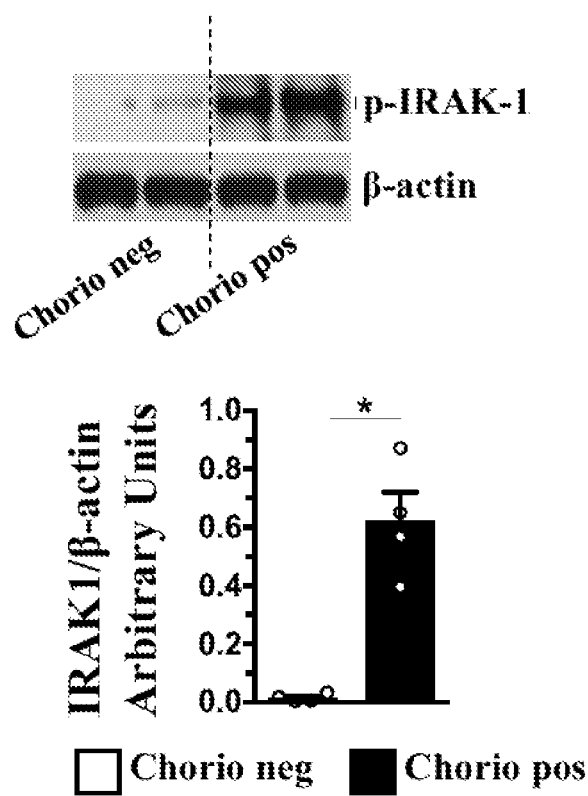
Figure 4C:
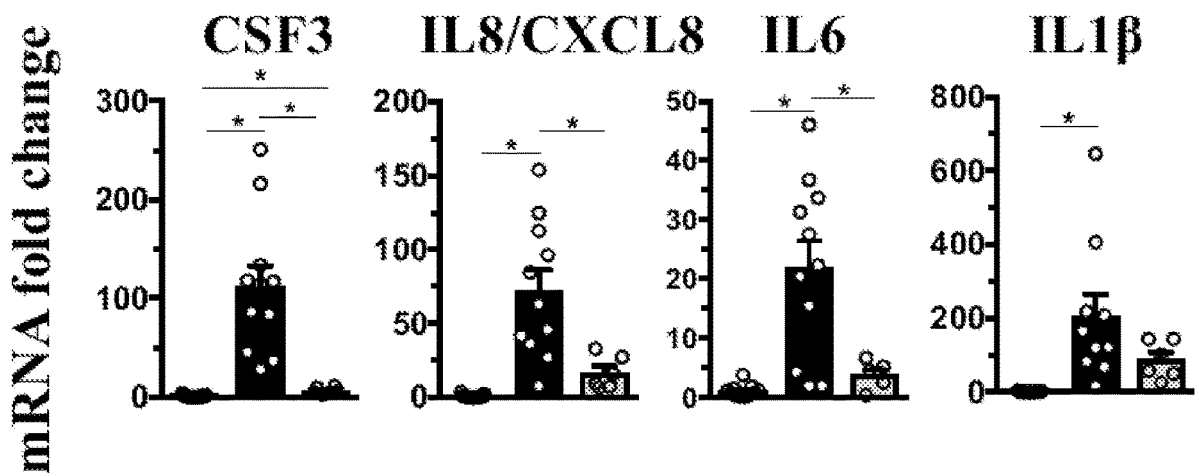
Figure 4D:
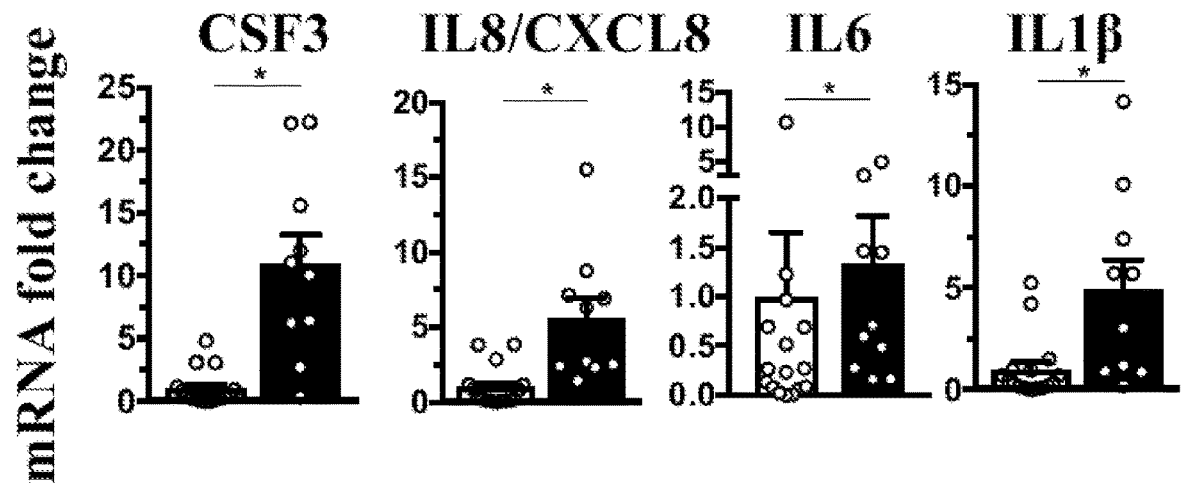

Recombinant human IL-1 receptor antagonist ("Anakinra" or "rhIL1ra") was injected into the amniotic fluid ("AF") and subcutaneously in the dams (FIG. 3A). Subcutaneous rhIL1ra crossed the amniotic epithelial barrier minimally (0.2% diffusion from blood to AF) (FIG. 3B). rhIL1ra elimination was slower in the AF compared to maternal blood, but both compartments had therapeutic concentrations. The low (0.2%) diffusion of Anakinra from maternal blood to amniotic fluid 2 h after maternal subcutaneous (SC) before the AF Anakinra dosing is notable. In addition, a slower clearance of Anakinra from the AF compared to maternal plasma is observed. There was a substantial transfer of Anakinra (19 h level) to fetal plasma reflecting trans-placental transfer.

rhIL1ra Blocks Activation of IRAK1 and Expression of Neutrophil Chemoattractants in the Amnion Since amnion is in contact with amniotic fluid, it is strategically located to transduce inflammatory signals in the amniotic fluid to recruit neutrophils to the chorio-decidua. Phospho-IRAK1 (pIRAK1), a key mediator of TLR signaling, was selectively induced in the amnion by exposure to LPS (FIG. 4A). rhIL-1ra decreased LPS-induced pIRAK1 and the expression of CSF3, CXCL8, IL6 in the amnion (FIG. 4C). In clinical situations, inflammatory signals may come from the amniotic fluid (inside out signals) or from decidua (outside in signals). We found that pIRAK1 abundance and expression of CSF3, CXCL8, IL6, IL1β were both increased in the amnion from subjects with chorioamnionitis compared to control subjects (FIG. 4B, 4D). Thus, amnion expression of neutrophil chemoattractants appears to be a general phenomenon during chorioamnionitis.

rhIL1ra Blocks Neutrophil Accumulation in Chorio-Decidua

Figure 5A:
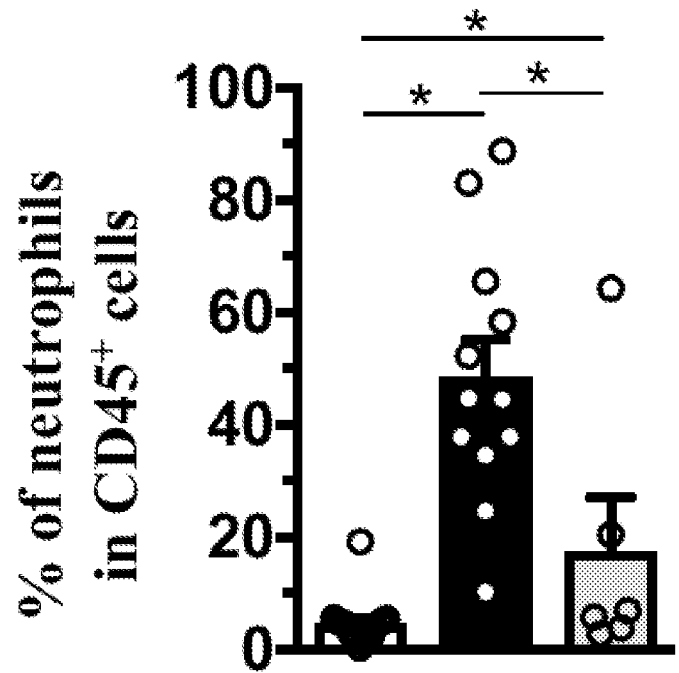
FIGS. 5A-B: Neutrophil recruitment to the chorio-decidua after IA LPS exposure is significantly decreased by the IL-1R blockade. Chorio-decidua cell suspensions were analyzed by multi-parameter flow cytometry. IA-LPS exposure increased significantly the frequency (A) and the number (B) of chorio-decidua neutrophils compared to the control animals and rhIL1ra injection reverted both frequency and counts to near controls levels. Control (open bars), LPS-induced chorioamnionitis (dark filled bars), and LPS-induced chorioamnionitis plus the IL-1 inhibitor, rhIL-1ra (light filled bars). Data are mean SEM, *p<0.05 between comparators.
Figure 5B:
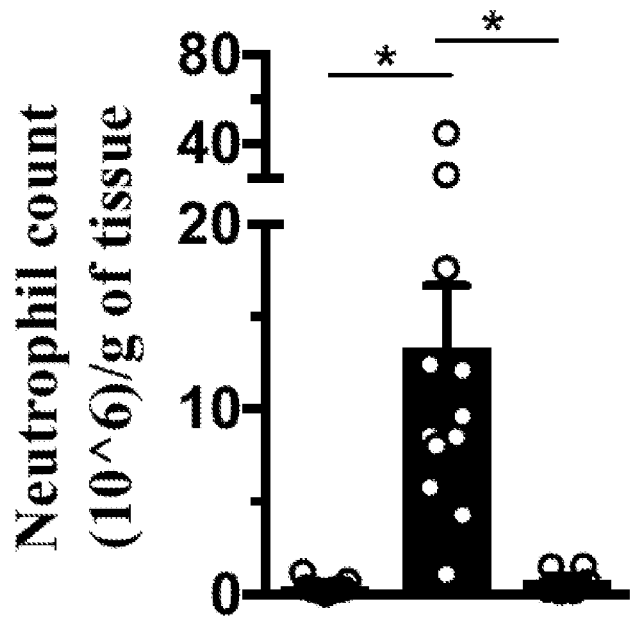
Figure 6:
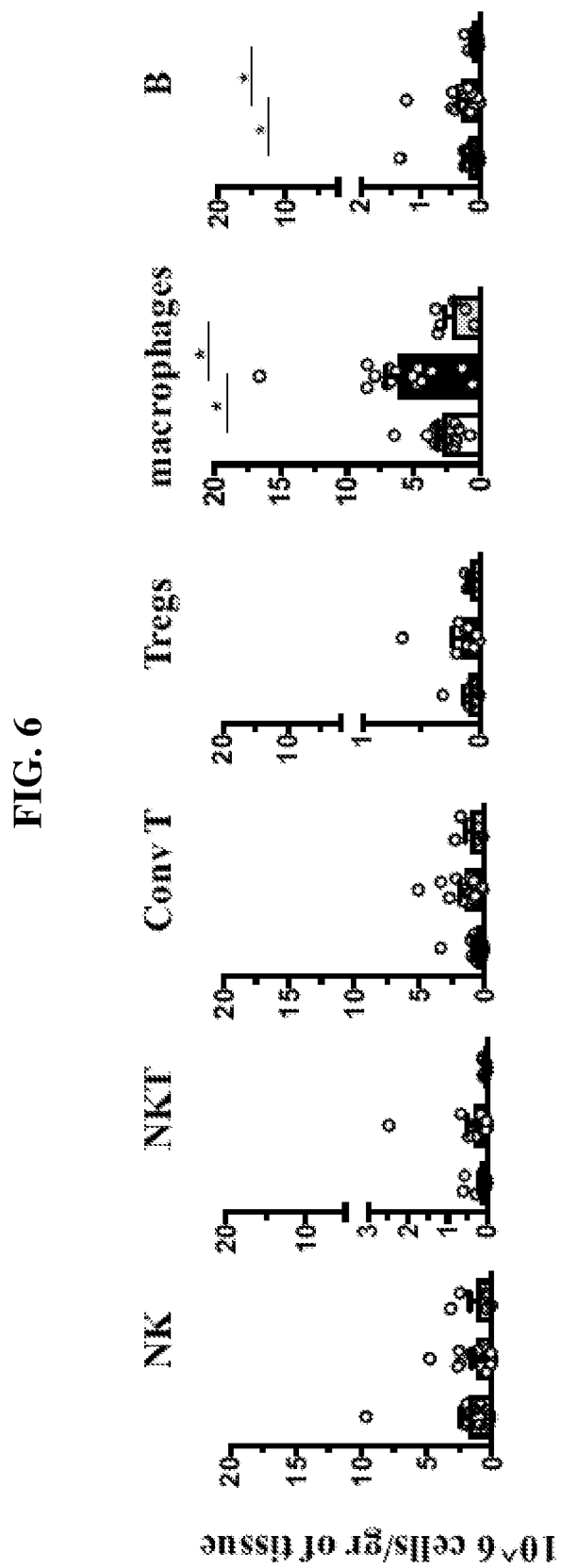
FIG. 6: IA LPS slightly increased macrophage and B-cells in the chorio-decidua in an IL-1-dependent manner. Control (open bars), LPS-induced chorioamnionitis (dark filled bars), and LPS-induced chorioamnionitis plus the IL-1 inhibitor, rhIL-1ra (light filled bars).

Flow cytometry analysis of chorio-decidua cell suspension showed that the frequency and numbers of neutrophils increased (~37 fold) upon IA LPS injection (FIGS. 5A-B). rhIL1ra reversed the neutrophil accumulation in the CD. Overall chorio-decidua CD45$^+$ cell counts increased ~4.5 fold upon IA LPS injection with little change in the CD45$^-$ cell counts (data not shown). rhIL-1ra decreased overall CD leukocyte counts (data not shown). Chorio-decidua cell suspensions were analyzed by multi-parameter flow cytometry and IA LPS exposure increased only the number of chorio-decidua macrophages and B cells compared to the control animals and rhIL1ra reverted macrophage and B-cell numbers to control levels (FIG. 6). LPS had no impact on NK, NKT, conventional T-cell or Treg (defined as CD3$^+$, CD8$^-$, FOXP3$^+$ cells) numbers. (Data are mean, SEM, *$p<0.05$ between comparators). In contrast to neutrophils, IA LPS did not significantly change the number of CD NK cells, NKT cells, conventional CD4$^+$T-cells, or regulatory T-cells, while it slightly increased the number of macrophages and B-cells (~2 fold and ~1.5 fold, respectively; FIG. 6). Interestingly, rhIL1ra also decreased LPS induced increases in macrophage and B-cell numbers to control levels.

rhIL1Ra Blocks CD Neutrophil Activation

Figure 7A:
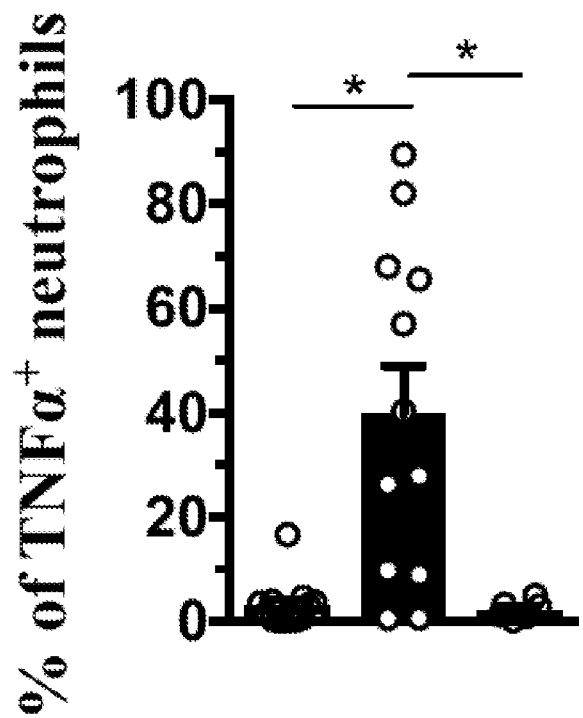
FIGS. 7A-E: IA LPS-induced chorio-decidua neutrophil cytokine production and activation is IL-1 dependent. (A) Expression of TNFα in chorio-decidua neutrophils was assessed by flow cytometry. rhIL1ra significantly decreased the frequency of TNFα+ chorio-decidua neutrophils. (B) Cell count/high powered field (HPF, 40×) of IL8$^+$ neutrophils in the chorion-decidua interface. Expression of activation molecules in chorio-decidua neutrophils was assessed by flow cytometry. rhIL1ra decreased LPS induced expression of (C) CD16 and (D) CD63 in chorio-decidua neutrophils. Control (open bars), LPS-induced chorioamnionitis (dark filled bars), and LPS-induced chorioamnionitis plus the IL-1 inhibitor, rhIL-1ra (light filled bars). (E) Positive correlation of CD63 expression and TNFα in neutrophils from LPS-exposed animals ($r^2$=0.69; p=0.03). (Data are mean, SEM, *p<0.05 between comparators).
Figure 7B:
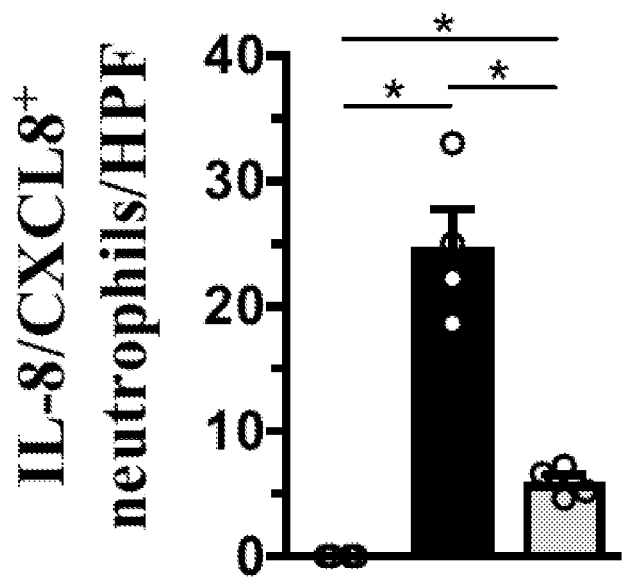
Figure 7C:
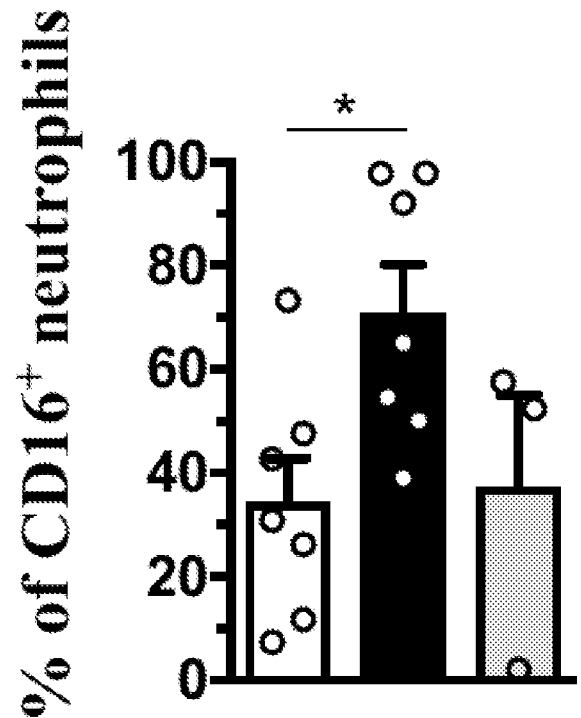
Figure 7D:
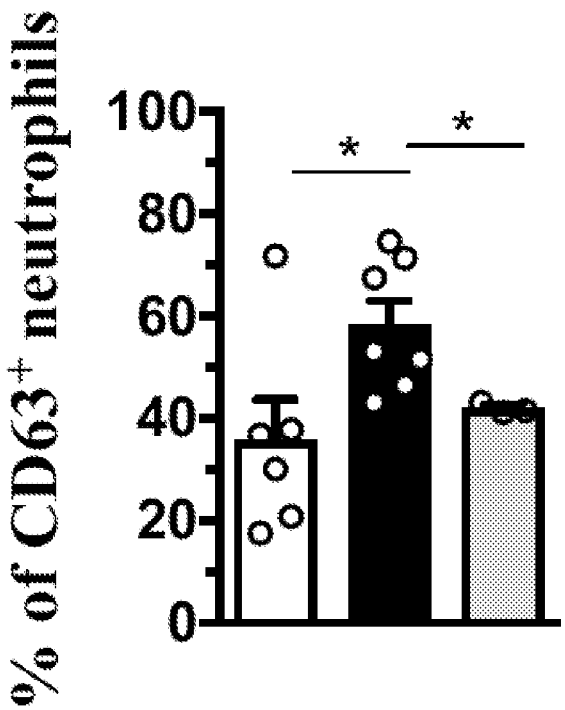
Figure 7E:
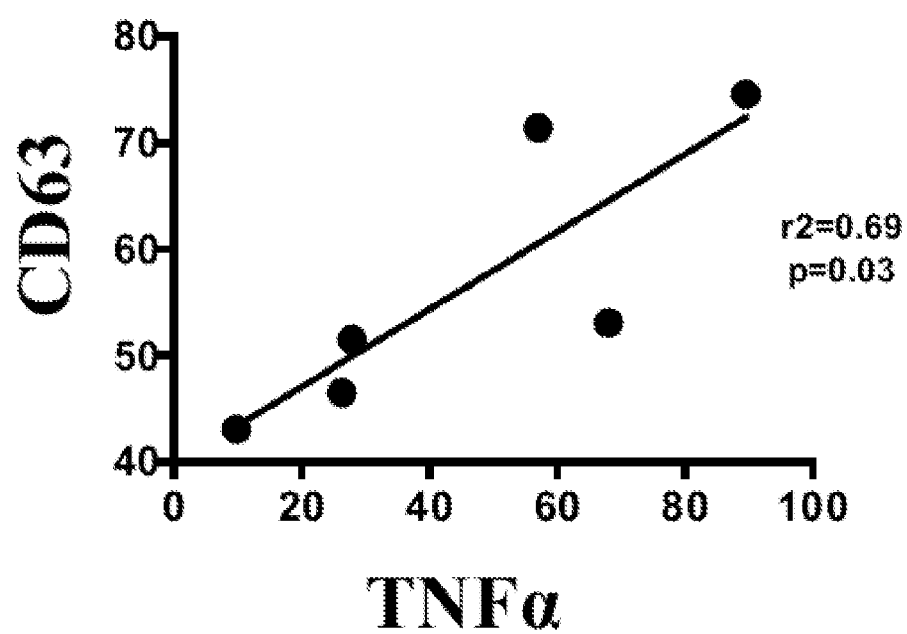
Figure 8:
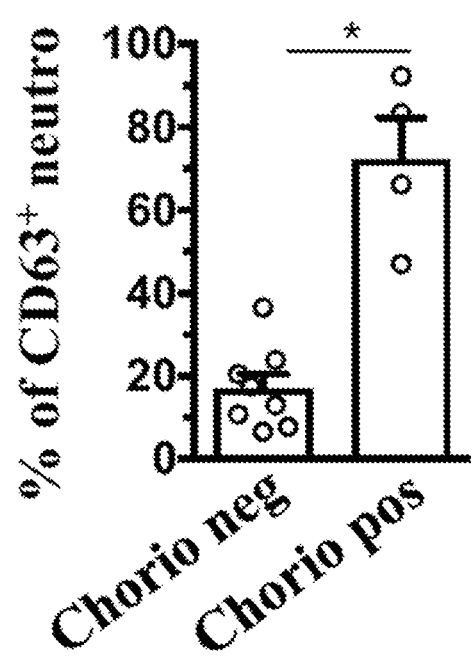
FIG. 8: Increased CD63 expression in chorio-decidua neutrophils during human chorioamnionitis. Similarly to Rhesus monkey, human chorio-decidua neutrophils from pre-term chorioamnionitis-positive samples expressed higher CD63 compared to neutrophils from pre-term chorio-negative samples. (Data are mean, SEM, *p<0.05 between comparators).

IA LPS increased the frequency of TNFα$^+$ CD neutrophils, which was reversed by rhIL1ra (FIG. 7A). Neutrophils were the major producers of TNFα among leukocyte subpopulations in the CD (data not shown). rhIL1ra decreased IA LPS induced CD neutrophils expressing CXCL8 (FIG. 7B). IA LPS increased both CD16 (FcRIII) (FIG. 7C) and CD63 (marker for release of azurophilic granules; FIG. 7D) expressing CD neutrophils, and rhIL1ra decreased both CD16 and CD63 expression to near control levels. CD63 expression highly correlated with TNFα expression in the neutrophils ($r^2=0.69$, $p=0.03$; FIG. 7E). Interestingly, human CD neutrophils from cases with chorioamnionitis had increased CD63 expression compared to CD neutrophils from no chorio cases (FIG. 8).

IA LPS Induced a CD Neutrophil Pro-Survival Program Mediated by BCL2A1

Figure 9A:
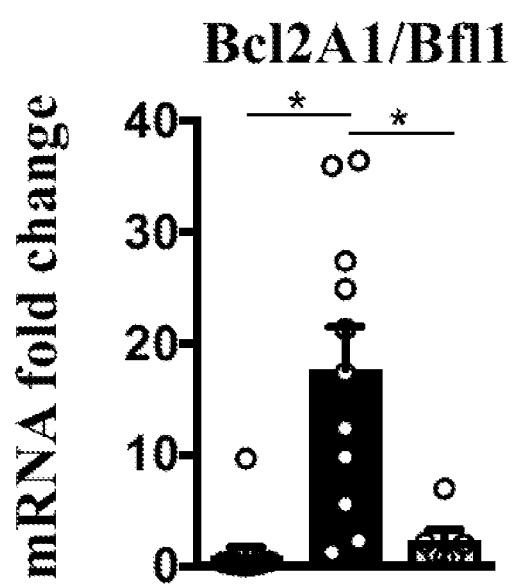
FIGS. 9A-D: IA LPS-induced expression of the pro-survival factor BCL2A1/BFL1 in neutrophils is IL-1-dependent. (A) Expression of BCL2A1/BFL1 mRNA by quantitative PCR in the Rhesus CAD, control (open bars), LPS-induced chorioamnionitis (dark filled bars), and LPS-induced chorioamnionitis plus the IL-1 inhibitor, rhIL-1ra (light filled bars). (B) Cell count/high powered field (HPF, 40×) of cells in the chorio-decidua interface showing fewer BCL2A1+neutrophils in LPS+rhIL-1ra compared to LPS groups. (C) Increased expression of BCL2A1/BFL1 and BCL-xl in flow-sorted chorio-decidua neutrophils from IA LPS-exposed animals compared to immune-magnetic bead-purified blood neutrophils from the same animal, blood neutrophils (open bars), decidua neutrophils (dark filled bars). (D) Chorio-decidua cell suspensions were cultured for 16 hr. ML214 treatment (5 mM) decreased frequency of choria-decidua AnnexinV$^-$/7aad$^-$ (non-apoptotic) neutrophils by flow cytometry, while ABT-737 (0.1 mM) did not show any significant effect. (Data are mean, SEM, *p<0.05 between comparators).
Figure 9B:
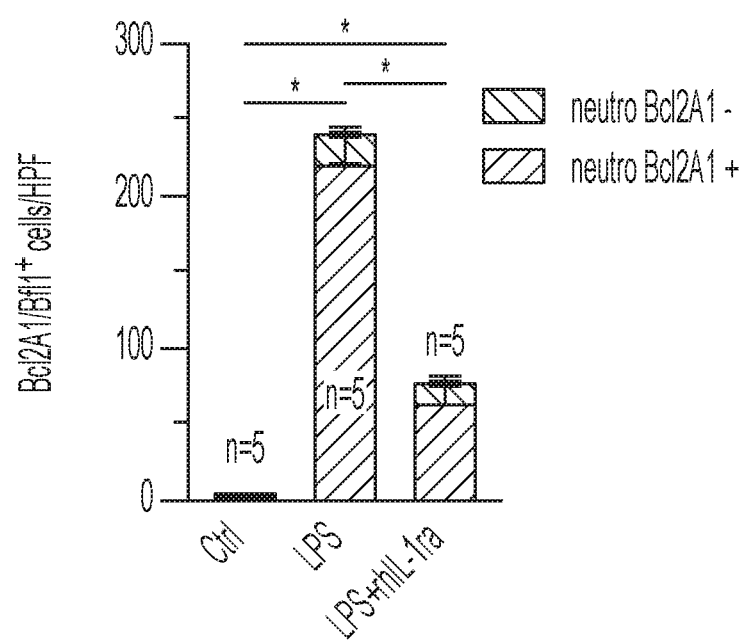
Figure 9C:
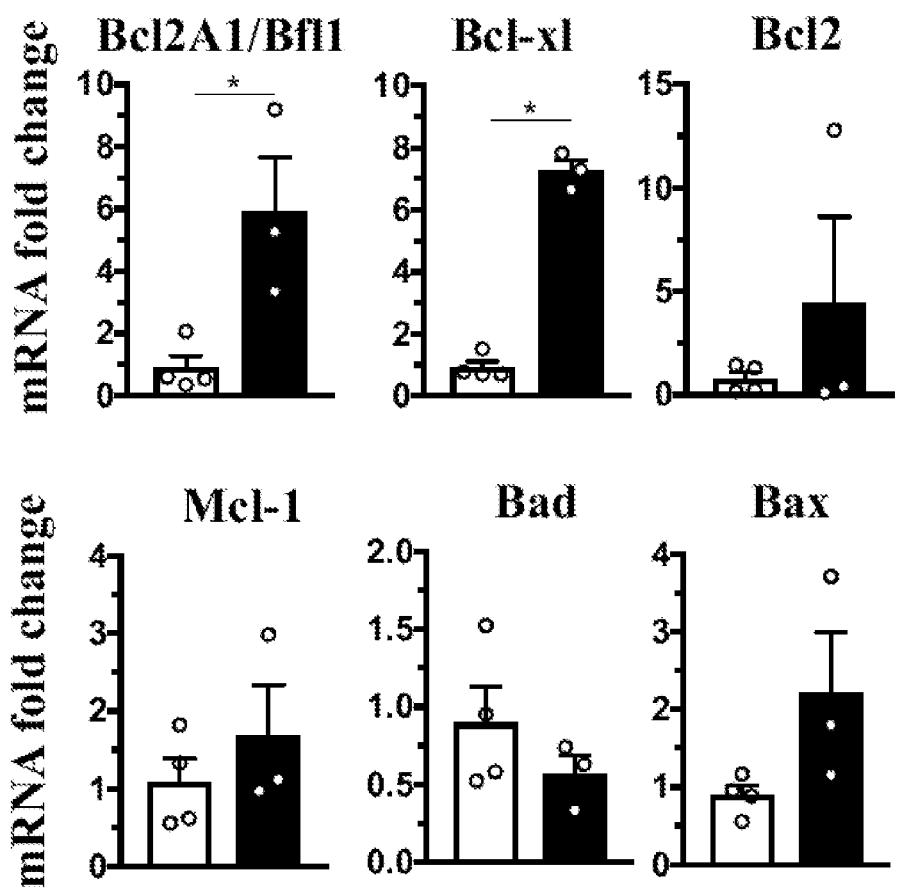
Figure 9D:
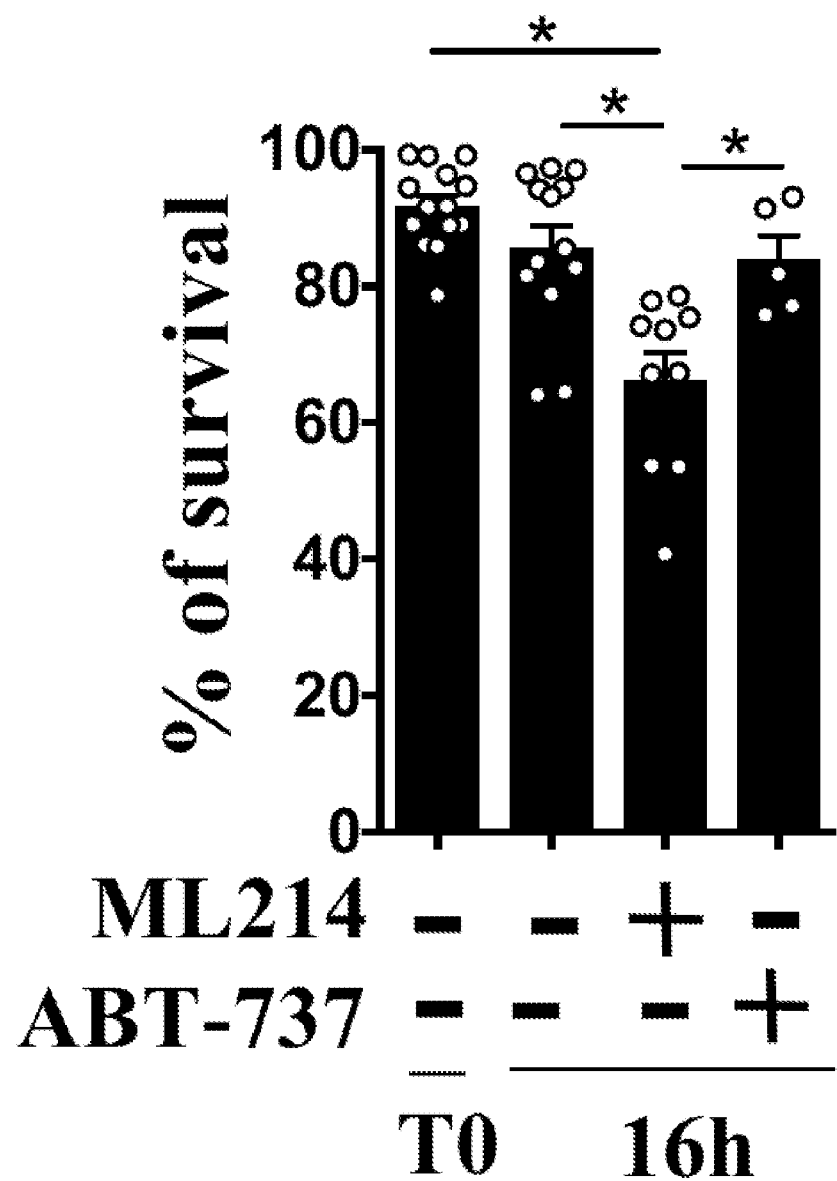
Figure 10:
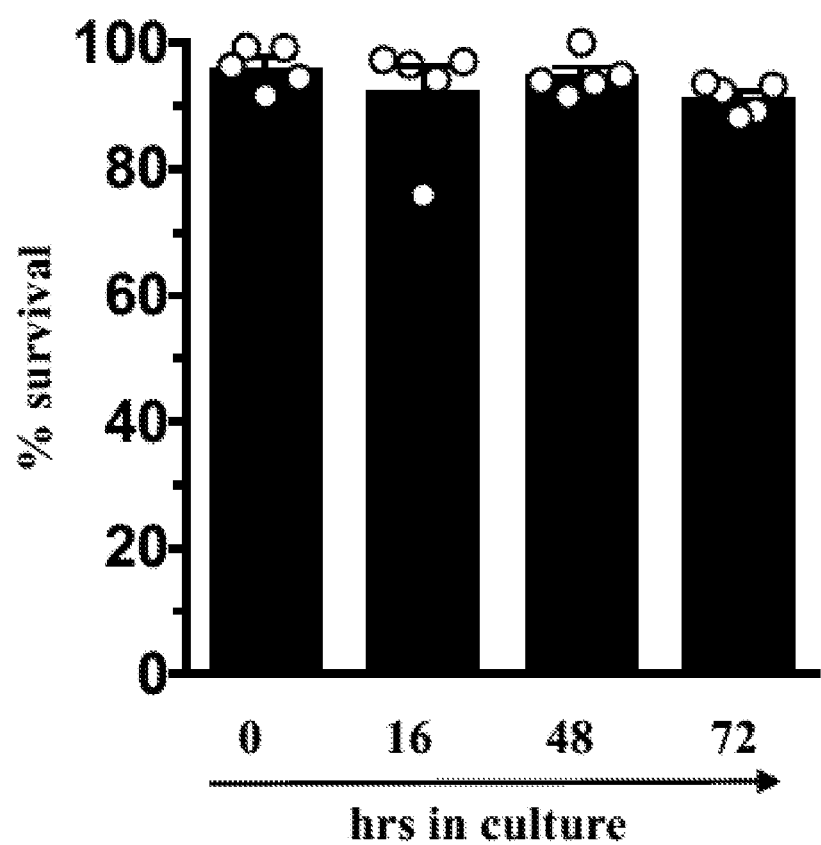
FIG. 10: Prolonged chorio-decidua neutrophil survival. Chorio-decidua cells isolated from IA LPS-exposed animals were cultured without any stimulation for the time indicated. Chorio-decidua neutrophil survival (Annexin V$^-$/7aad$^-$) was assessed by flow cytometry. (Data are mean, SEM).
Figure 11:
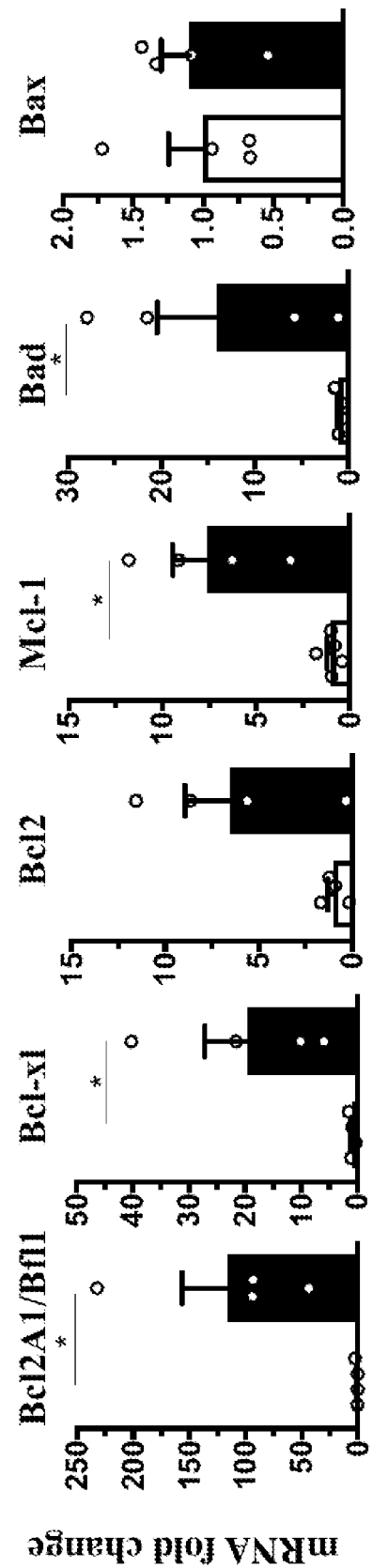
FIG. 11: Chorioamnionitis-induced expression of the pro-survival factor BCL2A1/BFL1 in human chorio-decidua neutrophils. Human immuno-magnetic bead purified chorio-decidua neutrophils from pre-term chorioamnionitis-positive cases showed a significant increase of anti-apoptotic BCL2A1/BFL1, Bcl-xl, and Mcl-1, and pro-apoptotic Bad compared to blood neutrophils from adult healthy women. Blood neutrophils from adult healthy women (open bars), chorio-decidua neutrophils from preterm chorioamnionitis-positive (dark filled bars). Data are mean, SEM, *p<0.05 between comparators.

To understand transcriptomic changes, we analyzed highly upregulated genes in the maternal-fetal membranes during chorioamnionitis. Table 2 shows the ten most highly upregulated genes in the Rhesus and human chorioamnion-decidua. Bcl2A1 (referred to as Bfl1 in humans) is an inhibitor of apoptosis and was one of the highly upregulated genes common to Rhesus and humans. rhIL1ra reversed the increased CAD expression of Bcl2A1 in LPS-exposed animals (FIG. 9A). Importantly, Bcl2A1 was specifically expressed by CD neutrophils, and rhIL1ra decreased BCL2A1+neutrophils (FIG. 9B). Neutrophil expression of Bcl2A1 could be constitutive or induced. Since control CAD tissue have very few neutrophils, we compared expression of Bcl2A1 and other important mediators of apoptosis in CD neutrophils vs. blood neutrophils from the same IA LPS-exposed animals. Among anti-apoptosis mediators, the expression of Bcl2A1 and Bcl-xl was higher but Bcl2 and Mcl1 expression did not change in CD neutrophils. The expression of pro-apoptosis mediators Bad and Bax also did not change in CD neutrophils (FIG. 9C). Chorio-decidua neutrophil survival was significantly increased compared to that of blood neutrophils after 16 h of culture (86±3%, n=13, CD, versus 45±5%, n=10, blood, (p<0.05). We also observed an extended survival of CD neutrophils cultured for 72 h (FIG. 10). Increased expression of Bcl2A1 in chorio-decidua neutrophils compared to blood neutrophils was also confirmed in humans (FIG. 11). To identify the specific contribution of BCL2A1, we compared CD neutrophil survival in culture after chemical of inhibition of BCL2A1 using ML214 (Bittker et al., 2010) vs. inhibition of BCL2 using ABT-737 which does not inhibit BCL2A1 (Vogler et al., 2009) (FIG. 9D). ML214 but not ABT-737 decreased CD neutrophil survival (FIG. 9D), demonstrating the importance of BCL2A1 in mediating CD neutrophil survival.

rhIL1ra Reduced IA LPS Induced Intrauterine Inflammation

Figure 12:
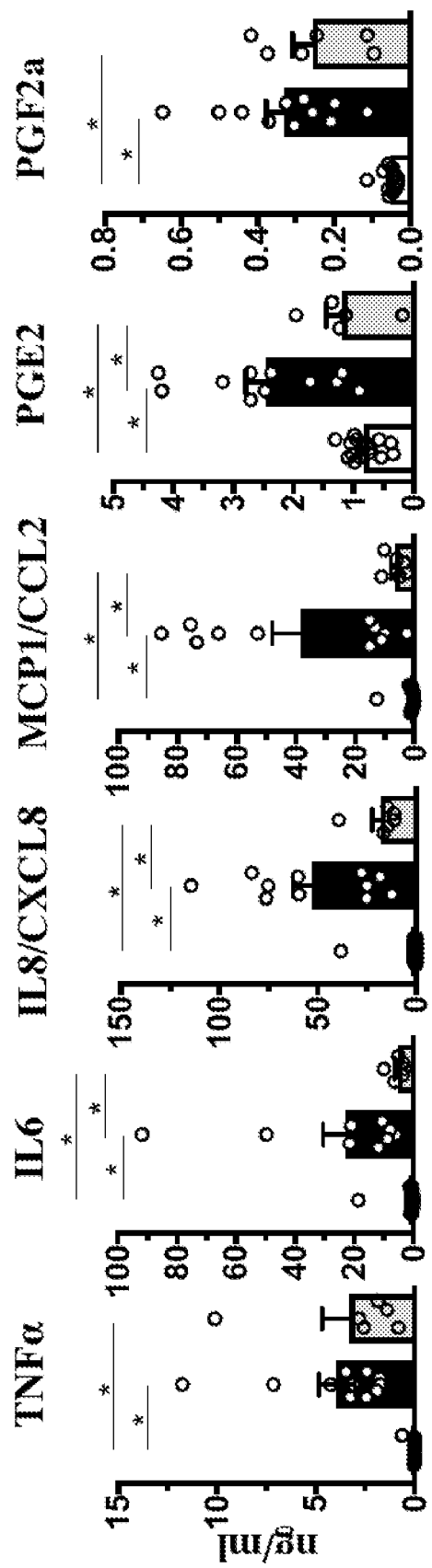
FIG. 12: IL-1R blockade showing a decrease in inflammatory markers in amniotic fluid in IA LPS-exposed animals. Cytokine concentrations, TNFα, IL-6, IL-8/CXCL8, MCP1/CCL2, PGE2, and PGF2a, were measured by multiplex ELISA. Prostaglandin (PG) concentrations were measured in lipid extract of amniotic fluid by ELISA. Control (open bars), LPS-induced chorioamnionitis (dark filled bars), and LPS-induced chorioamnionitis plus the IL-1 inhibitor, rhIL-1ra (light filled bars).

NK cells, macrophages, and T-cells that are abundant in third trimester primate decidua can potentially cause intrauterine inflammation without contributions from neutrophils Gomez-Lopez et al., 2014). Amniotic fluid concentrations of Prostaglandins (PG) and cytokines, particularly IL6, are validated biomarkers of inflammation induced preterm labor (Combs et al., 2014; Romero et al., 2014; Romero et al., 2015). rhIL1ra decreased LPS induced amniotic fluid concentrations of IL6, CXCL8, MCP1, and PGE2, but not TNFα or PGF2a (FIG. 12).

tory mediators associated with preterm labor in a manner that demonstrates a broad multi-compartment anti-inflammatory effect.

Figure 13:
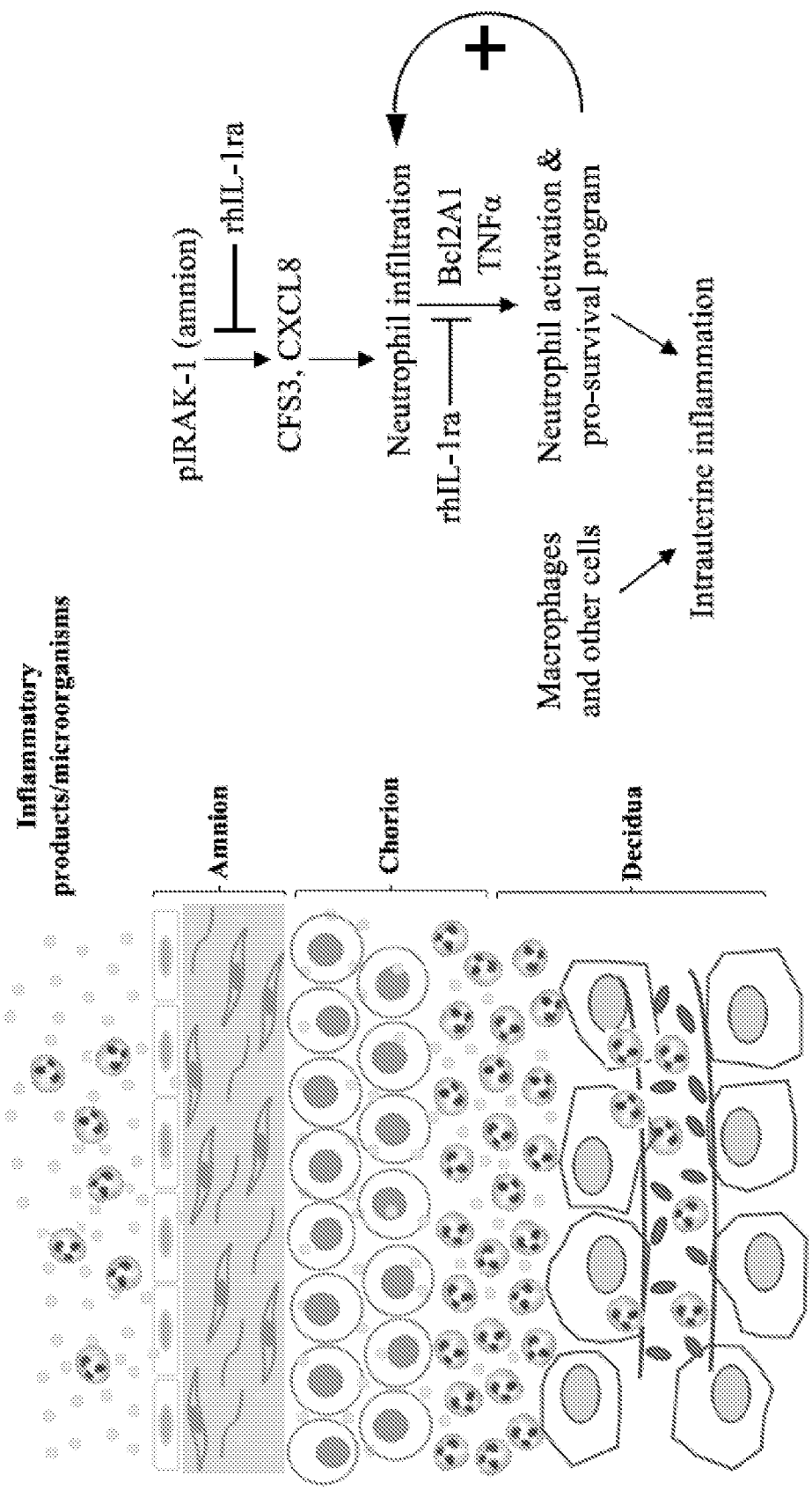
FIG. 13: Schematic representation of the upstream signals resulting in neutrophil infiltration and the resulting amplification of inflammation as the maternal-fetal interface.

Our findings are consistent with a model, illustrated in FIG. 13, in which, during IUI, pro-inflammatory mediators signal the amnion tissue to activate the IRAK pathway which results in the secretion of neutrophil chemoattractants. This in turn leads to neutrophil infiltration and amplifies inflammation at the maternal-fetal interface.

Inflammation at the maternal-fetal interface involves both fetal tissues (amnion and chorion) and maternal tissue (decidua). Leukocytes comprise about 70% of all chorio-decidua cells in the third trimester in both human and Rhesus (data not shown). Most of the leukocytes are macrophage, NK cells or T-cells. During chorioamnionitis, we observed a minimal increase in non-neutrophil chorio-decidua leukocytes.

Infiltrating neutrophils at the chorio-decidua are known to be of maternal origin while those in the amniotic fluid are largely of fetal origin. IA LPS resulted in neutrophil accumulation primarily in the chorio-decidua (neutrophil counts were about 10-fold higher in the chorio-decidua compared to AF neutrophils). Blocking IL-1R via rhIL1ra reduced chorio-decidua neutrophil numbers by ~90%.

During IUI, the amnion can be potentially signaled by mediators in the amniotic fluid or from the basal side by the chorio-decidua. Since microbial products can be identified in the amniotic fluid in only ~30% of human IUI cases even

TABLE 2 mRNASeq analysis showing top ten differentially expressed during chorioamnionitis.

| Rhesus | | | Human | | |
|---|---|---|---|---|---|
| | | | | | Pre-term chorio |
| Gene | Gene Function | LPS vs. ctrl (fold ↑) | Gene | Gene Function | pos vs. preterm chorio neg (fold ↑) |
| DEFB2L | β-Defensin 2 | 112 | PI3 | Peptidase inhibitor 3 | 201 |
| CXCL13 | C-X-C Motif Chemokine Ligand 13 | 98 | G0S2 | G0/G1 Switch 2 | 106 |
| CLEC4D | C-Type Lectin Domain Family 4 Member D | 44 | BCL2A1 | BCL2 Related Protein A1 | 73 |
| C19orf59 | Mast Cell Expressed Membrane Protein 1 | 41 | IL8 | Interleukin 8 | 63 |
| S100A9 | S100 Calcium Binding Protein A9 | 39 | S100A8 | S100 Calcium Binding Protein A8 | 61 |
| MYH15 | Myosin Heavy Chain 15 | 39 | S100A12 | S100 Calcium Binding Protein A12 | 60 |
| LTB4R | Leukotriene B4 Receptor | 35 | ORM1 | Orosomucoid 1 | 44 |
| NAPSA | Napsin A Aspartic Peptidase | 35 | FDCSP | Follicular dendritic cell secreted protein | 33 |
| CSF3R | Colony Stimulating Factor 3 Receptor | 31 | HLA-A | Major Histocompatibility Complex, Class I, A | 32 |
| BCL2A1 | BCL2 Related Protein A1 | 29 | CHI3L1 | Chitinase 3-like 1 | 29 |

Discussion

In summary, we found that IL-1 blockade decreased the expression of several inflammatory mediators both in the amnionic fluid and in the maternal-fetal membranes, while also decreasing neutrophil accumulation in the chorio-decidua and the expression of inflammatory mediators in that compartment. Thus, the IL-1 blockade decreased inflammawith sensitive molecular detection methods, the compartmental location of inflammatory signals is not known in humans. Our finding that IRAK1 is phosphorylated in both the Rhesus model and human chorioamnionitis patients suggests that that activation of IRAK1 is a general phenomenon in the cascade of IUI.

IL-1R blockade resulted in decreased LPS-induced TNFalpha, CXCL8, CD63 and CD16 expression in the neutrophils. CD63 is critical in processing and secretion of neutrophil elastase. CD16 expression is induced by TNFα and mediates phagocytosis of immune complexes. CXCL8 production by neutrophil likely creates a feed-forward loop of more neutrophil recruitment and amplification of inflammation at the maternal-fetal interface. These results demonstrate that IL-1 signaling mediates both neutrophil recruitment and a broad program of neutrophil activation at the maternal-fetal interface. Amniotic fluid levels of IL-6 and prostaglandins (PG) are validated biomarkers of inflammation mediated preterm labor. IL-1 blockade effectively decreased LPS induced increases in both amniotic fluid (AF) IL6 and PGE2. In addition, IL-1 blockade decreased AF levels of TNFα, IL1ß and other pro-inflammatory agonists.

Neutrophils normally have a life-span of a few hours in the circulation regulated by apoptosis. However, tissue neutrophils exposed to pro-inflammatory stimuli are known to have longer life-span. Our data further demonstrate that decidua neutrophils depend on BCL2A1/Bfl1 for their survival, but specifically in response to pro-inflammatory stimuli. Importantly, BCL2A1-deficient mice do not have defects in basal neutrophil homeostasis. BCL2A1/Bfl1 is therefore a promising therapeutic target in the treatment and prevention of chorioamnionitis at pre-term birth, as well as other diseases and disorders characterized by neutrophil-mediated inflammation.

Methods

Animals

All animal procedures were approved by the Institutional Animal Care and Use Committee at the University of California, Davis. Normally cycling, adult female rhesus macaques (*Macaca mulatta*) (n=43) were time mated. At ~130 d of gestation (~80% of term gestation), the pregnant rhesus received either 1 ml saline solution (n=16) or 1 mg LPS (Sigma-Aldrich, St. Louis, Mo.) in 1 ml saline solution by ultrasound-guided IA injection. Dams were surgically delivered 16 h (n=13) or 48 h (n=8) later. Multiparous macaques and their fetuses were similar in demographics (Table 4). After delivery, fetuses were euthanized with pentobarbital, and fetal tissues were collected. There were no spontaneous deaths or preterm labor in the animals. IL-1 signaling was blocked by recombinant human IL-1R antagonist (rhIL-1RA; Anakinra Sobi, Stockholm, Sweden) given to the pregnant monkey IA (50 mg) and subcutaneous (100 mg) 1 and 3 h before LPS, as previously described (Rueda et al., 2016; FIG. 3).

Human Samples

Pregnant women with pregnancies 26⁰ and 36⁶ weeks and admitted for imminent delivery provided informed consent from 2014 to 2017 under a protocol approved by the Institutional Review Boards (IRB s) of Cincinnati Children's Hospital and University of Cincinnati (#2013-2243). Cohorts were developed based on a detailed histo-pathologic diagnosis of chorioamnionitis based on Redline's criteria (Redline et al., 2003). Maternal and neonatal demographic characteristics of the cohorts are shown in Table 3.

TABLE 3

Clinical characteristics of animals included in the study.
"IA" refers to "intra-amniotic"

| Cohort | IA Saline (Ctrl) n = 16 | IA LPS 16 h (n = 13) | IA LPS + rIL-1ra 16 hr (n = 6) | IA LPS 48 h (n = 8) |
|---|---|---|---|---|
| Maternal age, year ± SD | 10 ± 2.1 | 7 ± 1.8 | 8.5 ± 2.6 | 9.9 ± 2.6 |
| Maternal weight (Kg) | 8.9 ± 1.5 | 8.3 ± 1.7 | 10.3 ± 1.2 | 9.2 ± 0.8 |
| Median GA at delivery, days [range] | 131 [128-136] | 132 [128-137] | 132 [128-138] | 132 [126-137] |
| Mean birth weight, gram ± SD | 332.3 ± 27.2 | 323.6 ± 36.9 | 353.9 ± 32.1 | 319.3 ± 46.5 |
| Fetal gender number (F/M) | 8/8 | 9/4 | 3/3 | 1/7 |

TABLE 4

Clinical characteristics of pregnant women who delivered pre-term newborns. PTL: pre- term labor; PIH: pregnancy-induced hypertension; HTN: hypertension

| Cohort | Preterm chorio negative (n = 16) | Preterm chorio positive (n = 14) | P value |
|---|---|---|---|
| Maternal age, year ± SD | 28.3 ± 2.67 | 29 ± 7.07 | 0.8 |
| Median GA at delivery, weeks [range] | 32.3 [26.6-35.4] | 31.4 [29.1-34] | 0.9 |
| Causes of pre-term birth | | | |
| PTL or preterm-PROM | 8/16 | 12/14 | 0.06 |
| Pre-eclampsia | 3/16 | 2/14 | 1.0 |
| Other indications | 5/16 | 0/14 | 0.04 |
| Antenatal steroid use | 11/16 | 12/14 | 0.4 |
| Antenatal antibiotics use | 4/16 | 10/14 | 0.03 |
| Cesarean delivery | 10/16 | 6/14 | 0.5 |
| The presence of labor | 8/16 | 12/14 | 0.06 |
| Spontaneous labor | 5/8 | 9/12 | 0.6 |
| Neonatal male gender | 7/16 | 8/14 | 0.7 |
| Mean birth weight, gram ± SD | 1690 ± 617 | 1880 ± 375 | 0.2 |
| White Caucasian race | 7/16 | 9/14 | 0.3 |
| African-American race | 9/16 | 5/14 | 0.3 |

Chorion, Amnion, Decidua Tissue Preparation

Both Rhesus and human purified decidua cell suspensions were prepared as previously described (Presicce et al., 2015). Briefly, extra-placental membranes were dissected away from the placenta. Decidua cells were scraped from the amnion-chorion. Amnion was then separated from chorion and flash-frozen for protein and RNA studies. Decidua tissue was washed, and digested with Dispase II (Life Technologies, Grand Island, N.Y.) plus collagenase A (Roche, Indianapolis, Ind.) for 30 min followed by DNase I (Roche) treatment for another 30 min. Cell suspensions were filtered subjected to Red blood cell lysis and prepared for flow cytometry. Viability was >90% by trypan blue exclusion test.

Flow Cytometry

Commercially available monoclonal antibodies (mAbs) were used for multiparameter flow cytometry (LSR Fortessa 2, BD Biosciences, San Diego, Calif.) and immunophenotyping was done on fresh chorio-decidua cell suspensions, except for T-cell phenotyping, which was done on cultured cells since cell isolation procedure down-regulates CD4/8 expression. Chorio-decidua cell TNFα expression was measured by flow cytometry with anti-TNF Ab (Cytofix/Cytoperm; BD Bioscience). To measure cytokine expression induced by in vivo exposures, flow cytometry was done on cells immediately after isolation without any stimulation and/or intracellular blockers. For all protocols, cells were treated with 20 mg/mL human immunoglobulin G (IgG) to block Fc receptors, stained for surface markers for 30 min at 4° C. in PBS, washed, and fixed in fixative stabilizing buffer (BD Bioscience). All antibodies were titrated for optimal detection of positive populations and mean fluorescence intensity. At least 500,000 events were recorded for each sample. Doublets were excluded based on forward scatter properties, and dead cells were excluded using LIVE/DEAD Fixable Aqua dead cell stain (Life Technologies). Unstained and negative biological population were used to determine positive staining for each marker. Data were analyzed using FlowJo version 9.5.2 software (TreeStar Inc., Ashland, Oreg.).

Neutrophil Isolation and RNA Extraction

Peripheral blood neutrophils were isolated from both Rhesus dams and female young healthy donors (median age 32 years; range 28-42 years) using human MACSxpress neutrophil isolation kit (Miltenyi Biotec, Auburn, Calif.), according to the manufacturer's instructions. Neutrophil purity was >97%, as assessed by flow cytometry. Rhesus chorio-decidua neutrophils and CD45$^-$ cells were purified by FACSAria Cell Sorter (BD Bioscience), using the same gating strategy as immunophenotyping studies. Neutrophil as well as CD45$^-$ cell purity was >98% (not shown). Human chorio-decidua neutrophils were purified by positive selection using anti-CD66b MicroBeads (Miltenyi Biotec). Total RNA was extracted from the purified neutrophils (2-4×10$^1$\6) by adding TRIzol (Thermofisher Scientific) and subsequently using Direct-Zol RNA MicroPrep kit (ZYMO Research, Irvine, Calif.) to efficiently extract small quantities of RNA.

Apoptosis Experiments

Neutrophils were cultured overnight (16 h) at 37° C., in 5% $CO_2$ in DMEM:F12 containing 10% fetal bovine serum, 100 IU/ml penicillin, 100 IU/ml streptomycin, and 2 mmol/L glutamine, in 24-well plate (1×10^6 cells/ml). Chorio-decidua cells were stained with a cocktail of Abs as above for immunophenotyping and analyzed by flow cytometry within 30 minutes and cell survival was indicated as percentage of Annexin V$^-$/7aad$^-$ cells (BD Bioscience).

Different concentrations of BCL2A1 inhibitor (ML214, NIH molecular libraries program) (Bittker et al., 2010) or BCL2 inhibitor that does not inhibit BCL2A1 (ABT-737) were used in the survival inhibition experiments. The chosen doses were optimum based on dose response curves that were generated using blood neutrophils. ABT737 concentrations ≥1 μM were toxic to the cells (not shown).

CXCL8 and Bcl2A1 Immuno-Histology

Immunofluorescence was performed as previously described (Presicce et al., 2015). Briefly, paraffin embedded Rhesus fetal membrane sections were sectioned, subjected to antigen-retrieval by microwave boiling in citrate buffer followed by incubation with either anti-human CXCL8 (product G265-8; 1:25 dilution; BD Biosciences), or BCL2A1 (product b450; 1:50 dilution; LSBio, Seattle, Wash.), in 10% normal horse serum/0.2% Tween-20 at 4° C. overnight. Staining was visualized using fluorescently labeled secondary antibodies (AF594; 1:200 dilution; Invitrogen) for 1 h at room temperature. Nuclear counterstain was achieved using Vector Shield Hard-Set mounting medium with 40, 6-diamidino-2-phenylindole (DAPI; Vector Labs).

Histologic Evaluation of Fetal Membranes for Chorioamnionitis

Hematoxylin and eosin (H & E) staining was performed for rhesus and human fetal membrane sections and photographed. H & E stained sections of human fetal membranes were scored in a blinded manner (by SGK) for chorioamnionitis using criteria outlined by Redline et al based on numbers and depth of neutrophil infiltration of the tissue (Redline et al., 2003).

Cytokines, Prostaglandin, Anakinra ELISA

Cytokine/chemokine concentrations in AF, fetal, and maternal plasma were determined by Luminex using non-human primate multiplex kits (Millipore). Lipids were extracted from the AF using methanol to measure Prostaglandins PGE2 (Oxford Biomedical Research, Oxford, Mich.) and PGF2a (Cayman Chemical, Ann Arbor, Mich.) concentrations. Anakinra (rhIL1ra) levels in AF, fetal, and maternal plasma were determined by human IL1ra/IL-1F3 Quantikine ELISA kit (R&D System, Minneapolis, Minn.). This kit has low cross-reactivity to Rhesus IL-1ra.

Quantitative RT-PCR and mRNA Sequence Analyses

Total RNA was extracted from neutrophils, snap-frozen chorioamnion-decidua, and amnion after homogenizing in TRIzol (Invitrogen). RNA concentration and quality were measured by Nanodrop spectrophotometer (Thermo-Scientific). Reverse transcription of the RNA was performed using Verso cDNA synthesis kit (Thermo-Scientific), following the manufacturer's protocol. Quantitative RT-PCR was carried out in a StepOnePlus real-time PCR system (Life Technologies) following standard cycling conditions. Quantitative RT-PCR assays were performed with rhesus- and human-specific TaqMan gene expression primers (Life Technologies). Eukaryotic 18S rRNA (Life Technologies) was endogenous control for normalization of the target RNAs, and a sample from an IA saline injected rhesus animal and a human chorio negative sample was used as the calibrator. The values were expressed relative to the average value of the control group. For mRNA seq analyses samples with RNA Integrity Number (RIN) ≥8.0 were used for mRNA sequencing. RNA-library preparation was performed at DNA core facility, Cincinnati Children's Hospital Medical Center. We used single-end read sequencing by Illumina HiSeq2500 Ultra-High-throughput sequencing system (Illumina Inc. San Diego, Calif., USA) at an average depth of 50 million reads per sample. Raw sequences were accepted once they passed the quality filtering parameters used in the Illumina GA Pipeline. Sequenced reads were mapped to the reference Rhesus monkey (*Macaca mulatta*) genome assembly MMUL1.0.

Western Blot

Both Rhesus and human amnion were peeled off the chorio-decidua layer. Tissue extracts were resolved through SDS-PAGE using 4%-12% separating gel (Invitrogen). Proteins were transferred to Hybond enhanced chemiluminescence (ECL) nitrocellulose membrane (Amersham Pharmacia Biotech) using a semi-dry transfer system (Bio-Rad) and blocked with 5% dried milk in PBS and 0.1% Tween-20 (MilliporeSigma). Blots were probed with anti-phospho IRAK1 antibody (BIOSS, bs-319R) or f3-actin antibody (MilliporeSigma, A5060) overnight at 4° C. Binding of HRP-labeled goat anti-rabbit antibody (sc-2004, Santa Cruz Biotechnology Inc.) was determined using SuperSignal-West Chemiluminescent Substrate (Thermo Fisher Scientific). Blots were stripped with Restore Western Blot Stripping Buffer (Thermo Fisher Scientific), as required. The blots were imaged and quantified using ImageJ software (NIH), and the results were reported as pIRAK1/f3-actin ratio.

Statistical Analyses and Study Approval

Prism version 5.0b software (GraphPad, La Jolla, Calif.) was used to analyze data. Values were expressed as means±SE. Mann-Whitney U tests (for non-normally distributed continuous variables and Student t test for Gaussian distributed data points) and Fisher's exact test for categorical variables were used to determine differences between groups. Results were considered significant for P values of ≤0.05. All animal procedures were approved by the IACUC at the UCD. Pregnant women provided a written informed consent from 2014-2017 under a protocol approved by the IRBs of Cincinnati Children's Hospital and University of Cincinnati (no. 2013-2243).

Example 2: BCL2A1/BFL1 Inhibitors

Figure 14:
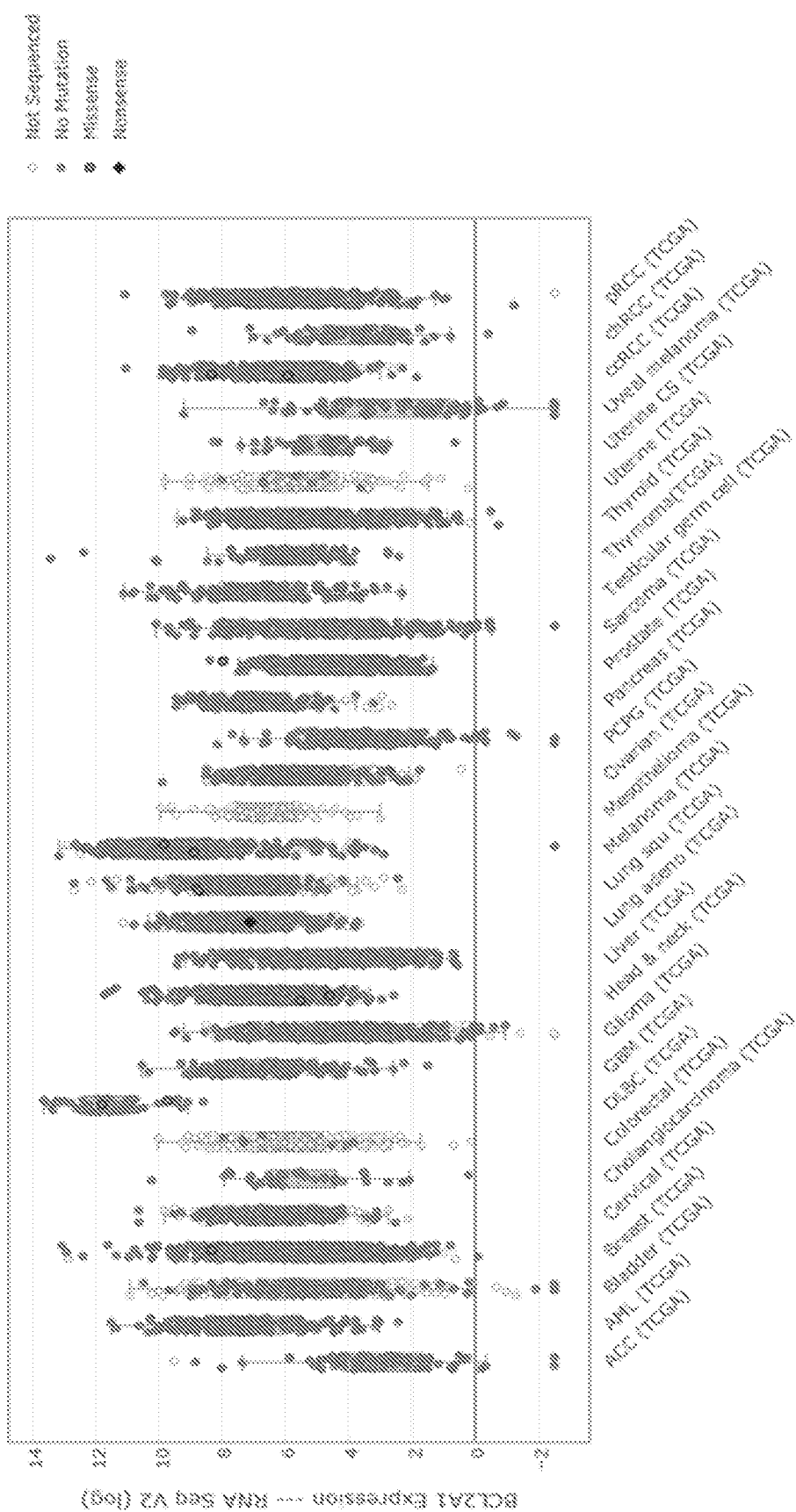
FIG. 14: Upregulation of BCL2A1 is observed across a wide range of cancers. BCL2A1 expression as observed in cBioPortal across a range of cancer datasets from the TCGA database reveals significant upregulation in a wide range of cancer cells.

The balance between cell survival and apoptosis is critical to the modulation of immune responses. As discussed in the preceding example, disruption of this balance underlies serious conditions such as intrauterine inflammation. In the preceding example we identified BCL2A1/BFL1 as critical to the survival of maternal neutrophils infiltrating the choriodecidua. Since these cells significantly contribute to amplification of inflammation at the maternal-fetal interface during intrauterine infection, inhibiting BCL2A1/BFL1 to deplete maternal neutrophils offers a promising target in the treatment of this and other diseases and disorders characterized by pathological inflammation. In addition, as shown by the analysis in FIG. 14, upregulation of BCL2A1/BFL1 is observed across a wide range of cancers, indicating that inhibitors of this protein can also be used, alone or in combination therapy, with other anti-cancer agents, for the treatment of diverse types of cancer. To date, no inhibitors specific to BCL2A1/BFL1 have been identified. Inhibitors that target the BCL2 protein family more generally are unable to effectively block BCL2A1/BFL1 activity. Here we describe the rational design of small molecule inhibitors of BCL2A1/BFL1.

Like other "pro-survival" members of the BCL2 family, BCL2A1/BFL1 mediates a pro-survival phenotype through sequestration of BH3-domain peptides which otherwise act as sensitizers to the cell-death promoting proteins Bax and Bak. To identify BCL2A1/BFL1 inhibitors, we first employed virtual screening to identify candidate small molecules predicted to interact with BCL2A1/BFL1 at the interface of its binding to BH3 and sterically block BH3 peptides from binding. The binding pocket is very highly conserved between the human and murine proteins. Of the 16 amino acid residues making up the pocket, 11 are identical and the remaining 5 are chemically similar, either isosteric (e.g., serine to cysteine) or all hydrophobic, e.g., isoleucine to leucine, phenylalanine to valine, tyrosine to cysteine, valine to isoleucine. Accordingly, we expect that any inhibitors identified as specific to this pocket will inhibit both the human and murine proteins.

These "virtual" screens identified 148 candidate inhibitors and were followed by in vitro biophysical characterization of their binding and activity. A number of compounds demonstrated inhibition of A1 and its associated BH3-domain peptides in differential scanning fluorimetry and thermal shift assays. Some of these compounds showed cooperative inhibition of BH3 binding when added in combination with BCL2A1 and labeled native binding protein. Additional compounds were identified from an orthogonal genomics screen using LINCS analysis, many of which were structural homologs of the hits from the original virtual screen. In summary, using a multi-stage virtual screening protocol coupled with experimental validation of top ranking candidates, we identified 13 molecules having significant activity in vitro from an initial pool of 90,086 candidates. Details are provided in the following sections.

The approach is summarized in FIG. 15, which depicts the overall strategy (FIG. 15A) and the results at each stage in the method (FIG. 15B). Starting with a subset of the NCI library, which consists of a total of 90,086 small molecules, candidate binding compounds were enriched in a virtual screen and characterized for binding and inhibition in vitro through thermal-shift assays and fluorescence polarization. Important hits in the biochemical screens were further characterized in vitro using primary splenocytes through a trypan blue cell-survival assay where a specific inhibitor was identified via Bax/Bak$^{-/-}$ cells. As an additional validation and alternative avenue to identify more candidate inhibitors, BCL2A1 knockdown signatures from the LINCS data consortium were used, and all chemical perturbagens that showed strong concordance with knockdown signatures were analyzed and compared to the set identified through a docking procedure.

Figure 16A:
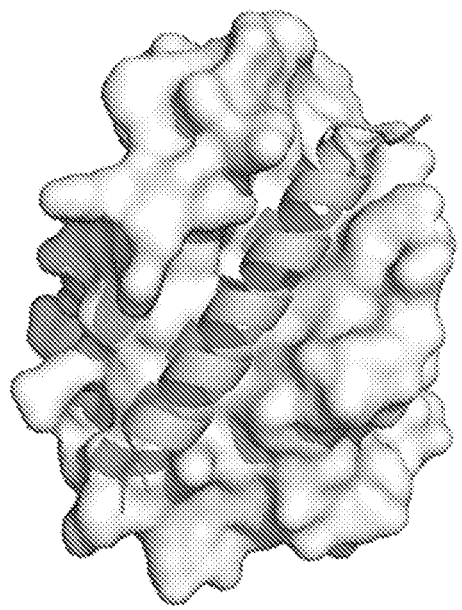
FIGS. 16A-D: Boxes for virtual screening of BCL2A1 and BFL1 targeting two pockets within the peptide binding groove. (A) (PDB:2VOH), the binding groove is highlighted by the BAK/BH3-domain peptide (ribbon) from BCL2A1 (white). Grid boxes for docking simulations are targeted to both mouse BCL2A1, A1 (B) (PDB:2VOH), and Human BCL2A1, BFL1 (C) (PDB:3MQP). Atoms within 4.5 Å of the BH3 ligand from each crystal structure are highlighted. Superposition of BCL2A1 with BCL2 (dark areas in D) (PDB: 5JSN) reveals significant differences within the P4 pocket (D). In this figure, the P2 pocket is displayed as the grid box (light, top box in 3B and 3C) and the P4 pocket is displayed as the grid box (dark, bottom box in B, C, and D).
Figure 16B:
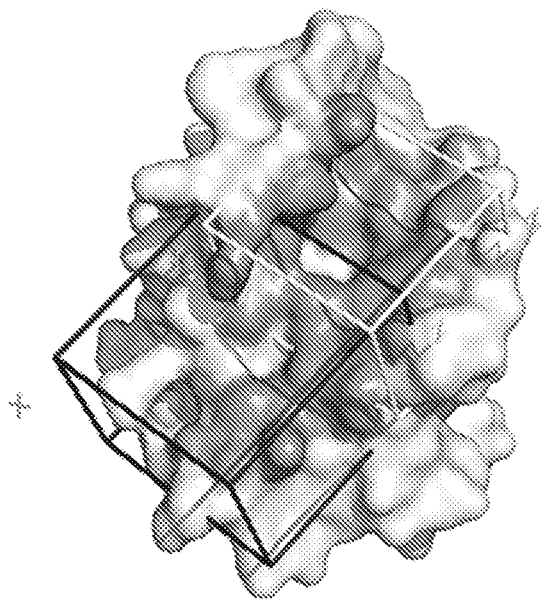
Figure 16C:
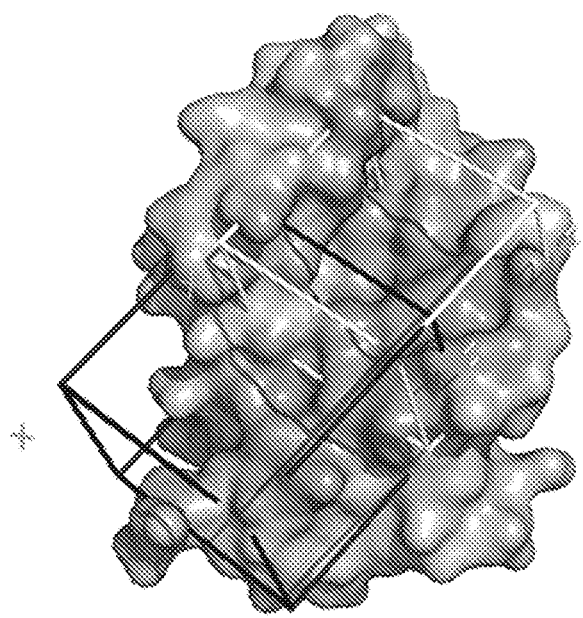
Figure 16D:
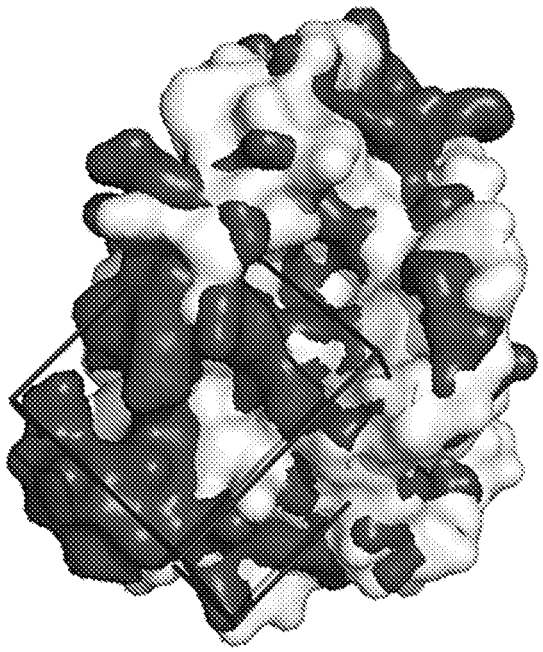

Both murine BCL2A1 and human BFL1 have been crystallized in the presence of several known and synthesized BH3-domain proteins. These include, for example, BID, PUMA, BAK, NOXA, BIM and BMF(PDBs: BFL1: 4ZEQ, 5UUK, 5UUL, 5UUP, 3I1H, 3MQP, 2VM6, A1: 5WHH, 5WHI, 2VOF, 2VOG, 2VOH, and 2VOI (Harvey et al., 2018; Smits et al., 2008; Jenson et al., 2017). Each shows a conserved hydrophobic pocket, referred to as the "P2" pocket, consistent with other members of the family (Zhai et al., 2008). The BH3-binding groove extends into a broad, shallow pocket in BCL2A1/BFL1, which is not present in other family members. This pocket therefore provides a unique surface for identifying and/or targeting small molecules with BCL2A1/BFL1 binding specificity, the "P4" pocket. Boxes for virtual screening of BCL2A1/BFL1 targeting two pockets within the peptide binding groove are shown in FIGS. 16A-D. The binding groove is highlighted by the BAK BH3-domain peptide (ribbon structure) (A). Grid boxes for docking simulations are targeted to both mouse (B), and human pockets (C). Atoms within 4.5 Å of the BH3 ligand from each crystal structure are identified. Superposition of BCL2A1 (white) with BCL2 (dark gray) shows that there are significant differences between these two molecules within the P4 pocket (D). In FIGS. 16B, 16C, and 16D, the P2 pocket is displayed as the white (upper) grid box and the P4 pocket is displayed as the black (lower) grid box.

Docking for the virtual screen was performed using mouse BCL2A1 protein (PDB: 2VOH) bound to the BAK/BH3-domain and human BFL1 (PDB: 3MQP) bound to the NOXA BH3-only peptide. This screen consisted of three iterations of docking of a subset of the NCI library to BCL2A1 and BFL1 in parallel. First, a drug-like subset of the NCI library consisting of 90,086 small molecules was docked to the P2 pocket of A1 with 250,000 evaluations. After docking to BCL2A1, the same library was used against the P2 pocket of BFL1. This pocket is conserved throughout the protein family and is a deep pocket in the center of the binding groove. It is expected that compounds targeted to this site could have a high-affinity interaction, since this is a deep pocket with several interacting residues. The compounds in the top 30,000 based on predicted inhibition constant from each run were collected and the intersection of top hits common to the BCL2A1 and BFL1 searches was used as the library in the subsequent round of docking. Two more rounds of docking were performed on the P2 pocket with increasing search depth on the reduced compound libraries with greater numbers of evaluations. This process was then repeated for the P4 pocket. After three rounds of docking for each pocket, the intersection of the top compounds left approximately 300 compounds per pocket. Compounds were further refined based on their entropy of pose clustering by removing any compounds that had Shannon Entropy of clustering above 0.5. Compounds were clustered by similarity of chemical moieties via Tanimoto Coefficient and representatives of each cluster were ordered for testing in vitro.

Thermal shift assays and fluorescence polarization competition assays were used to identify compounds that bind to BCL2A1/BFL1. Compounds were first tested for binding to BCL2A1 using differential scanning fluorimetry (DSF) thermal shift assays. DSF measures the midpoint temperature ($T_m$) for thermal denaturation of proteins; typically ligand binding stabilizes the protein fold, resulting in an increased $T_m$. During DSF experiments, all compounds that contributed to an increase in $T_m$ that corresponded to at least three standard deviations from the mean were included in further assays. Additionally, any compounds that showed a decrease in polarization of three or more standard deviations from the mean and those that were derived from early compounds with measurable $IC_{50}$ values were included for further dose response studies.

Figure 17A:
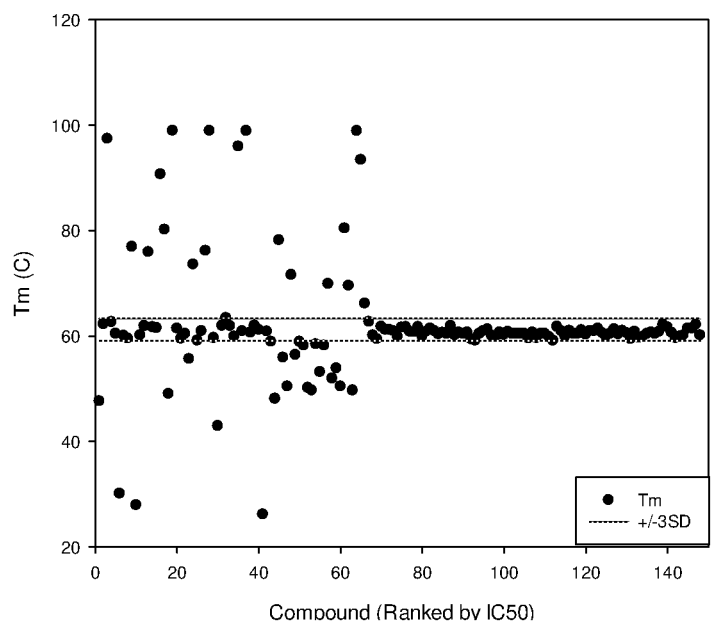
FIGS. 17A-B: (A) High-dose differential scanning fluorimetry (DSF) and (B) fluorescence polarization (FP) experiments were performed in parallel to further reduce the overall number of compounds to be tested. DSF and FP were performed with 100 μM of each compound for binding or NOXA binding inhibition.

DSF experiments resulted in 20 compounds with positive $T_m$ shifts and another 20 with negative $T_m$ shifts, while a number of compounds exhibited fluorescent quenching or autofluorescence, obfuscating some of the data (FIG. 17A). Thus, while DSF provided a good base for removing a number of compounds that showed no evidence of binding to BCL2A1, the number of compounds with fluorescence issues such as quenching necessitated an orthogonal approach.

Figure 17B:
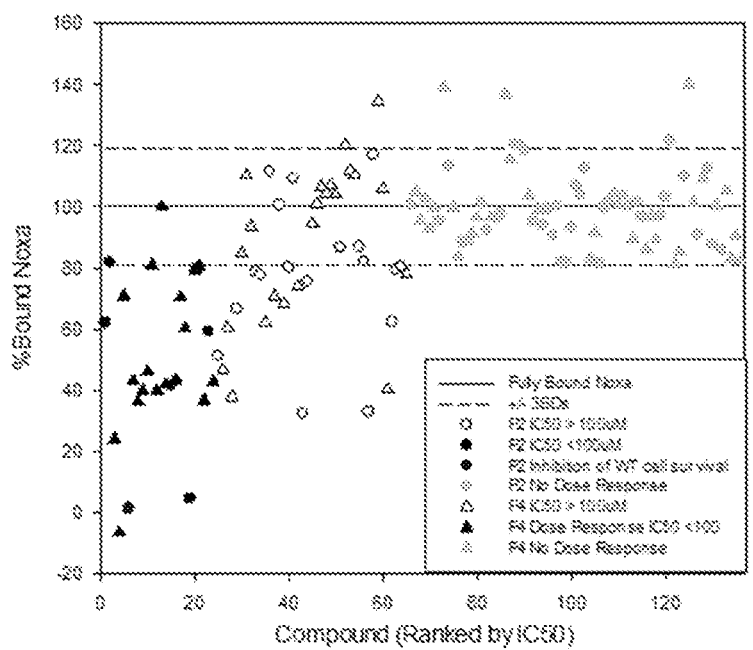

Representative compounds were additionally tested for inhibition of BH3 binding through competition-based fluorescence polarization (FP) assays. These assays were carried out using fluorescently labeled NOXA peptide which binds within the BH3-binding groove. The FP assay measures the tumbling rate of the labeled NOXA peptide. When NOXA is bound to A1, its rate of tumbling is low (and FP is high), whereas an effective inhibitor compound will displace NOXA, causing a fast rate of tumbling (and low FP value). Initially, a single high-dose experiment was performed with each compound using 100 µM of compound with BCL2A1 and FITC-NOXA, to observe the relative inhibition of the A1-NOXA interaction (FIG. 17B). This resulted in 41 small molecules that deviated by three or more standard deviations from the control mean towards inhibition of binding.

Figure 18A:
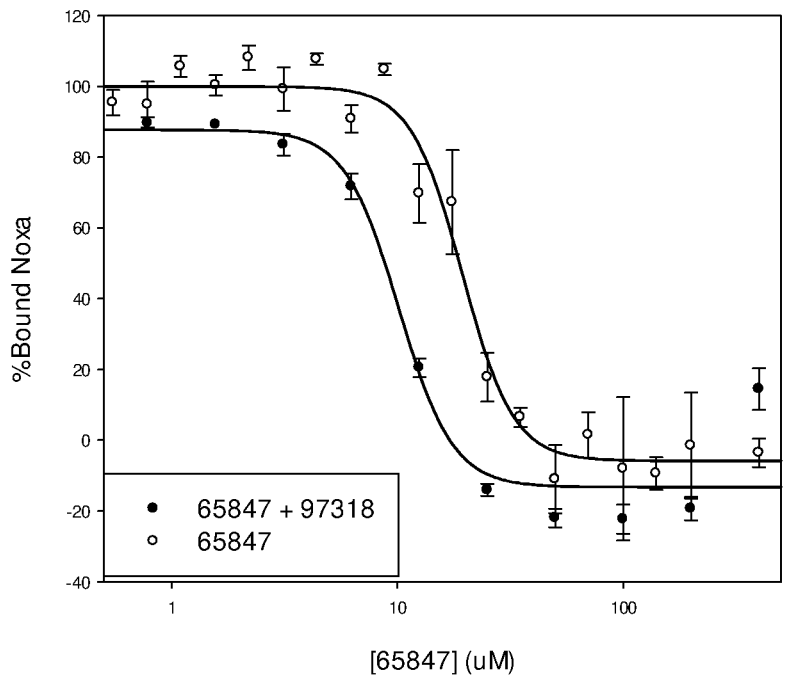
FIGS. 18A-B: Compounds that displayed decreased polarization or increased $T_m$ values at least three standard deviations from the control were tested in a dose response FP experiment and their $IC_{50}$ were determined. Those with an $IC_{50}$<50 μM were tested in synergy experiments utilizing NSC-97318 at its $IC_{50}$ in combination with a titration of P4 inhibitors (A, B).
Figure 18B:
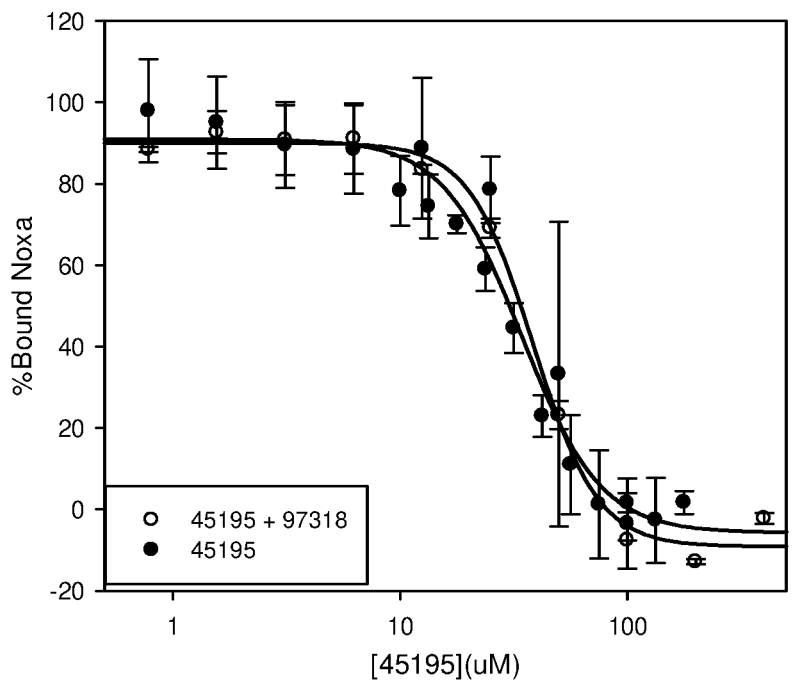
Figure 19:
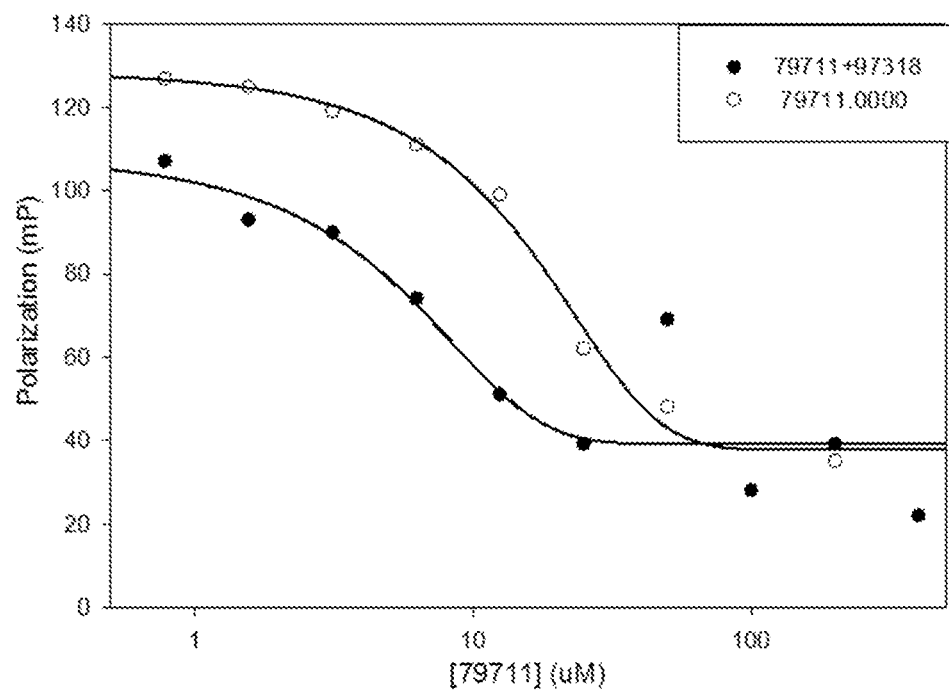
FIG. 19: Representative fluorescence polarization plots showing reduced $IC_{50}$ values upon P2 and P4 ligand binding. Shows inhibitor binding synergy of a P2 inhibitor (97318) and a P4 inhibitor (79711) lowering the $IC_{50}$ from 17.1 μM to 6.3 μM.
Figure 21A:
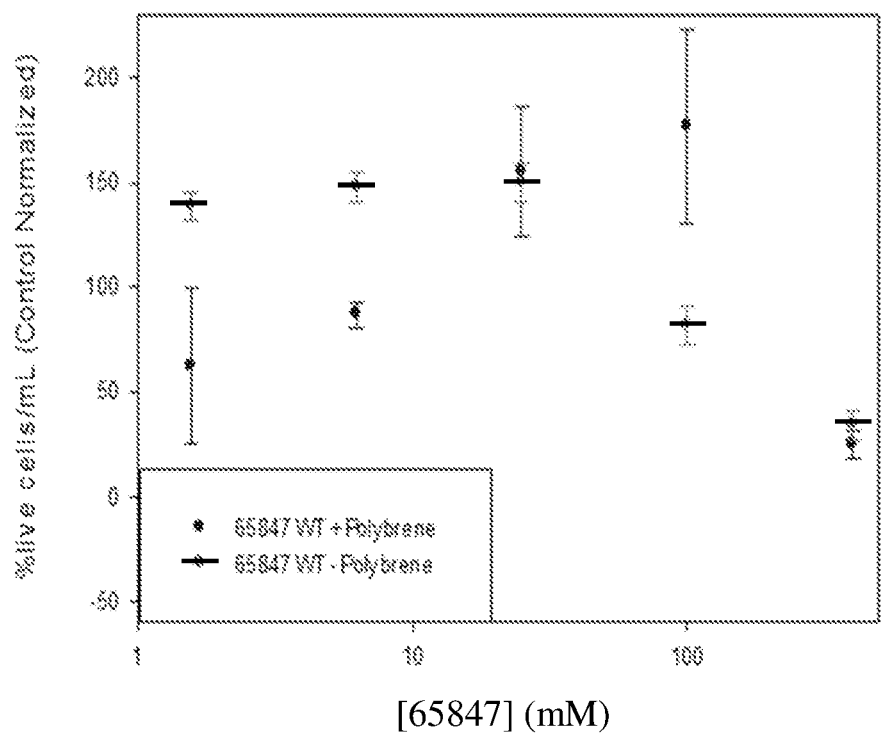
FIG. 21A-F: Biological activity of candidate BCL2A1/BLF1 inhibitor compounds. An in vitro apoptosis assay utilizing primary splenocyte cells was performed with compounds 65847 (A), 9360 (B), 45538 (C), 7223 (D), 45195 (E) and 97318 (F). WT cells from wild-type mice; Bax/Bak$^{-/-}$-cells from Bax/Bak knockout mice; Polybrene™ is hexadimethrine bromide.
Figure 21B:
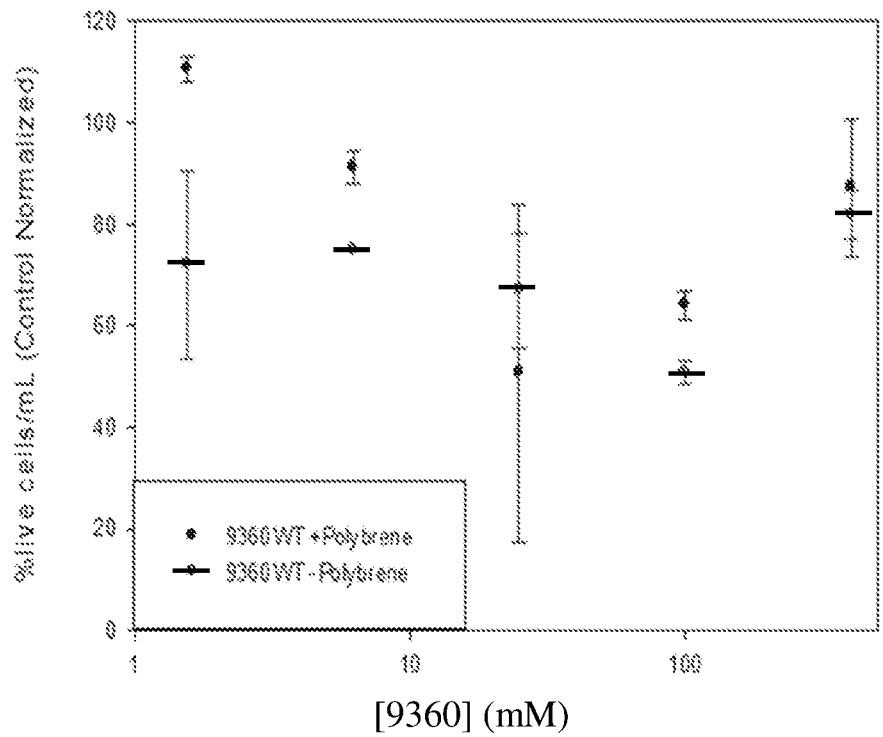
Figure 21C:
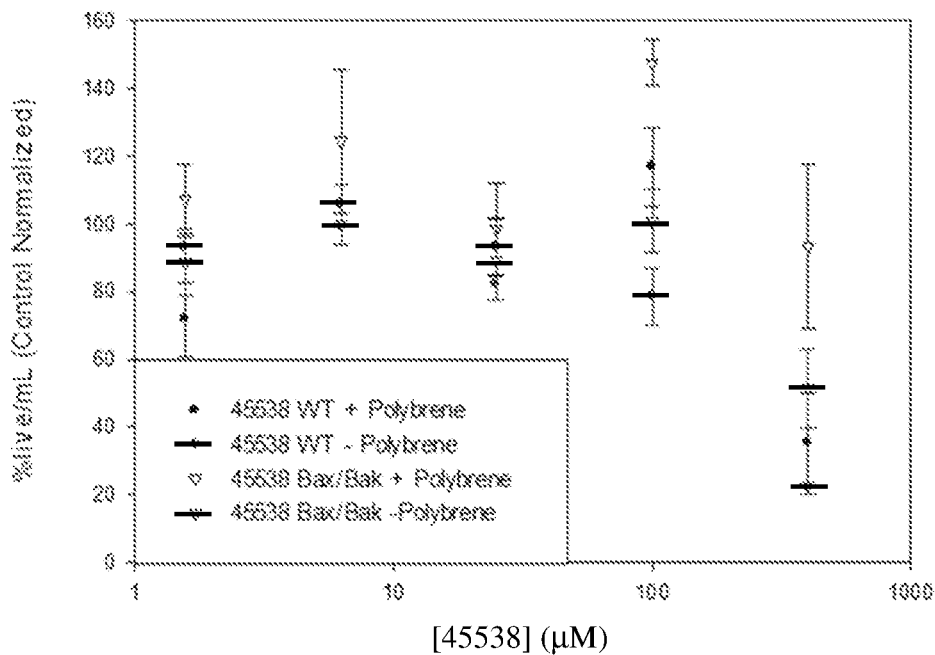
Figure 21D:
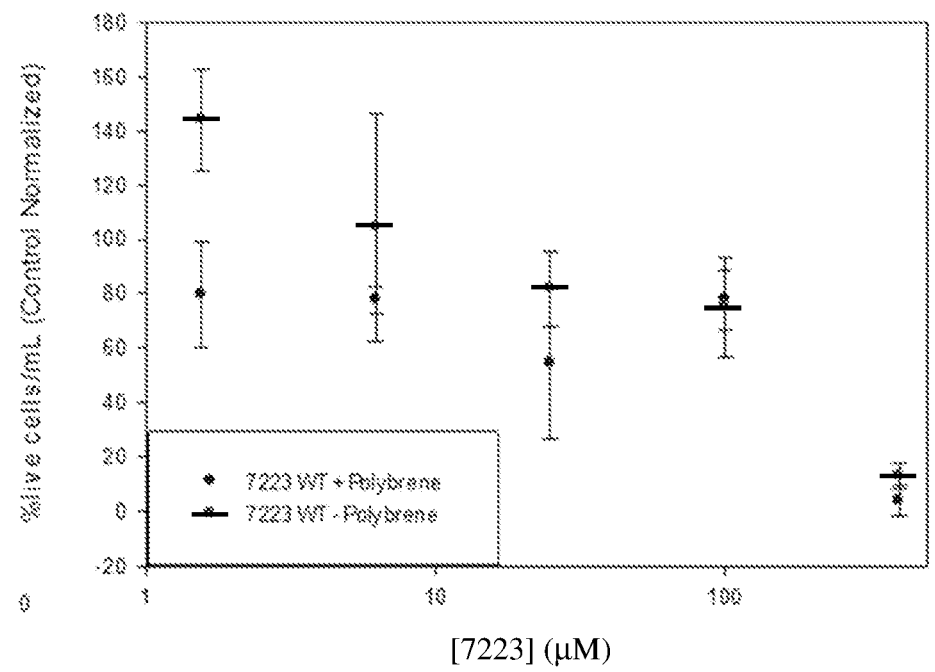
Figure 21E:
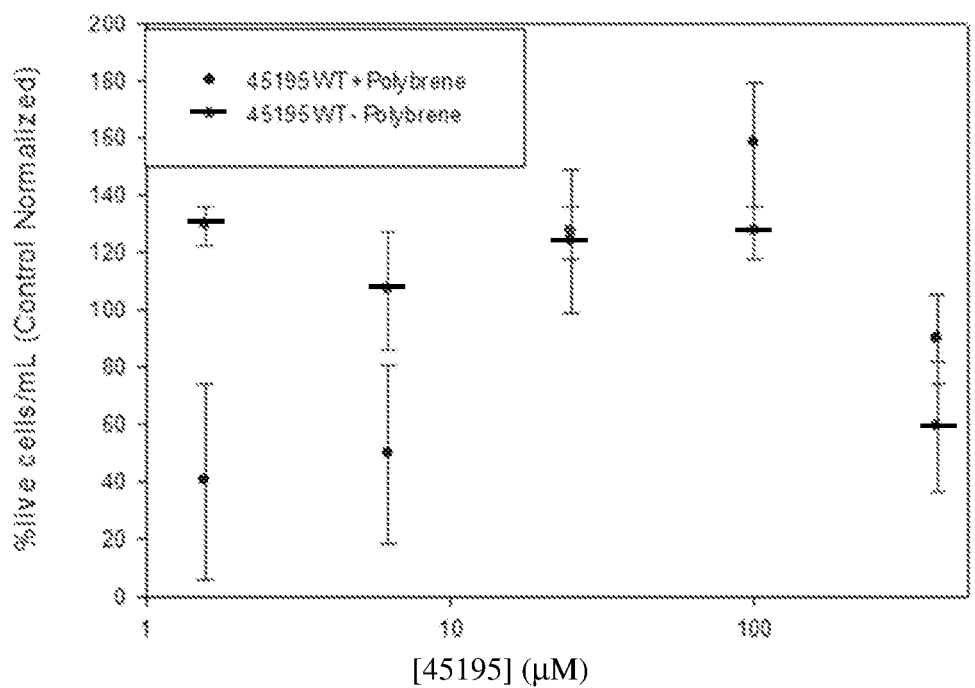
Figure 21F:
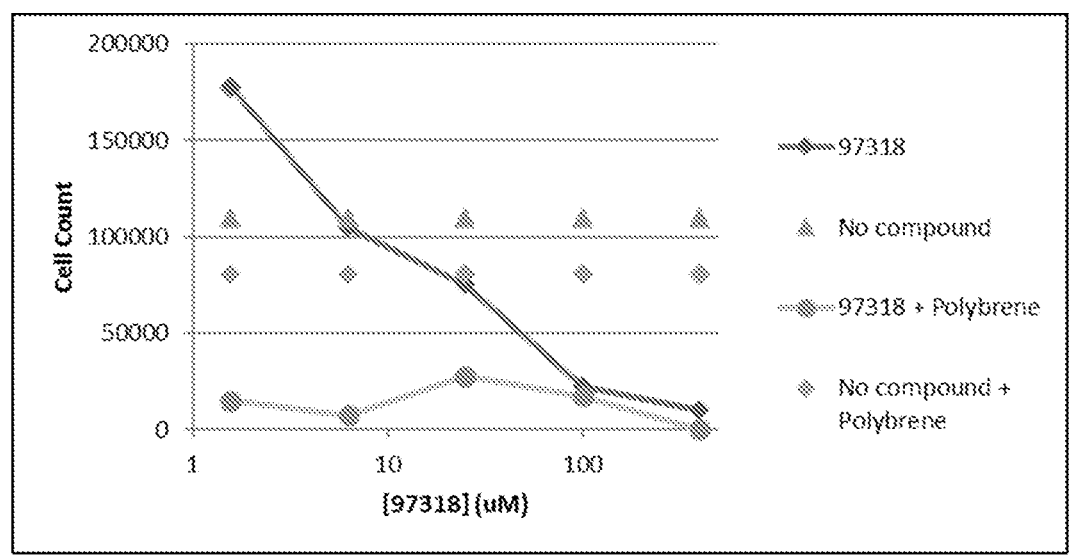

These compounds and any that were three standard deviations or more above the thermal shift controls in the DSF assays, along with those that were initially derived from early compounds with reasonable $IC_{50}$ values, were tested in a dose-response experiment. To this end, 30 putative P2 inhibitors and 44 putative P4 inhibitors had their $IC_{50}$ values determined. Of the dose responses, there was a surprising enrichment of putative P4 inhibitors among those that had $IC_{50}$ values less than 50 µM. Compounds that had an $IC_{50}$ of less than 50 µM were tested for additive and/or synergistic effects with compounds predicted to interact with the other pocket. NSC-97318 and NSC-65847 (FIG. 18A) show an additive effect when the observed $IC_{50}$ values of the compounds together are plotted onto the isobologram of the independent compounds' $IC_{50}$. The following linear equation was used in the calculations (Tallarida et al., 2011), $$\frac{a}{A} + \frac{b}{B} = 1, \qquad \text{Equation 1}$$

where a and b are the concentrations for NSC-97318 and NSC-65847 at which 50% inhibition of NOXA binding is observed when combined and A and B are the IC50 values of the compounds independently of one another. Other compounds tested with NSC-97318 did not show the same additivity (FIG. 18B). NSC-9360, NSC-45195 and NSC-65847 show cooperative inhibition of NOXA binding with NSC-15508 (FIG. 17C). Other interactions of interest included NSC-97318 and 79711 (FIG. 19).

A checkerboard experiment demonstrated the overall additivity in binding between P2 and P4 inhibitor compounds (FIG. 20).

Compounds were additionally ordered and tested using a structure activity relationship (SAR)-type approach of compounds related to those that were performing well in initial testing. For each compound derived from another in the above-described screens, full dose responses were tested and $IC_{50}$ values were calculated. This approach served to build upon existing lead compounds and search for related molecules with higher affinity interactions, demonstrating some key functional groups likely involved in binding. For instance, NSC-45195 and NSC-65847 are structurally quite similar, with NSC-65847 being a duplication of most of the NSC-45195 scaffold with symmetry across the di-azide bonds, yet the larger molecule drives roughly a two-fold increase in inhibition. Effective P2 inhibitors seem to require a hydrophobic group to interact with the deepest cavity of the P2 pocket, along with some polar groups to facilitate proper registry of binding. Many of the predicted binding compounds contain a sulfonate group which is predicted to interact between the P2 and P4 pockets.

As an additional screen for activity, compounds were clustered with other compounds that show similar changes in gene expression profiles to a BCL2A1 knockdown. This analysis revealed a large cluster of compounds related to NSC-97318 and NSC-65847, along with other P2 and P4 predicted inhibitors, with a Tanimoto coefficient above 0.6. This same clustering performed with a Tanimoto cutoff of 0.8, while not conserved for all compounds included in this analysis, still found clustering for NSC-97318 with a number of LINCS compounds. The LINCS-derived compounds included in this clustering were identified through iLINCS by searching for a knockdown of BCL2A1 and identifying concordant chemical perturbagen signatures as indicating likely apoptosis pathway-specific inhibitors. Clustering based on Tanimoto coefficient yielded distinct compound clusters that are comprised of molecules with similar chemical moieties that likely target various members of the apoptotic pathway. The connectivity analysis between BCL2A1 gene knockdown and chemical perturbation transcriptional signatures, coupled with in vitro inhibition suggests a group of structurally-related compounds that could drive inhibition of A1.

An in vitro apoptosis assay utilizing primary splenocyte cells was used as a model system. In this system, compounds were added to wild-type primary splenocyte cells from mice that had been cultured and activated over four days. Lead compounds with $IC_{50}$ values below 50 μM were added to the cells before observing cell death. Mice deficient in Bax/Bak are unable to undergo intrinsic apoptosis due to the lack of the executioners in the pathway. Thus, cell death seen in WT cells (circles) with inhibitors that is also seen in the Bax/Bak$^{-/-}$ mice suggests cytotoxicity as opposed to specific inhibition (FIG. 21). Polybrene™ (hexadimethrine bromide) is a transfection reagent used to assist negatively-charged DNA molecules in traversal of the plasma membrane. Polybrene was included here to test whether it would improve the activity of negatively charged compounds. Although these compounds showed mixed activity, a delivery vehicle effective to improve the transport of the compounds across the cell membrane would likely improve their activity. These studies demonstrate the feasibility of developing a potent and specific inhibitor to BCL2A1/BFL1 and provide several candidate molecules, including NSC-97318 which showed strong inhibition of Noxa binding in FP assays with some effect on cell survival.

Methods

In Silico Docking

Docking simulations were performed using a parallelized version of AutoDock 4.2.6 (Forli et al., 2012). Docking was performed using mouse A1 (PDB: 2VOH) bound to the BAK/BH3-domain and human BFL1 (PDB: 3MQP) bound to the NOXA BH3-only peptide. Two pockets were selected for targeting of each protein, the P2 canonical BH3-binding site (x: −6, y: 10, z: 59) (npoints x: 40, y: 34, z: 45), and the shallower P4 pocket specific to A1/BFL1 (x: 6, y: 14, z: 56) (npoints x: 52, y: 36, z: 50). These docking simulations were performed on the Cincinnati Children's Medical Center computational cluster over three iterations utilizing a subset of the 2007 NCI library consisting of 90,086 compounds. Each iteration decreased the overall number of compounds while increasing the depth of the search. The first iteration used the whole library with 250,000 evaluations. The second iteration took the top 30,000 compounds sorted by predicted $K_i$ and used 1,000,000 evaluations, and the final iteration used 10,000,000 evaluations on the top 3,000 compounds. After each iteration for A1, an identical iteration was run on BFL1 and only the overlapping top compounds were carried forward into the next iteration. This intersection allowed for identification of compounds that would likely interact with both the human and mouse homologs and took into account slight differences that may be present from different binding partners.

After all three iterations were complete and the intersection of the top 450 compounds was performed, the remaining compounds were entropy-filtered based on the convergence of their predicted poses. Compounds with clustering entropy greater than 0.5 were removed, leaving approximately 150 compounds for targeting each pocket. These compounds were clustered based on similarity of chemical moieties via the Tanimoto Coefficient using the ChemmineR package in R (Cao et al., 2008). Representatives from each cluster with the best predicted $K_i$ were selected for in vitro biochemical testing. Of the selected compounds, 79 targeted the P2 pocket and 79 targeted the P4 pocket.

Protein Expression/Purification

A1 residues 1-152 (P104K, C113S) were expressed in the BL21 strain of *Escherichia coli* in an H596 vector with a hexa-His-MBP tag. All purification steps were performed in 20 mM Tris pH 7.0 and 500 mM NaCl. Cells were induced with 0.2 mM IPTG overnight after which they were pelleted and lysed via sonicator. After cell lysis, cell debris was pelleted out and the supernatant was harvested, filtered and run through Ni-affinity chromatography. Protein-containing fractions were pooled and the tag was removed with TEV protease rocking at room temperature overnight. The cleaved proteins were run over an additional Ni column to remove the His-MBP tag and His-tagged TEV protease. Finally, protein was run over a S75 size exclusion column and concentrated to suit assay needs.

Thermal Shift Assay

100 μM of each compound was applied to purified A1 at 4.4 μM in triplicate. Sypro Orange dye was added at a final dilution of 1:1000 to protein- and compound-containing wells. An Applied Biosystems StepOnePlus was used to perform Differential Scanning Fluorimetry (DSF) by elevating the temperature from 20° C. to 99° C. and measuring fluorescence at every half degree C. Melting temperature was recorded as the maximum of the first derivative, indicating half of the protein population was unfolded. Compounds that were observed to have a positive change in $T_m$ compared to the control of greater than three standard deviations were included for future assays.

Fluorescence Polarization Assay

Compounds were additionally tested for specificity of binding by displacement of FITC-labeled mouse NOXA (mNoxa; Peptide 2.0) peptide via fluorescence polarization assay (FP). FP assays were performed in two steps: single-point high-concentration compounds and dose response of fluorescence polarization hits. A1 was added at 3 μM to 100 μM of each compound in 20 mM Tris pH 7, 500 mM NaCl, 0.005% Tween-20 buffer. After addition of 375 nM labeled mNOXA, 96-well plates were incubated overnight at 20° C. in the dark to achieve equilibrium before fluorescence polarization was measured with a Biotek Synergy H2. Autofluorescent compounds and fluorescent quenching compounds were corrected via ratiometric correction as described by Shapiro et al., 2009. Any compounds that showed a significant shift in polarization, along with those identified in the thermal shift assays had a dose response measured via FP.

Dose response curves were measured by adding 3 μM A1 to a serial two-fold dilution series of each compound ranging from 400 μM to 781 nM in 20 mM Tris pH 7, 500 mM NaCl, 0.005% Tween-20 buffer. Some compounds were further tested to assess the accuracy of these two-fold dilutions with serial 1.33-fold dilutions. A1, compounds, buffer and lastly, 375 nM FITC-labeled mNOXA were added to each well and incubated in the dark at 20° C. overnight to achieve equilibrium, followed by measurement of polarization. All dose responses were performed in triplicate.

LINCS Gene Expression Analysis

LINCS compounds were identified by concordance with a BFL1 knockdown signature as computed through iLINCS (Koleti et al., 2018; Keenan et al., 2018). The compounds included only those within the top 0.5% of all perturbagen signatures' concordance values. The SMILES code of each LINCS compound was obtained and converted to FP2 fingerprints using the OpenBabel software implemented in R through the ChemmineOB package (O'Boyle et al., 2011). These fingerprints were compared using the Tanimoto correlation and clustered via hierarchical clustering of Tanimoto distance (Bajusz et al., 2015). After hierarchical clustering, centroids were identified from each cluster with at least four representatives and multi-dimensional scaling was performed to display approximate Tanimoto distances between each centroid.

Cell Assays

Single-cell suspensions from spleen were generated by maceration through a 100 μm nylon mesh followed by LympholyteM ficoll gradient separation (Cedarlane Labs, Burlington, N.C.). Purified cells were then cultured on anti-CD3 coated (3 μg/mL, coated overnight, Biolegend, San Diego, Calif.) six-well plates in the presence of soluble anti-CD28 (2 μg/mL, Bio X Cell, West Lebanon, N.H.) and IL-2 (10 ng/mL, R&D Systems, Inc., Minneapolis, Minn.) in RPMI media (Life Technologies, Carlsbad, Calif.) for 24 hours at 37° C. Cells were then washed and cultured again in IL-2 (10 ng/mL) for 24 hours at 37° C. Cells were harvested and cultured for 24 hours on anti-CD3 coated 96-well plates at 500,000 cells per well with 2 μg/mL soluble anti-CD28, 10 ng/mL IL-2, 0.125 μg purified anti-mouse FasL (Biolegend, San Diego, Calif.), and varying concentrations of A1 inhibitor compounds+/−polybrene (2 μg/mL, EMD Millipore, Burlington, Mass.). Cells were then harvested and live and dead cells enumerated by trypan blue staining using the TC20 automated cell counter (Bio-Rad Laboratories, Des Plaines, Ill.).

What is claimed is:

1. A method for attenuating an immune response characterized by neutrophil-mediated inflammation in a subject in need of such treatment, the method comprising administering to the subject an inhibitor of BFL1, wherein the inhibitor is a small organic molecule that binds to the P2 or P4 pocket, or both, of the BH3 domain of BFL1.

2. The method of claim 1, wherein the inhibitor is a compound of Formula Ia

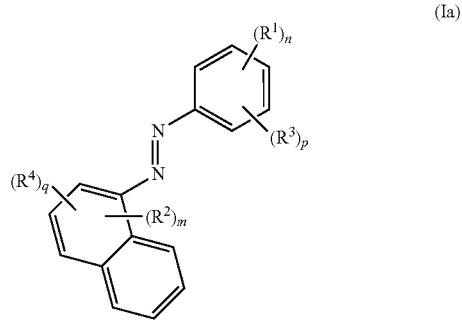

wherein,
each $R^1$ is independently selected from the group consisting of $C_{1-8}$ alkyl, $C_{1-8}$ alkoxy, halo, —OH, —S(O)$_2$—$R^{1a}$, —P(O)(OH)—$R^{1a}$, —NH$_2$, —NH—$C_{1-8}$ alkyl, —N($C_{1-8}$ alkyl)$_2$, and —NO$_2$, or two $R^1$ groups on adjacent ring vertices combine to form a 6-membered aromatic ring;
each $R^{1a}$ is independently selected from the group consisting of H, OH, $C_{1-8}$ alkyl, and $C_{1-8}$ alkoxy;
the subscript n is an integer from 0 to 3;
each $R^2$ is independently selected from the group consisting of $C_{1-8}$ alkyl, $C_{1-8}$ alkoxy, halo, —OH, —S(O)$_2$—$R^{2a}$, —P(O)(OH)—$R^{2a}$, —NH$_2$, —NH—$C_{1-8}$ alkyl, —N($C_{1-8}$ alkyl)$_2$, and —NO$_2$;
each $R^{2a}$ is independently selected from the group consisting of H, OH, $C_{1-8}$ alkyl, and $C_{1-8}$ alkoxy;
the subscript m is an integer from 0 to 3;
$R^3$ is selected from the group consisting of —N=N-phenyl, —N=N-naphthyl, —N=N-phenyl-N=N-naphthyl, and —N=N-phenyl-N=N-phenyl, wherein each phenyl and naphthyl moiety are substituted with from 0 to 3 $R^{3a}$ moieties;
each $R^{3a}$ is independently selected from the group consisting of $C_{1-8}$ alkyl, $C_{1-8}$ alkoxy, halo, —OH, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, —S(O)$_2$—$C_{1-8}$ alkyl, —P(O)(OH)—OH, —P(O)(OH)—H, —P(O)(OH)—O—$C_{1-8}$ alkyl, and —P(O)(OH)—$C_{1-8}$ alkyl;
the subscript p is an integer from 0 to 1; and
$R^4$ is selected from the group consisting of —C(O)—NR$^{4a}$-phenyl, wherein each phenyl group is substituted with from 0 to 3 $R^{4b}$ moieties;
$R^{4a}$ is selected from the group consisting of H and $C_{1-8}$ alkyl;
each $R^{4b}$ is independently selected from the group consisting of $C_{1-8}$ alkyl, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, and —S(O)$_2$—$C_{1-8}$ alkyl;
the subscript q is an integer from 0 to 1; or
a pharmaceutically acceptable salt thereof.

3. The method of claim 2, where p=0, and wherein the inhibitor is

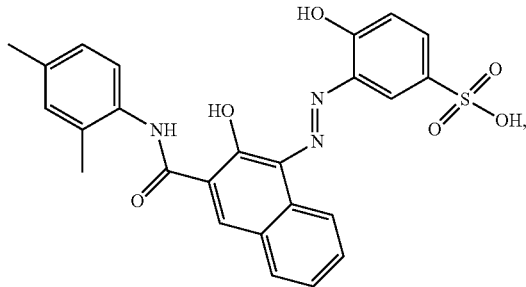 [SMILES: Cc1ccc(NC(=O)c2cc3ccccc3c(/N=N/c3cc(S(=O)(=O)O)ccc3O)c2O)c(C)c1]

or a derivative thereof in which the azo bond is reduced to an azine bond or replaced with a sulfonamide, thioether, or sulfone linker, or an isosteric alkene or alkane bond.

4. The method of claim 3, wherein the compound is a derivative in which the sulfonate group is converted to a sulfone group.

5. The method of claim 1, wherein the subject is a human subject.

6. The method of claim 1, wherein the method comprises administering two BFL1 inhibitors to the subject, wherein each of the BFL1 inhibitors binds to a different region of BFL1.

7. The method of claim 6, wherein one of the inhibitors binds to the P4 pocket of BFL1 and the other binds to the P2 pocket of BFL1.

8. The method of claim 1, wherein the BFL1 inhibitor is encapsulated in a liposome-based nanoparticle comprising a targeting moiety selected from a polypeptide or an antibody, or antigen-binding fragment thereof, that binds to a neutrophil-specific cell surface glycoprotein, preferably selected from CD177, CD66b, SIRPa, and SIGLEC9.

9. The method of claim 3, wherein the inhibitor is encapsulated within a liposome-based nanoparticle comprising a targeting moiety.

10. The method of claim 9, wherein the targeting moiety is selected from a polypeptide or an antibody, or antigen-binding fragment thereof, that binds to a neutrophil-specific cell surface glycoprotein.

11. The method of claim 10, wherein the neutrophil-specific cell surface glycoprotein is selected from CD177, CD66b, SIRPa, and SIGLEC9.

12. The method of claim 7, wherein the two BFL1 inhibitors are compound 1.001 and 1.003 or compound 1.001 and 1.004.

13. A method for attenuating an immune response in a subject in need of such treatment, the method comprising administering to the subject an inhibitor of BFL1, wherein the inhibitor is a compound of Formula Ia

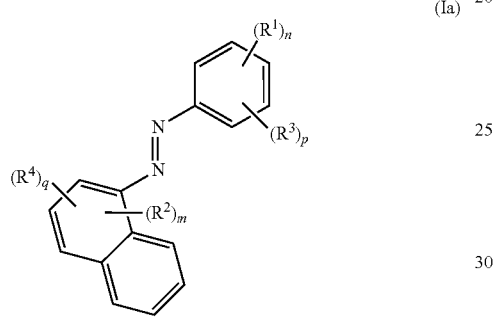

wherein,
- each $R^1$ is independently selected from the group consisting of $C_{1-8}$ alkyl, $C_{1-8}$ alkoxy, halo, —OH, —S(O)$_2$—$R^{1a}$, —P(O)(OH)—$R^{1a}$, —NH$_2$, —NH—$C_{1-8}$ alkyl, —N($C_{1-8}$ alkyl)$_2$, and —NO$_2$, or two $R^1$ groups on adjacent ring vertices combine to form a 6-membered aromatic ring;
- each $R^{1a}$ is independently selected from the group consisting of H, OH, $C_{1-8}$ alkyl, and $C_{1-8}$ alkoxy;
- the subscript n is an integer from 0 to 3;
- each $R^2$ is independently selected from the group consisting of $C_{1-8}$ alkyl, $C_{1-8}$ alkoxy, halo, —OH, —S(O)$_2$—$R^{2a}$, —P(O)(OH)—$R^{2a}$, —NH$_2$, —NH—$C_{1-8}$ alkyl, —N($C_{1-8}$ alkyl)$_2$, and —NO$_2$;
- each $R^{2a}$ is independently selected from the group consisting of H, OH, $C_{1-8}$ alkyl, and $C_{1-8}$ alkoxy;
- the subscript m is an integer from 0 to 3;
- $R^3$ is selected from the group consisting of —N═N-phenyl, —N═N-naphthyl, —N═N-phenyl-N═N-naphthyl, and —N═N-phenyl-N═N-phenyl, wherein each phenyl and naphthyl moiety are substituted with from 0 to 3 $R^{1a}$ moieties;
- each $R^{3a}$ is independently selected from the group consisting of $C_{1-8}$ alkyl, $C_{1-8}$ alkoxy, halo, —OH, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, —S(O)$_2$—$C_{1-8}$ alkyl, —P(O)(OH)—OH, —P(O)(OH)—H, —P(O)(OH)—O—$C_{1-8}$ alkyl, and —P(O)(OH)—$C_{1-8}$ alkyl;
- the subscript p is an integer from 0 to 1; and
- $R^4$ is selected from the group consisting of —C(O)—NR$^{4a}$-phenyl, wherein each phenyl group is substituted with from 0 to 3 $R^{4b}$ moieties;
- $R^{4a}$ is selected from the group consisting of H and $C_{1-8}$ alkyl;
- each $R^{4b}$ is independently selected from the group consisting of $C_{1-8}$ alkyl, —NH$_2$, —NH—$C_{1-8}$ alkyl, —N($C_{1-8}$ alkyl)$_2$, —S(O)$_2$—OH, —S(O)$_2$—H, —S(O)$_2$—O—$C_{1-8}$ alkyl, and —S(O)$_2$—$C_{1-8}$ alkyl;
- the subscript q is an integer from 0 to 1; or
- a pharmaceutically acceptable salt thereof.

14. The method of claim 13, wherein the inhibitor is

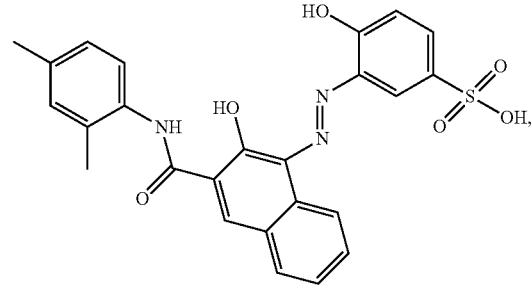 [SMILES: Cc1ccc(NC(=O)c2cc3ccccc3c(/N=N/c3cc(S(=O)(=O)O)ccc3O)c2O)c(C)c1]

or a derivative thereof in which the azo bond is reduced to an azine bond or replaced with a sulfonamide, thioether, or sulfone linker, or an isosteric alkene or alkane bond.

15. The method of claim 14, wherein the compound is a derivative in which the sulfonate group is converted to a sulfone group.

16. The method of claim 13, wherein the subject is a human subject.

17. The method of claim 13, wherein the method comprises administering two BFL1 inhibitors to the subject, wherein each of the BFL1 inhibitors binds to a different region of BFL1.

18. The method of claim 17, wherein one of the inhibitors binds to the P4 pocket of BFL1 and the other binds to the P2 pocket of BFL1.

19. The method of claim 18, wherein the two BFL1 inhibitors are compound 1.001 and 1.003 or compound 1.001 and 1.004.

20. The method of claim 13, wherein the BFL1 inhibitor is encapsulated in a liposome-based nanoparticle comprising a targeting moiety.

21. The method of claim 20, wherein the targeting moiety is selected from a polypeptide or an antibody, or antigen-binding fragment thereof, that binds to a neutrophil-specific cell surface glycoprotein.

22. The method of claim 21, wherein the neutrophil-specific cell surface glycoprotein is selected from CD177, CD66b, SIRPa, and SIGLEC9.

* * * * *